(12) United States Patent
Kim

(10) Patent No.: US 12,171,660 B2
(45) Date of Patent: Dec. 24, 2024

(54) TRANSCATHETER DEVICE FOR TREATING TRICUSPID VALVE REGURGITATION

(71) Applicant: June Hong Kim, Busan (KR)

(72) Inventor: June Hong Kim, Busan (KR)

(73) Assignees: TAU MEDICAL USA, INC., Centreville, VA (US); TAU MEDICAL, INC., Busan (KR)

( * ) Notice: Subject to any disclaimer, the term of this patent is extended or adjusted under 35 U.S.C. 154(b) by 414 days.

(21) Appl. No.: 17/535,381

(22) Filed: Nov. 24, 2021

(65) Prior Publication Data

US 2022/0160500 A1  May 26, 2022

Related U.S. Application Data

(60) Provisional application No. 63/283,032, filed on Nov. 24, 2021, provisional application No. 63/227,871, (Continued)

(51) Int. Cl.
*A61F 2/24* (2006.01)
*A61M 25/00* (2006.01)
(Continued)

(52) U.S. Cl.
CPC ............ *A61F 2/246* (2013.01); *A61F 2/2466* (2013.01); *A61M 25/0041* (2013.01); (Continued)

(58) Field of Classification Search
CPC ... A61F 2/246; A61F 2/2466; A61M 25/0041; A61M 25/04; A61M 25/09; A61M 2025/1097
See application file for complete search history.

(56) References Cited

U.S. PATENT DOCUMENTS

| 5,207,228 A | 5/1993 | Roelandt et al. |
| 8,126,570 B2 | 2/2012 | Manning et al. |

(Continued)

FOREIGN PATENT DOCUMENTS

| EP | 362866 A1 | 6/2020 |
| WO | WO 2020/197854 A1 | 10/2020 |

OTHER PUBLICATIONS

International Search Report and Written Opinion dated Apr. 20, 2022 from corresponding International Application No. PCT/US21/60872.

(Continued)

*Primary Examiner* — Brian A Dukert
*Assistant Examiner* — Rebecca Lynee Zimmerman
(74) *Attorney, Agent, or Firm* — Justin H. Kim

(57) ABSTRACT

A transcatheter device for treating the tricuspid valve regurgitation. The transcatheter device comprises a main shaft, a proximal portion, a distal tail, and a spacer body mounted on the main shaft and located between the proximal portion and the distal tail. This transcatheter device could be used for treating tricuspid valve regurgitation in a patient's heart. All or part of the transcatheter device is supported by the main shaft. The spacer body is mounted on the shaft, which travels through the spacer body. Also disclosed are a coaptation assembly that comprises the transcatheter device, and a method of treating tricuspid valve regurgitation using the transcatheter device.

11 Claims, 57 Drawing Sheets

Related U.S. Application Data filed on Jul. 30, 2021, provisional application No. 63/224,337, filed on Jul. 21, 2021, provisional application No. 63/180,656, filed on Apr. 28, 2021, provisional application No. 63/163,772, filed on Mar. 19, 2021, provisional application No. 63/146,552, filed on Feb. 5, 2021, provisional application No. 63/137,589, filed on Jan. 14, 2021, provisional application No. 63/118,631, filed on Nov. 25, 2020.

(51) Int. Cl.
    *A61M 25/04*     (2006.01)
    *A61M 25/09*     (2006.01)
    *A61M 25/10*     (2013.01)

(52) U.S. Cl.
    CPC ............. *A61M 25/04* (2013.01); *A61M 25/09* (2013.01); *A61M 2025/1097* (2013.01)

(56) References Cited

U.S. PATENT DOCUMENTS

| | | |
|---|---|---|
| 2007/0198082 A1 | 8/2007 | Kapadia et al. |
| 2009/0137968 A1 | 5/2009 | Rottenberg |
| 2013/0190798 A1 | 7/2013 | Kapadia |
| 2013/0338763 A1* | 12/2013 | Rowe .................... A61F 2/2427 623/2.11 |
| 2020/0000592 A1 | 1/2020 | Lee et al. |
| 2020/0229916 A1 | 7/2020 | Kim et al. |

OTHER PUBLICATIONS

Extended European Search Report issued Sep. 27, 2024 in corresponding European Application No. 21899140.4.

* cited by examiner

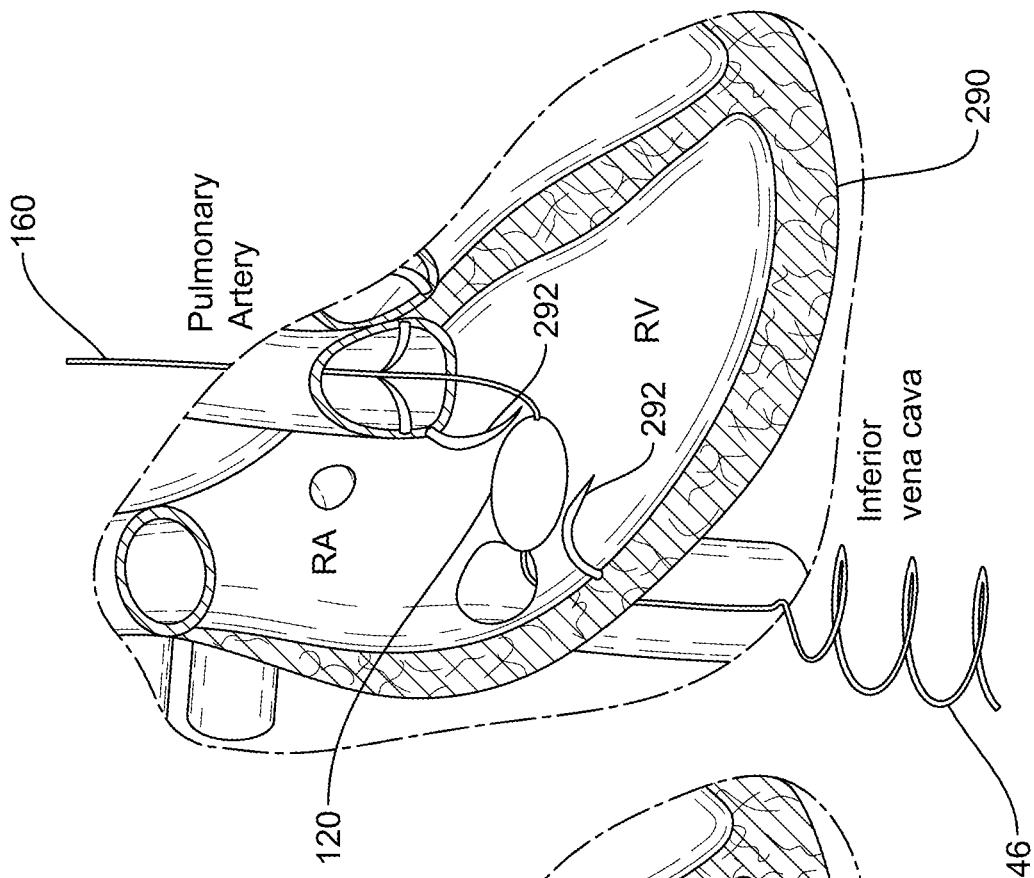
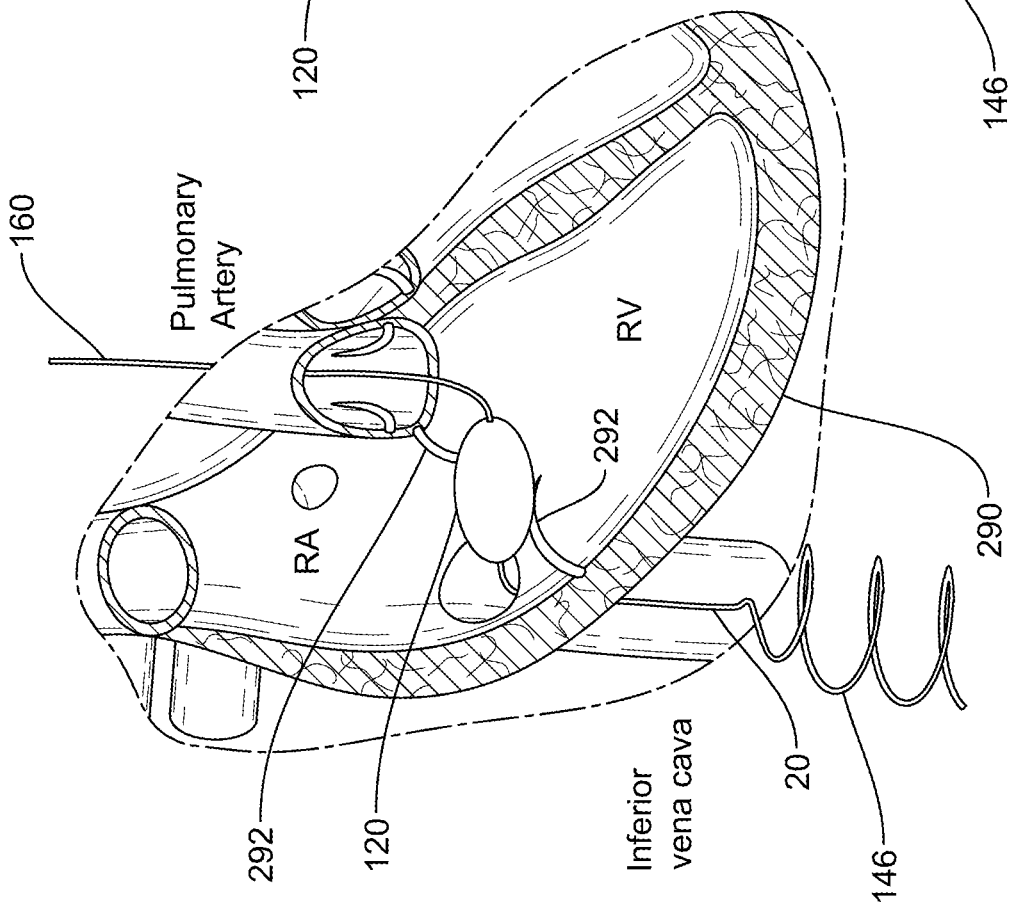
FIG. 4A
FIG. 4B

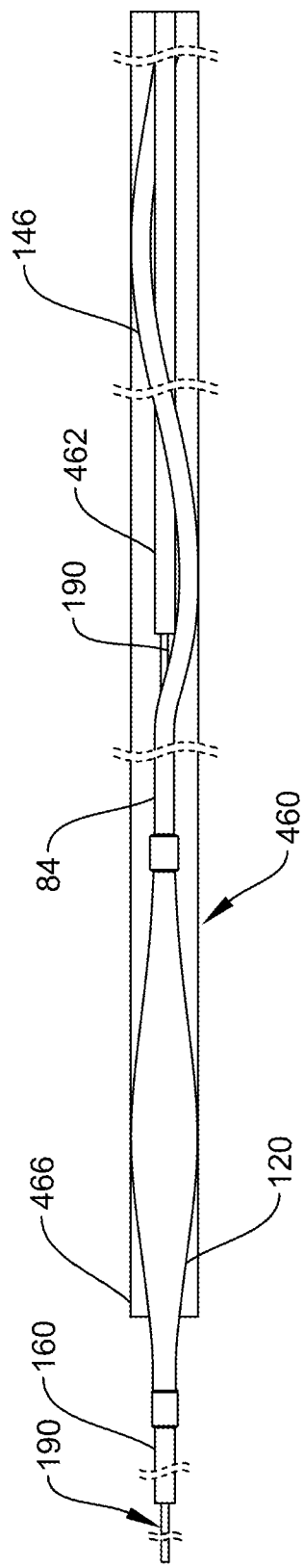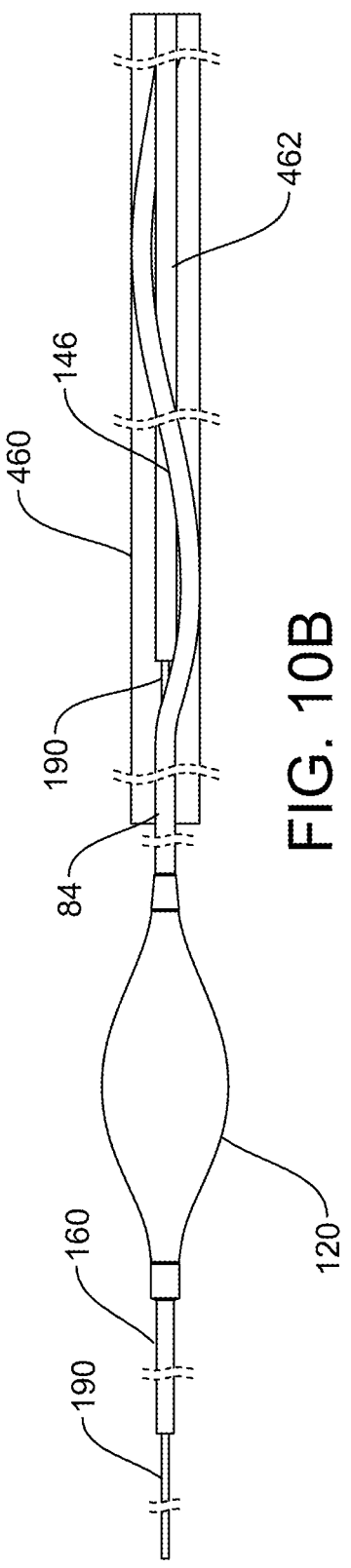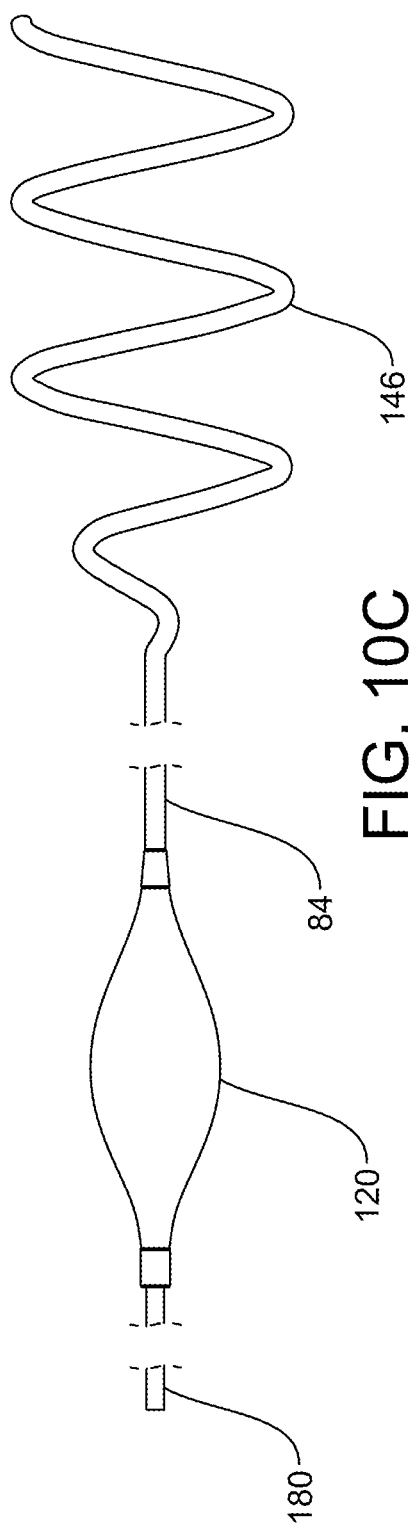

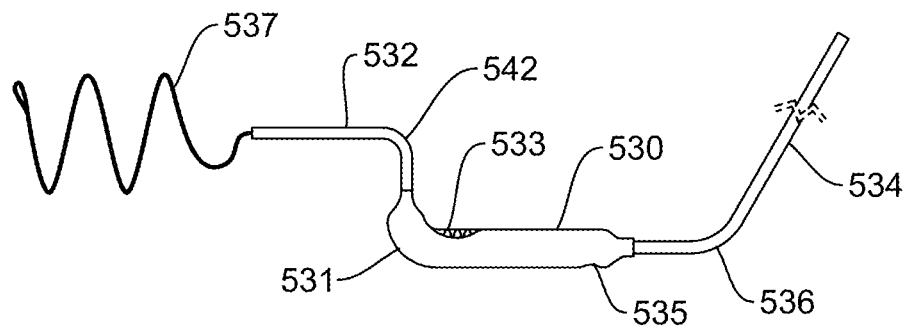
FIG. 21A
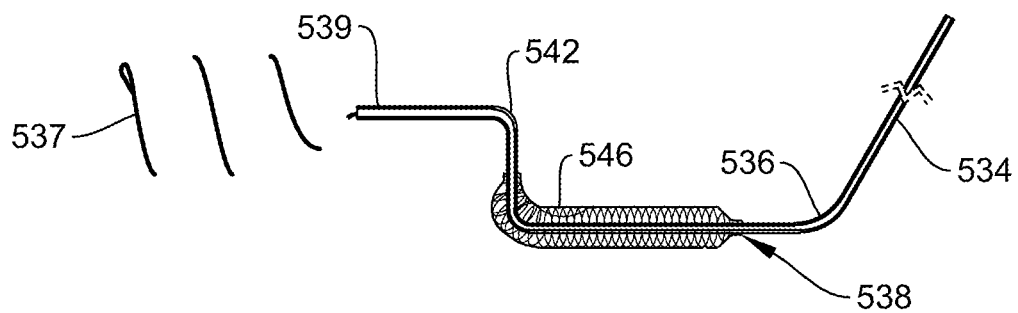
FIG. 21B
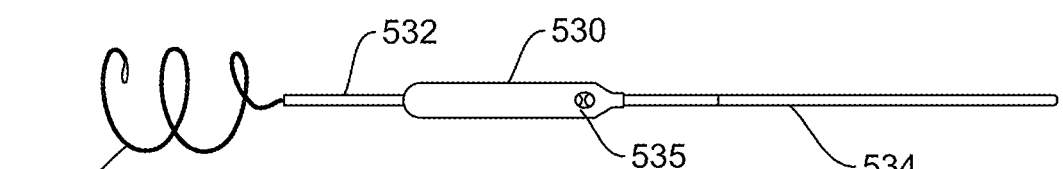
FIG. 21C
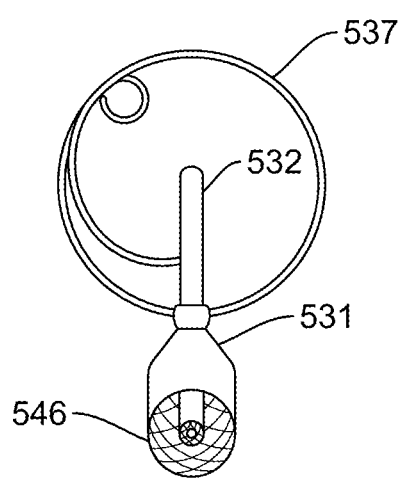 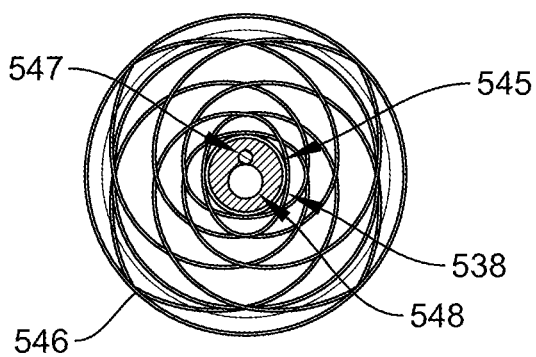
FIG. 21D        FIG. 21E

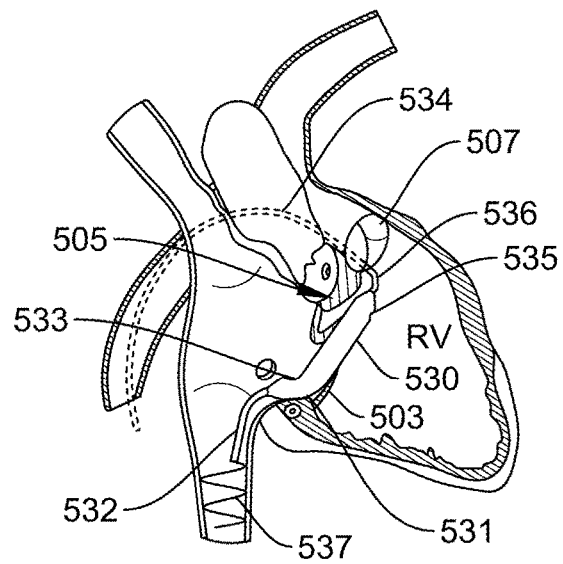 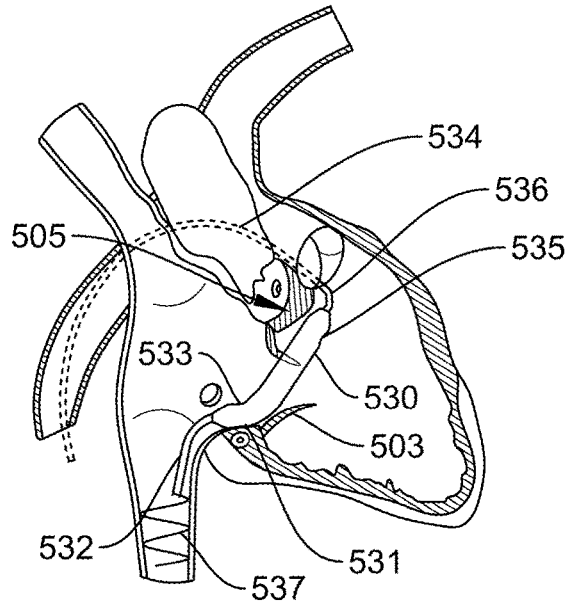
FIG. 21F   FIG. 21G
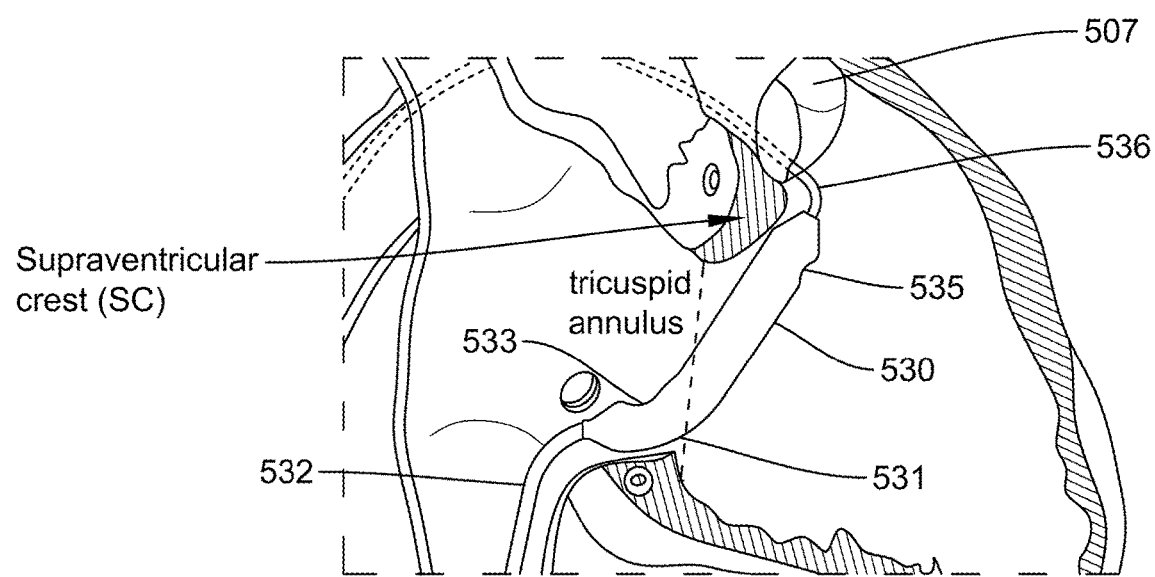
FIG. 21H

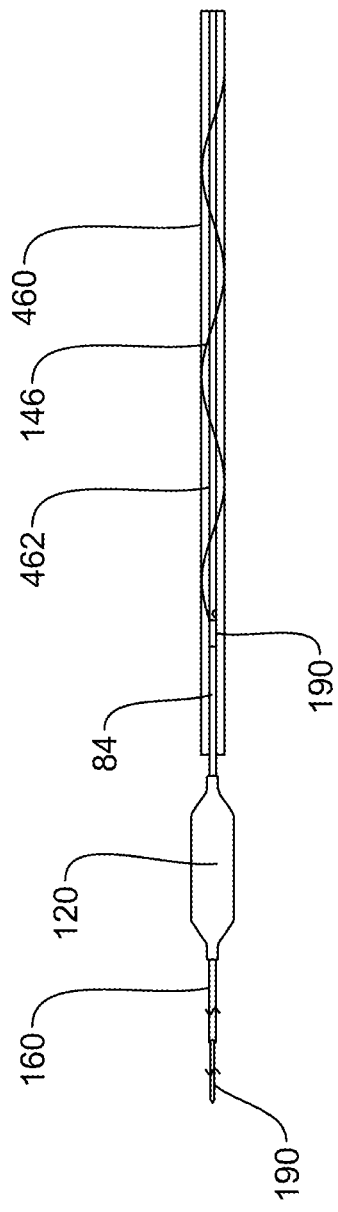
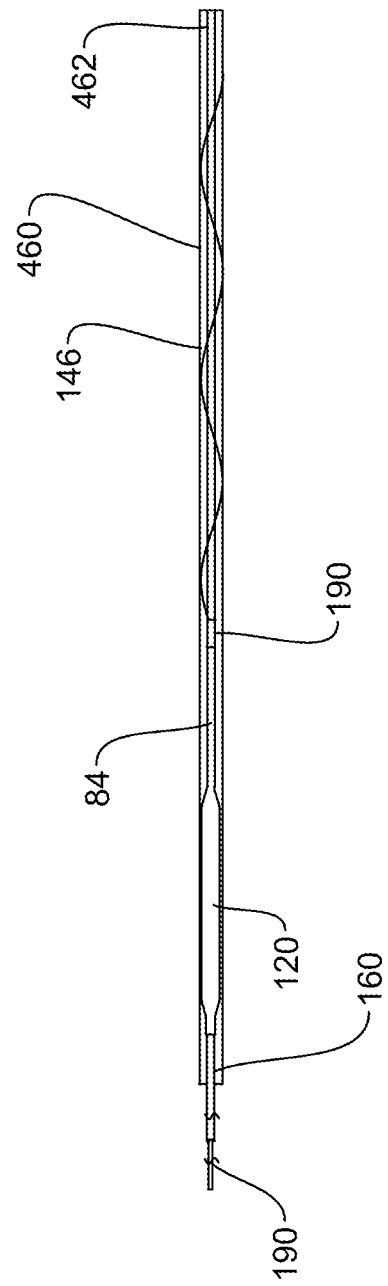

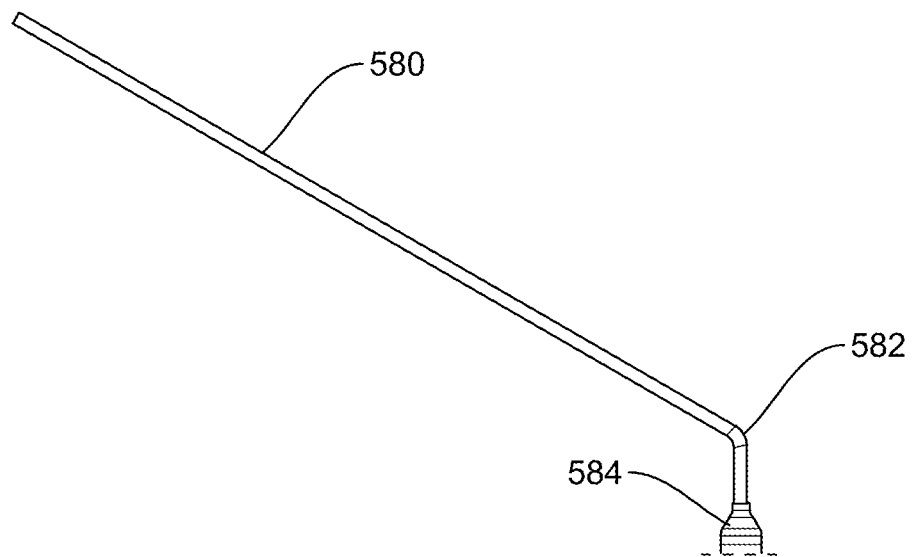
FIG. 25A
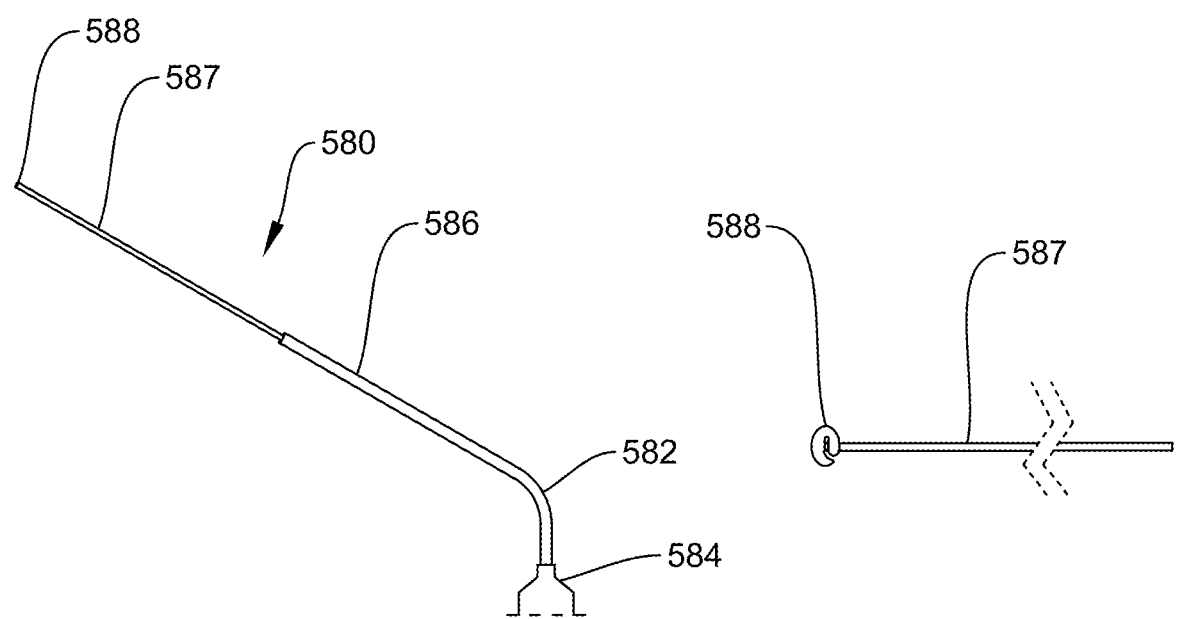
FIG. 25B
FIG. 25C

SECTION G-G
Proximal Section view

SECTION H-H
Distal Section view

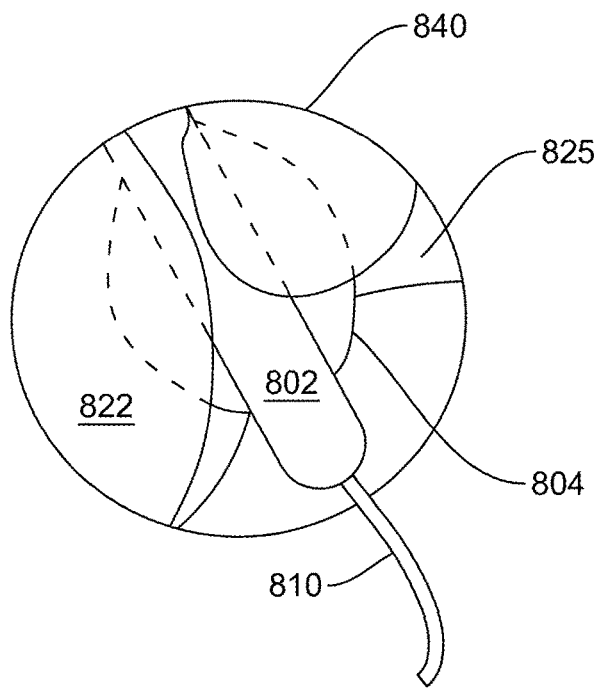
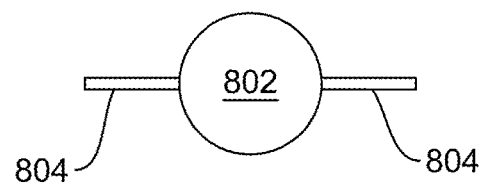
FIG. 40A          FIG. 40B
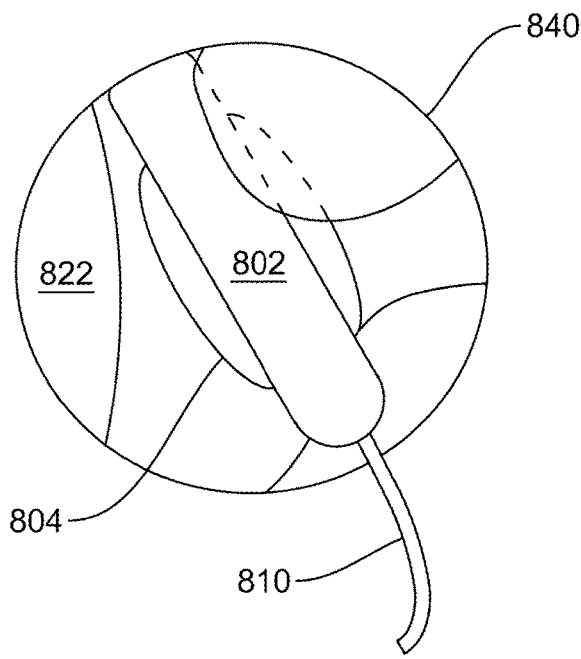
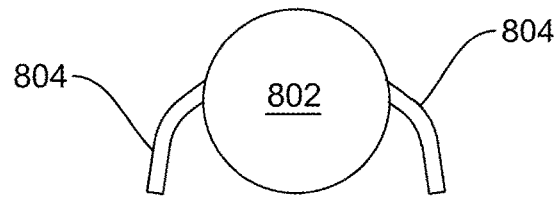
FIG. 41A          FIG. 41B

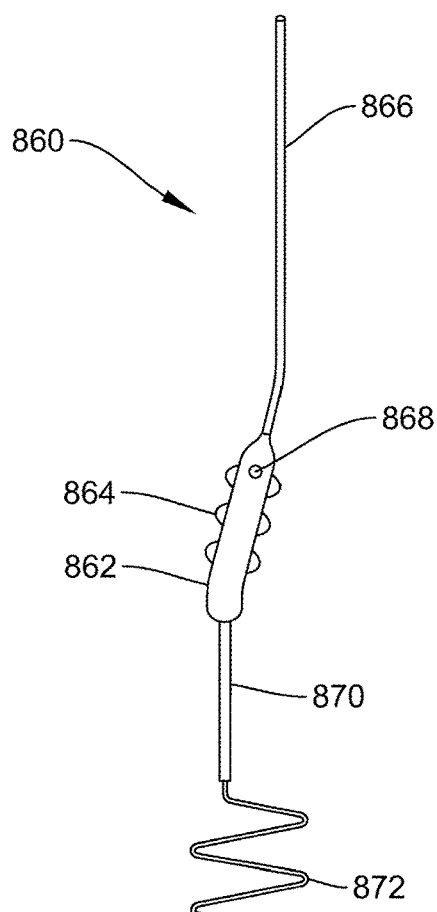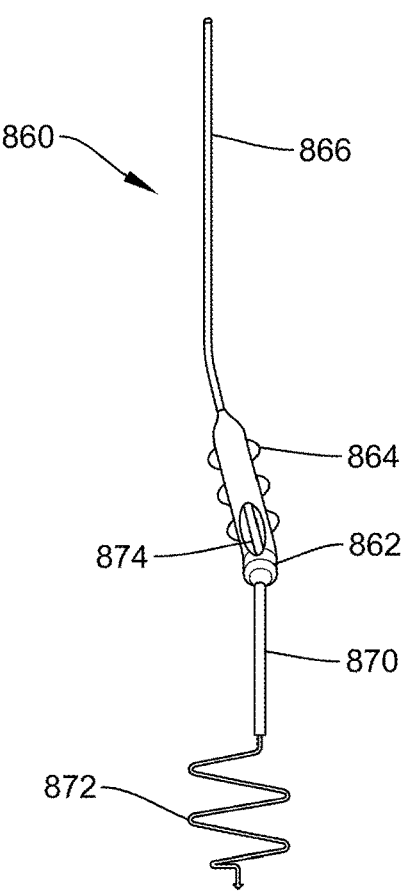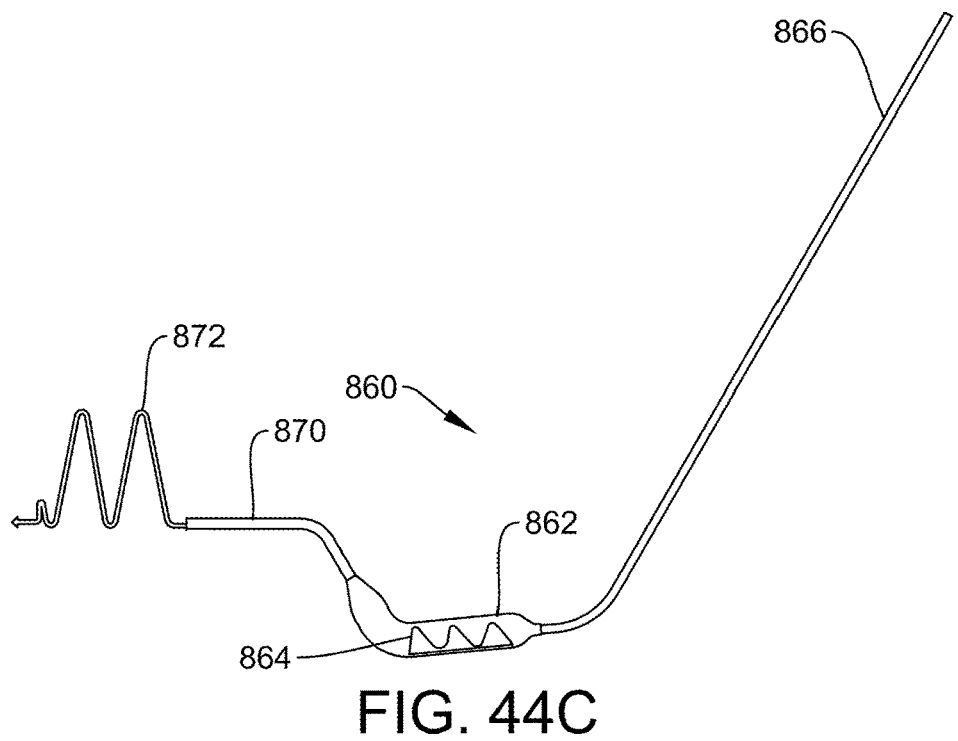

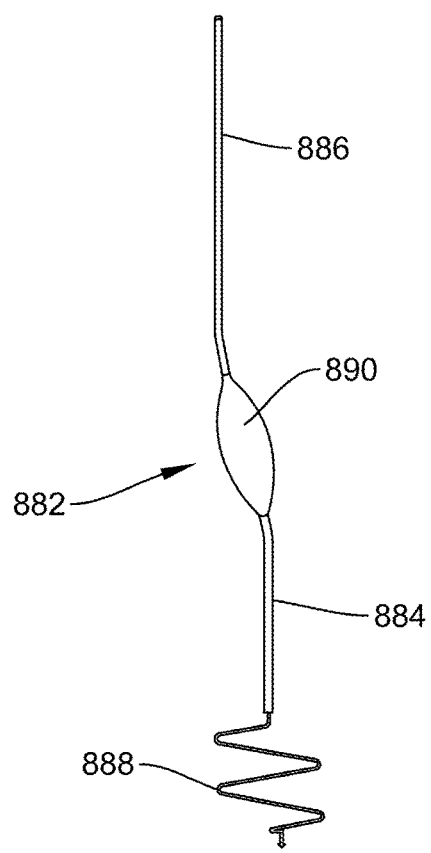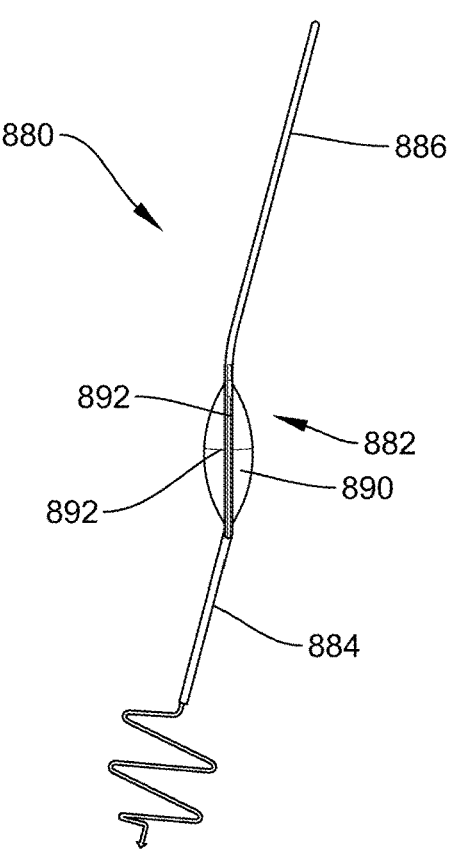
FIG. 45A   FIG. 45B
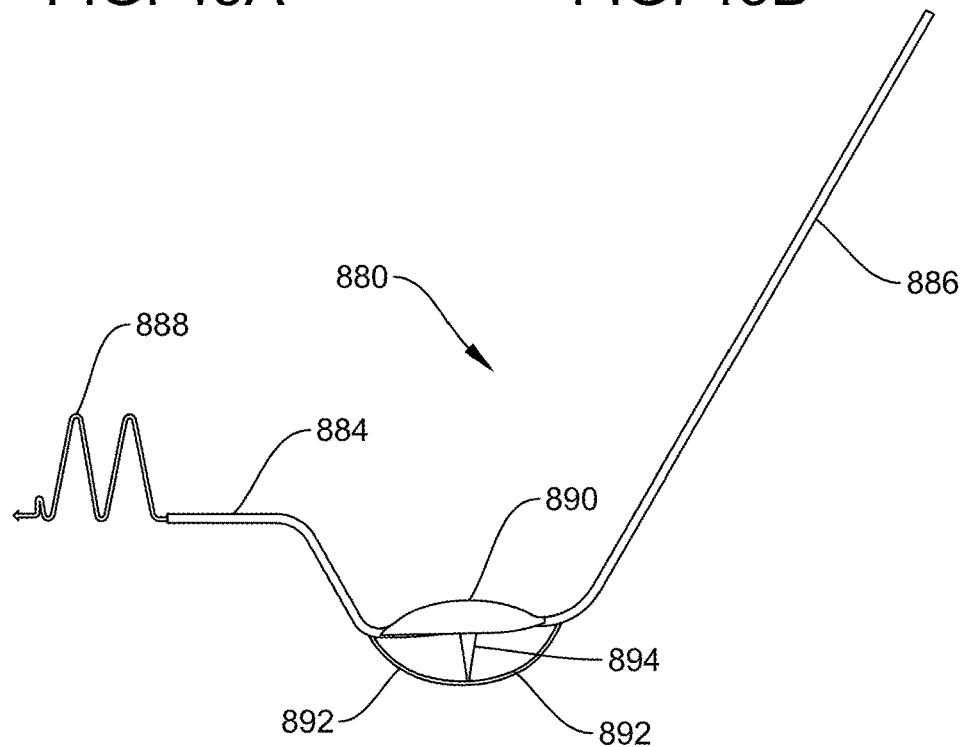
FIG. 45C

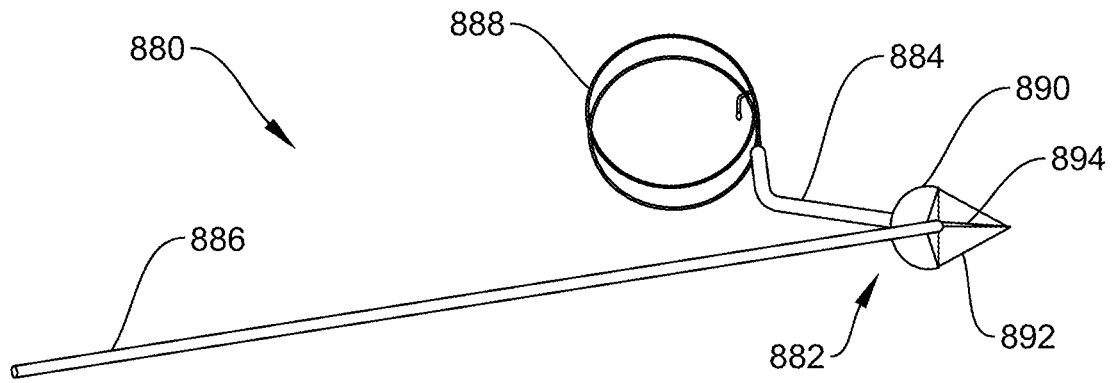
FIG. 46
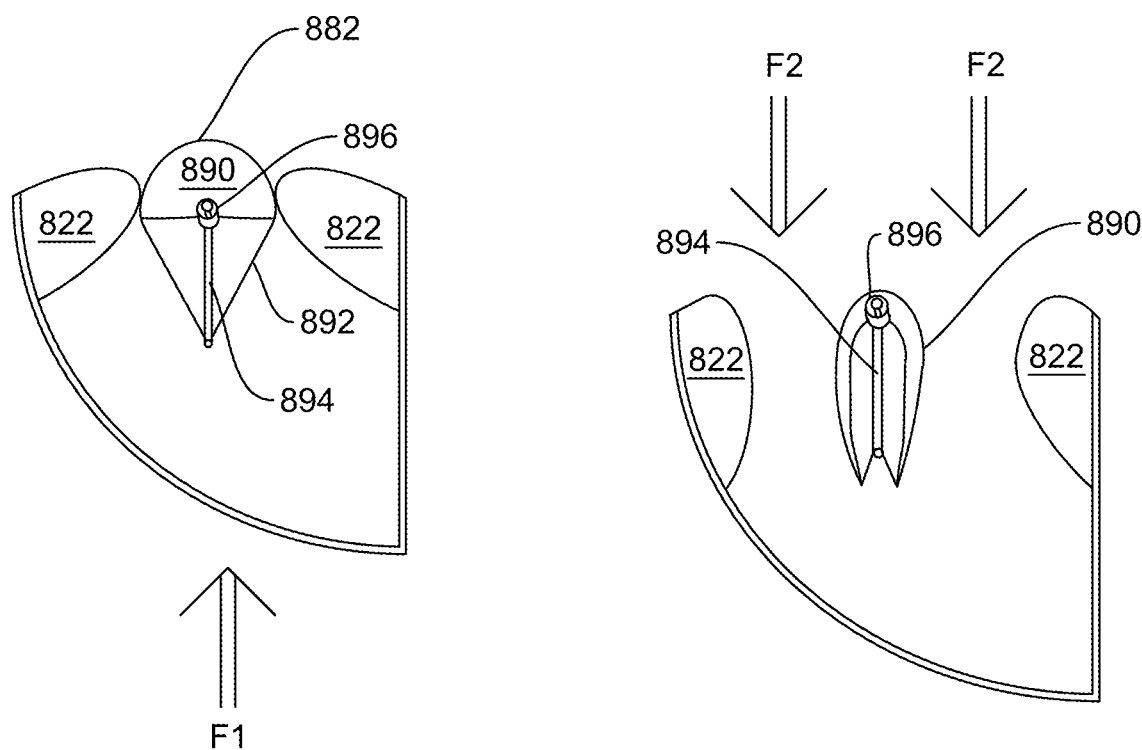
FIG. 47A
FIG. 47B

TRANSCATHETER DEVICE FOR TREATING TRICUSPID VALVE REGURGITATION

TECHNICAL FIELD

The present invention relates to the treatment of tricuspid valve regurgitation by using a transcatheter device.

BACKGROUND

Heart valve regurgitation (leakage through a heart valve) occurs when a heart valve fails to close properly. One example is tricuspid valve regurgitation, which is typically caused by changes in the geometric configurations of the right ventricle, papillary muscles, and tricuspid valve annulus. These geometric alterations result in incomplete leaflet coaptation during ventricular systole, thereby producing regurgitation. In the past, repairing heart valves required open-heart surgery with cardiopulmonary bypass. In recent years, a variety of catheter-based techniques for valve repair are being introduced. These catheter-based procedures do not require opening the chest or the use of cardiopulmonary bypass. There is need for further advancement in catheter-based treatments for tricuspid valve regurgitation.

SUMMARY

TRANSCATHETER DEVICE: In one aspect, this invention is a transcatheter device comprising a main shaft, a proximal portion, a distal tail, and a spacer body mounted on the main shaft and located between the proximal portion and the distal tail. This transcatheter device could be used for treating tricuspid valve regurgitation in a patient's heart. All or part of the transcatheter device is supported by the main shaft. The spacer body is mounted on the shaft, which travels through the spacer body. The proximal portion of the transcatheter device encompasses a proximal segment of the main shaft. This could be expressed alternatively as the proximal segment of the main shaft comprising the proximal portion of the transcatheter device. The distal tail of the transcatheter device encompasses a distal segment of the main shaft. This could be expressed alternatively as the distal segment of the main shaft comprising the distal tail of the transcatheter device.

The main shaft comprises a lumen and opening(s) for admitting a guidewire therethrough. There could be an opening for the lumen at the distal tip of the main shaft (in the distal tail part). There could also be a proximal opening located at the proximal portion of the transcatheter device. In embodiments where the transcatheter device comprises an intravascular anchor, this proximal opening for the lumen could be located between the spacer body and the intravascular anchor. For example, the opening could be located at the proximal end of the main shaft where it joins the intravascular anchor.

The total length of the main shaft could be in the range of 50-175 cm long. The main shaft may be constructed in any suitable way. For example, it could be made of a metal wire core (e.g. stainless steel or nitinol alloy), which is then covered the a polymer material. For example, the metal wire core could be covered with thermoplastic polyurethane braiding or polytetrafluoroethylene (PTFE) coating. The metal wire core could extend through the full length of the main shaft. However, in some embodiments, the metal wire core terminates before reaching the tip of the distal tail (or distal tip of main shaft). For example, the metal wire core could terminate at a location that is within 0.5-4 cm of the distal tip.

Distal Tail. The distal tail may have any suitable length to provide sufficient anchoring within the pulmonary artery. In some embodiments, the length of the distal tail is 10-40 cm long; and in some cases, 15-30 cm long. The distal tail could have a pigtail or rounded tip to blunt the tip and reduce trauma as it travels into pulmonary artery. In some embodiments, the distal tail has one or more bends. The bend(s) could have an inner angle in the range of 80-140°. The bends(s) could be located at any suitable location on the distal tail. In some embodiments, there is a bend located at a distance of 0.25-3.5 cm from the spacer body.

The distal tail may have a non-constant diameter over its length. In some embodiments, the distal tail comprises a proximal segment and a distal segment. The proximal segment may encompass 10-60% of the total length of the distal tail. The distal segment could have a thinner diameter than the proximal segment. There may be various reasons for this difference, such as the proximal segment having more or thicker sheathing or covering than the distal segment. The distal segment could be more flexible than the proximal segment of the distal tail. In some embodiments, the distal tail does not comprise any coil, loop, or stent.

The distal tail could be designed to have a streamlined shape. In some embodiments, the distal tail is a thin elongate cylinder shape (with or without a lumen) with no protruding features, such as hooks, wires, rings, ridges, etc. This may be useful in preventing thrombus formation or erosion of the distal tail into the wall of the pulmonary artery.

In some embodiments, the distal segment is more flexible than the proximal segment. In some cases, the proximal segment comprises a metal braiding, whereas the distal segment does not. The distal segment could comprise a polymer material that is softer than the proximal segment. The distal segment could have a smaller diameter than the proximal segment. In some cases, the length of the distal segment is shorter than the length of the proximal segment. The length of the distal segment could be 2-7 cm long. The length of the proximal segment could be 7-15 cm long. In some cases, the proximal segment constitutes 35-65% of the total length of the distal tail.

The proximal segments could have a different size than the distal segment. In some cases, the distal segment has a smaller diameter than the proximal segment. In some cases, the diameter of the distal segment is 45-85% of the diameter size of the proximal segment. For example, the distal segment could have a diameter of 2-5 mm, whereas the proximal segment could have a diameter of 3-6 mm.

In some cases, the distal tail further comprises a middle segment between the proximal segment and the distal segment. The middle segment is more flexible than the proximal segment but is stiffer than the distal segment. In some cases, the length of the middle segment is shorter than the length of the proximal segment. For example, the length of the middle segment could be 2-7 cm long.

Spacer Body. The spacer body is mounted on the main shaft. The spacer body is made to have dimensions or shape suitable for providing a coaptation surface for leaflets of the tricuspid valve. For example, the shape of the spacer body may have a particular design. In some embodiments, the spacer body has a linear shape (e.g. ovoid, cylindrical with tapered or conical ends, etc.). In some embodiments, the spacer body has a non-linear shape (e.g. curved or boot-shaped). In a non-linear shaped spacer body, the spacer body could comprise a bend having an inner angle in the range of 80-140°.

Another design parameter is the length of the spacer body. For example, the spacer body could be 4-13 cm long; and in some cases, 5-9 cm. In cases where the spacer body has a non-linear shape, this length is represented by the travel distance along the longitudinal axis of the spacer body. The width of the spacer body can be measured on a transverse cross-section plane that is orthogonal to the longitudinal axis. In some embodiments, the widest width of the spacer body on this transverse cross-section plane is in the range of 0.5-3.5 cm; and in some cases, in the range of 0.5-2.5 cm. The spacer body may have a relaxed contracted configuration and an elongated configuration. In this situation, the measurements above for the spacer body are made in the relaxed configuration. In some embodiments, the width of the spacer body on the widest axis is greater than the width of the spacer body on its cross-axis on the transverse plane (i.e. non-circular or asymmetric cross-section).

The spacer body can have any suitable structure, such as balloon (e.g. fluid, foam, or air-filled), basket, mesh, struts (e.g. like a stent), framework, skeleton, scaffolding, etc. If needed, a surface for the spacer body may be provided in any suitable manner, such as a skin, shell, casing, or membrane. The spacer body may be made of any suitable material, such as plastics, metals, or combinations thereof. The spacer body could have one or more openings to allow the flow of blood therethrough. There may be a gap between the spacer body (at one of its ends) and the main shaft to allow the flow of blood therethrough. These openings or gaps allows blood to flow easily through the spacer body, which may be useful for preventing thrombus formation.

In some embodiments, the spacer body comprises one or more side appendages. These may be located on a lateral side of the spacer body. The side appendage can be any type of thin and flexible structure that enhances the function of the spacer body as a barrier against the flow of blood across gaps in the tricuspid valve leaflets. Examples of side appendages include wings, flaps, shrouds, drapes, skirts, free edges, tags, etc. The side appendage has a widened configuration (for ventricular systole) and a narrowed configuration (for ventricular diastole).

The widened configuration for the side appendage is induced by the direction of blood flow and could be performed in any suitable manner, such as spreading out, extending out, enlarging, distending, folding out, opening, etc. The narrowed configuration for the side appendage is induced by the other direction of blood flow and could be performed in any suitable manner, such as folding in, retracting, collapsing, shrinking, closing, etc.

The side appendage should be sufficiently wide to reduce gaps between the tricuspid valve leaflets or help stabilize the spacer body across the tricuspid valve. In some embodiments, the width of the side appendage is 0.3-5.0 cm; and in some cases, 0.5-3.5 cm. The width is measured as the widest distance for the side appendage from spacer body in a direction that is orthogonal to the transverse axis of the spacer body.

The length of the side appendage may be shorter than the length of the spacer body. In some embodiments, the length of the side appendage is 2-9 cm; and in some cases, 4-7 cm. The length is the longest length as measured along the longitudinal axis of the spacer body.

The side appendage should be sufficiently thin to be flexibly responsive to blood flow across the tricuspid valve. In some embodiments, the side appendage has a thickness of 0.2-10 mm; and in some cases, 0.3-6 mm. The thickness is measured along a transverse axis of the spacer body that is orthogonal to the side appendage and the longitudinal axis of the spacer body.

The side appendage can have any suitable shape. In some embodiments, the side appendage has a non-flat shape with a three-dimensional curvature that gives the side appendage an inner side (concave) and an outer side (convex). Having this non-flat shape may be useful for improving the response to blood flow across the tricuspid valve.

Proximal Portion. The proximal portion of the transcatheter device comprises the proximal segment of the main shaft. The proximal segment could be a proximal continuation of the main shaft. The proximal portion of the transcatheter device could have any suitable length to provide intravascular access or sufficient anchoring within the vena cava. In some embodiments, the total length of the proximal portion is in the range of 10-60 cm long. In embodiments where the proximal portion includes an intravascular anchor, this measurement includes the length of the intravascular anchor. In situations where the intravascular anchor does not have a linear shape (e.g. coil), this means the length as measured along the longitudinal axis.

In some embodiments, the proximal segment of the main shaft has one or more bends. The bend(s) could have an inner angle in the range of 80-140°. The bends(s) could be located at any suitable location on the proximal segment of the main shaft. In some embodiments, there is a bend located at a distance of 0.25-5.5 cm from the spacer body. The proximal segment could also have a curved portion (wider than a bend). In some embodiments, the proximal segment has two separate bends and a curved portion between the two bends. The length of the proximal segment could be in the range of 3-15 cm long.

Intravascular Anchor. In some embodiments, the proximal portion comprises an intravascular anchor. Examples of intravascular anchors include spiral coil and expandable stent. In some embodiments, the intravascular anchor is a spiral coil. The spiral coil could have at least two spirals. The intravascular anchor could have any suitable width for anchoring in the vena cava. In some embodiments, the widest width of the intravascular anchor is in the range of 2-7 cm wide. The length of the intravascular anchor could be in the range of 4-11 cm long (as measured straight on its longitudinal axis). In situations where the intravascular anchor does not have a linear shape (e.g. coil), this means the length as measured along the longitudinal axis. In situations where the intravascular anchor has flexible configurations (e.g. as in a helical coil), this length is measured in its naturally coiled configuration. In an alternate embodiment of this invention, the transcatheter device comprises either the intravascular anchor or the distal tail, but not both.

Radiopaque Markers. The transcatheter device may have one or more radiopaque markers that are visible under x-ray imaging (e.g. x-ray fluoroscopy). In some embodiments of the transcatheter device, there is a first radiopaque marker that is located on the proximal segment of the main shaft (proximal to the spacer body), and a second radiopaque that is located on the distal tail (distal to the spacer body). The first radiopaque marker could be located within 2 cm of the proximal end of the spacer body. The second radiopaque marker could be located within 2 cm of the distal end of the spacer body.

COAPTATION ASSEMBLY: In another aspect, this invention is a coaptation assembly for treating tricuspid valve regurgitation. The assembly comprises a transcatheter device of the invention. The assembly further comprises a guidewire traveling through the lumen of the main shaft. In some embodiments, the assembly further comprises a moveable delivery sheath that can cover the spacer body or intravascular anchor. The sheath could be advanced to cover the spacer body or intravascular anchor. Or the spacer body could be retracted to uncover the spacer body or intravascular anchor. In some embodiments, the assembly further comprises a deployment catheter. The deployment catheter is sufficiently long to deploy the transcatheter device in the patient's heart. For example, the deployment catheter could be 50-150 cm long.

COAPTATION KIT: In another aspect, this invention is a coaptation kit for treating tricuspid valve regurgitation. The kit comprises a transcatheter device of the invention, a deployment catheter, a delivery sheath, and a guidewire. These components could be assembled or used in the manner described herein.

METHOD OF TREATMENT: In another aspect, this invention is a method of treating a defective tricuspid valve in a patient using a transcatheter device of this invention. The transcatheter device is implanted with the distal tail within the pulmonary artery and the spacer body across the tricuspid valve. The transcatheter device is inserted into an entry vein, such as the femoral, subclavian, or jugular vein. The transcatheter device is advanced further into the vena cava (inferior or superior). The transcatheter device is advanced through a right atrium of the heart, across the tricuspid valve, and into a right ventricle of the heart. The transcatheter device is further advanced towards the pulmonary artery. The distal tail is advanced into the pulmonary artery. This could be the left-side or right-side pulmonary artery.

The distal tail works to help anchor the transcatheter device. As such, the distal tail may extend into the pulmonary artery of sufficient distance to perform this function. In some embodiments, the distal tail extends for a distance of at least 10 cm into the pulmonary artery; and in some cases, at least 15 cm. In some embodiments, the distal tail is advanced past a first branching point of the pulmonary artery; in some cases, past a second branching point of the pulmonary artery; and in some cases past a third branching point of the pulmonary artery. Proper positioning of the distal tail could be confirmed by having a radiopaque marker and x-ray imaging to see the radiopaque marker. In some embodiments, the distal tail is not embedded within heart tissue.

The spacer body should be properly positioned between leaflets of the tricuspid valve. This proper placement could be confirmed by external imaging such as x-ray or echocardiogram. In some embodiments, the spacer body is positioned to abut against a supraventricular crest of the heart. This abutment against the supraventricular crest could occur at a location within the distal half of the spacer body. The tricuspid valve has a tricuspid annulus and there is an annular plane defined for the tricuspid annulus. This annular plane is along an x-axis of the tricuspid annulus and orthogonal to a Y-axis of the tricuspid annulus. In some embodiments, the spacer body is positioned at an oblique angle (<90°) relative to the annular plane. This oblique angle could be in the range of 15-75°.

In embodiments where the spacer body comprises a side appendage, the method could further comprise widening the side appendage during ventricular systole and narrowing the side appendage during ventricular diastole. In the widened configuration, the side appendage may be positioned between leaflets of the tricuspid valve and obstruct gaps that exist therein. In situations where the side appendage has a non-flat shape, the inner side (concave) is oriented to face towards the right ventricle.

In embodiments where the transcatheter device further comprises an intravascular anchor at its proximal portion, this intravascular anchor is lodged in the vena cava (inferior or superior). The transcatheter device could be implanted using a guidewire. The guidewire is inserted into an entry vein, such as the femoral vein and advanced further into the vena cava (inferior or superior). The guidewire is advanced through the right atrium of the heart, across the tricuspid valve, and into the right ventricle of the heart. The guidewire is further advanced towards the pulmonary artery. The guidewire is inserted into a guidewire lumen of the transcatheter device and the transcatheter device is advanced over this guidewire.

Deployment. The transcatheter device could be deployed using a delivery sheath and deployment catheter. During insertion, the delivery sheath could be moved to cover the spacer body, and for relevant embodiments, cover the intravascular anchor. During deployment the delivery sheath is retracted backwards. Retraction of the delivery sheath and unsheathing components of the transcatheter device could be part of the implantation process. In embodiments where the spacer body is self-expanding, this unsheathing could allow the spacer body to self-expand outward to provide a wider coaptation surface. In embodiments where the transcatheter device comprises an intravascular anchor having an expandable configuration, unsheathing allows the anchor to expand outward to lodge within the vena cava.

In some embodiments, this deployment assembly is not disassembled immediately after the procedure is completed. The clinician may wish to implement a short trial period to confirm the effectiveness of the device. For this short trial period, one or more components of the delivery assembly (deployment catheter, delivery sheath, or guidewire) could be retained inside the patient's body, along with the transcatheter device. During the short trial period, the tricuspid valve function is monitored (e.g. by echocardiogram). If the transcatheter device shows effectiveness during this trial period, the deployment assembly is removed, but retaining the transcatheter device in place. If the trial period shows ineffective results, having the deployment assembly still-in-place allows easy removal of the transcatheter device. The trial period could be any suitable short duration. For example, the trial period could be a duration that is within the range of 12-48 hours post-insertion.

Retrieval. After being implanted, the transcatheter device could be removed if needed. This can be done by grasping the intravascular anchor (e.g. spiral coil at its proximal tip) and pulling out the transcatheter device for removal from the patient's body. For example, this could be performed by inserting a snare catheter through an entry vein, advancing the snare catheter towards the spiral coil, grasping the spiral coil, withdrawing the snare catheter, and pulling out the transcatheter device from the entry vein.

BRIEF DESCRIPTION OF THE DRAWINGS

FIGS. 4A and 4B show a transcatheter device of as implanted in the patient's heart.

FIGS. 10A-10C show how a transcatheter device is deployed using a delivery sheath.

FIGS. 21A-E show various views of another embodiment of a transcatheter device. FIGS. 21F-H show the transcatheter device implanted in the heart.

FIGS. 23A and 23B show another view of a delivery assembly.

FIGS. 25A-C show different embodiments of the distal tail.

FIG. 39 and FIGS. 40A and 40B show how the wings could work to improve coaptation of the spacer body to the tricuspid valve leaflets. FIGS. 41A and 41B show how the wings fold inward.

FIGS. 44A-C show another example of a transcatheter device with multiple smaller winglets on the spacer body.

FIGS. 45A-C show another example of a transcatheter device with a different design for the spacer body.

FIG. 46 is a perspective view of the transcatheter device showing the spacer body in deployed configuration.

FIGS. 47A and 47B are illustrations of the tricuspid valve shown as a schematic model from a side view with the spacer body installed therein.

DETAILED DESCRIPTION OF EXAMPLE EMBODIMENTS

To assist in understanding the invention, reference is made to the accompanying drawings to show by way of illustration specific embodiments in which the invention may be practiced. The drawings herein are not necessarily made to scale or actual proportions. For example, lengths and widths of the components may be adjusted to accommodate the page size.

Figure 1:
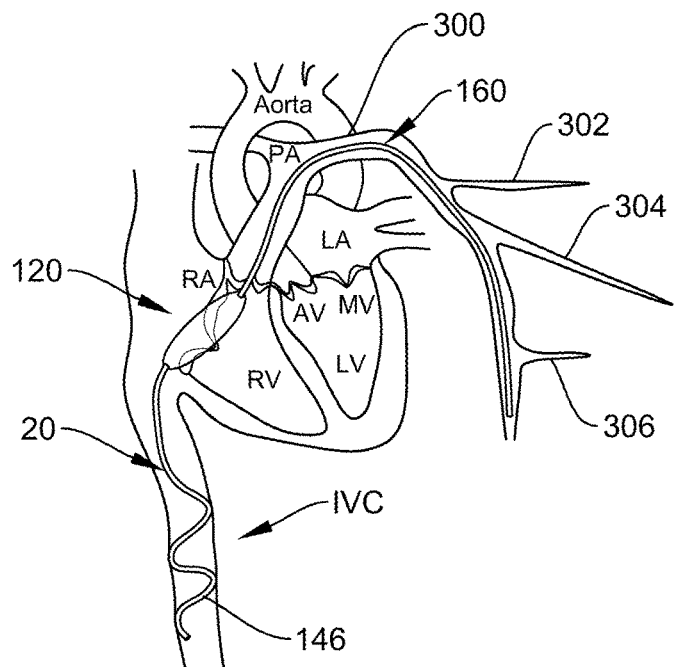
FIG. 1 shows an example of a transcatheter device for treating tricuspid regurgitation.

FIG. 1 shows an example of a transcatheter device for reducing tricuspid regurgitation. Shown here is a transcatheter device 100 as implanted in the patient's heart. The transcatheter device 100 has a distal tail 160 and a proximal portion 20. In between the distal tail 160 and the proximal portion 20 is a spacer body 120. The proximal portion 20 of the transcatheter device 100 comprises a spiral coil 146. The spacer body 120 works to provide improved coaptation of the tricuspid valve leaflets, thereby reducing valve regurgitation. The spiral coil 146 works to lodge inside the inferior vena cava (IVC) to provide an anchor for maintaining the desired position of the spacer body 120 across the tricuspid valve. The distal tail 160 works to lodge within the pulmonary artery (PA) to also provide an anchor for maintaining the desired position of the spacer body 120 across the tricuspid valve.

Figure 2:
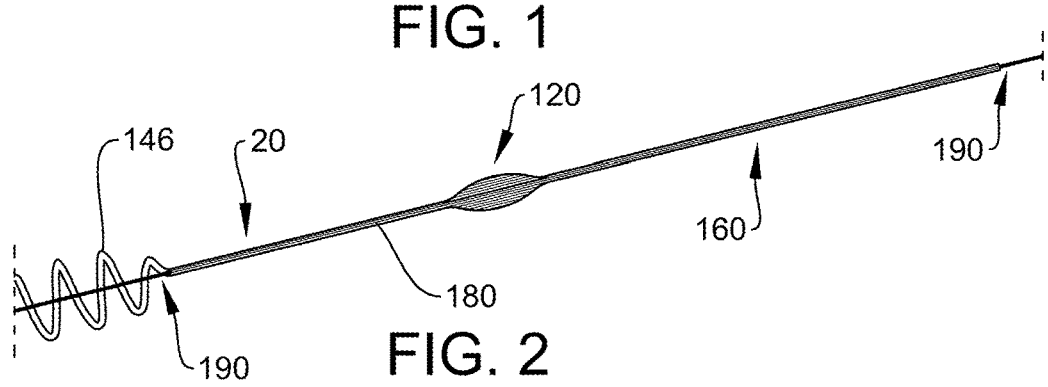
FIG. 2 shows a transcatheter device in isolation and in an extended, stretched-out configuration.

FIG. 2 shows the transcatheter device 100 in isolation and in an extended, stretched-out configuration. Transcatheter device 100 comprises a main shaft 180 that encompasses the proximal portion 20 of the transcatheter device 100, across spacer body 120, and the distal tail 160 of the transcatheter device 100. In this example embodiment, the spacer body 120 has a shape that is symmetric on both its longitudinal axis and its transverse axis. The shape resembles a football with a gradual longitudinal curvature and an enlarged belly in the middle portion.

The main shaft 180 has a lumen through which a guidewire 190 travels. The main shaft 180 has a proximal opening from which the lumen begins, and a distal opening at which the lumen ends. For implantation of the transcatheter device 100, a guidewire 190 is inserted into the femoral vein, advanced through the inferior vena cava, into the right atrium of the heart, across the tricuspid valve, into the right ventricle, and then into the pulmonary artery.

Once the guidewire 190 is set in position, the transcatheter device 100 is advanced over the guidewire 190 by inserting the guidewire 190 through the proximal opening of the main shaft 180, through the lumen of the main shaft 180, and out of the distal opening. Traveling along guidewire 190, the transcatheter device 100 is advanced through the inferior vena cava, into the right atrium of the heart, across the tricuspid valve, into the right ventricle, and then into the pulmonary artery. When the transcatheter device 100 is fully implanted, the spiral coil 146 is lodged inside the inferior vena cava, the distal tail 160 is lodged within the pulmonary artery, and the spacer body 120 is placed across the tricuspid valve. For visualization under x-ray fluoroscopy, the distal tail 160 may further include a radiopaque marker band having a size of 1 mm from the distal tip. The distal tail 160 is made of a nitinol wire core that is reinforced with Pellethane 55D (medical-grade thermoplastic polyurethane elastomer) braiding.

Figure 3:
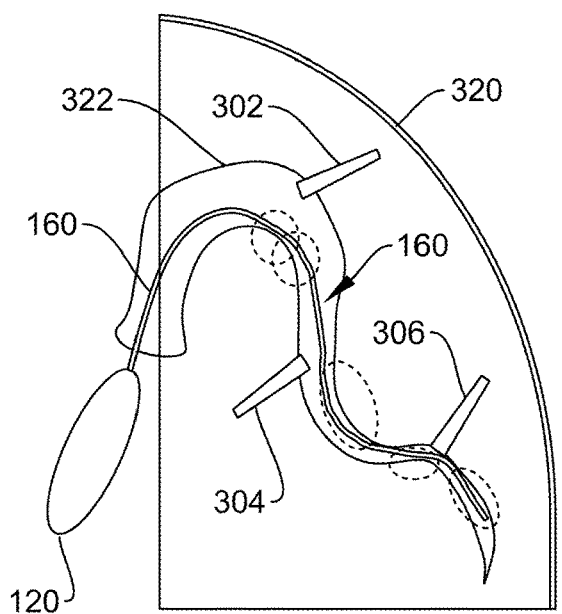
FIG. 3 shows the left-side lung with the pulmonary artery tree made visible.

Distal Tail: In this example embodiment, the distal tail 160 of the transcatheter device 100 is advanced over the guidewire 190 and extended into a pulmonary artery to function as an anchor as shown in FIGS. 1 and 3. In FIG. 1, the distal tail 160 extends into the left-side pulmonary artery 300 at a location that is past a first artery branch 302, past a second artery branch 304, and past a third artery branch 306. Similarly, FIG. 3 shows the left-side lung 320 with the pulmonary artery tree made visible. Shown here is the main trunk 322 of the left pulmonary artery and branching arteries 302, 304, and 306. The distal tail 160 of the transcatheter device 100 goes into the pulmonary artery main trunk 322 and extends past the first branching artery 302, past the second branching artery 304, and past the third branching artery 306.

Here, the distal tail 160 is not embedded into the tissue of the pulmonary artery. Instead, the distal tail 160 is trapped in the pulmonary artery because it is entangled by the naturally tortuous anatomy of the pulmonary artery tree. The dashed circles indicate the multiple points of contact along the path of the distal tail 160 through the pulmonary artery. The distal tail 160 becomes entangled within the pulmonary artery at these multiple contact points. Thus, the distal tail 160 resists being pulled retrograde and serves as an anchor to keep the transcatheter device 100 from being pulled away from positioning of spacer body 120 across the tricuspid valve.

In an alternate embodiment of the transcatheter device 100, it may have only one anchoring member. It could have either the spiral coil 146 for anchoring in the inferior vena cava, or it could have distal tail 160 for anchoring within the pulmonary artery. In another alternate embodiment of the transcatheter device 100, the distal tail 160 could be rela- tively short, extending only into the pulmonary artery trunk (left or right), but not extending past a first branching artery.

Systole & Diastole: FIGS. 4A and 4B show the transcatheter device of FIG. 2 as implanted in the patient's heart 290 (cross-section view) with the spacer body 120 positioned across the leaky tricuspid valve. The right atrium (RA) and right ventricle (RV) are labelled. In FIG. 4A, the heart 290 is in systolic contraction part of the cardiac cycle in which the tricuspid valve is in closed conformation. As seen here, the leaflets 292 of the tricuspid valve are pushed against the spacer body 120 (coaptation). This reduces regurgitation in the leaky tricuspid valve. FIG. 4B shows the tricuspid valve in diastolic relaxation part of the cardiac cycle. As seen here, the leaflets 292 of the tricuspid valve are pushed away from the spacer body 120 so that blood can flow around it. This allows blood to flow from the right atrium into the right ventricle so that it is refilled with blood for the next pumping cycle.

Figure 13A:
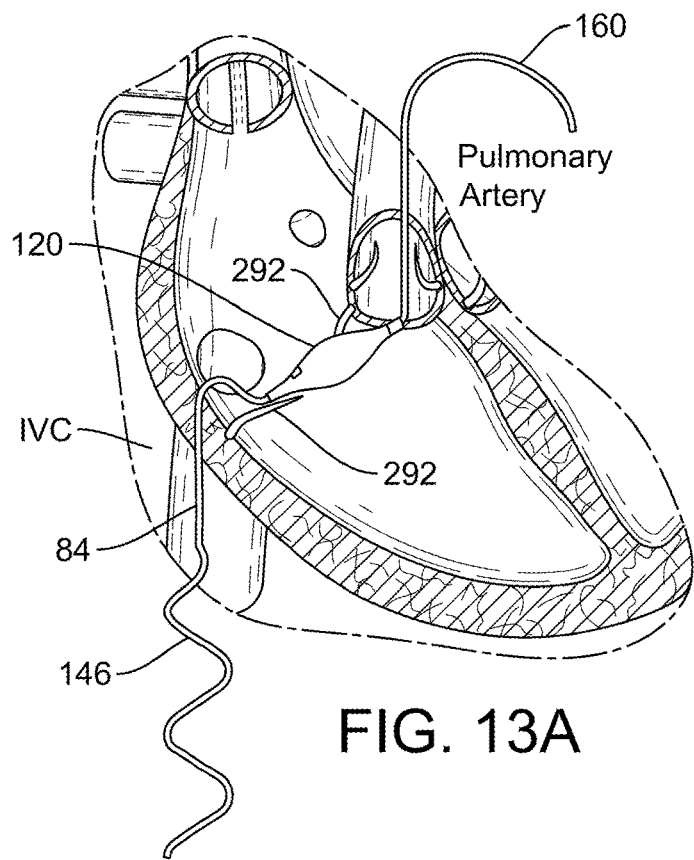
FIGS. 13A-D show another illustration of a transcatheter device of as implanted in the patient's heart.
Figure 13B:
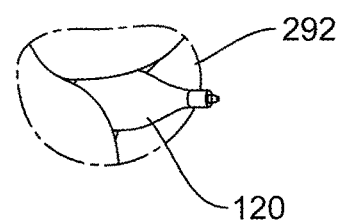
Figure 13C:
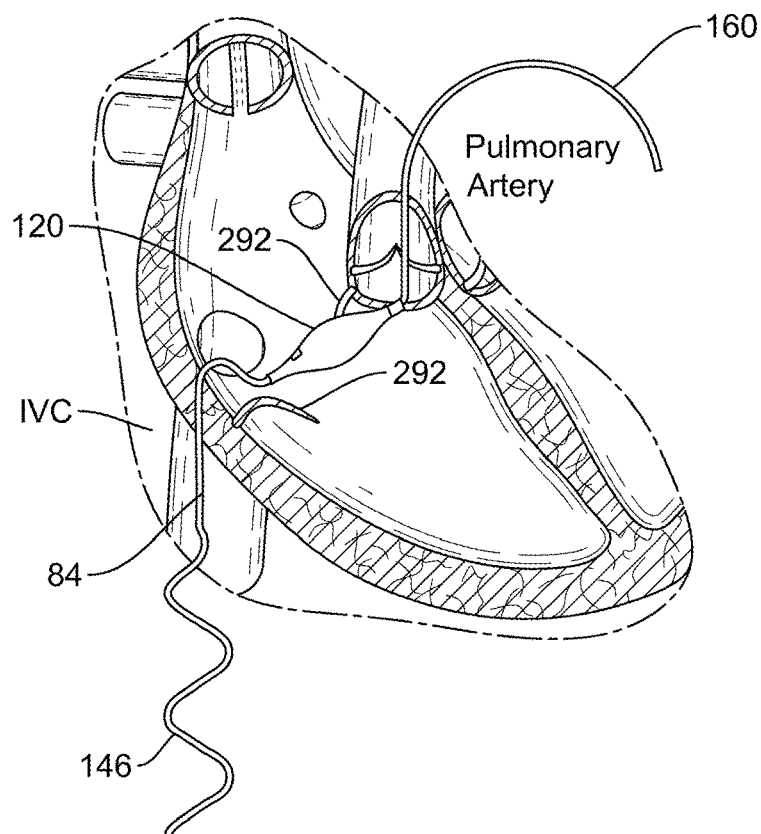
Figure 13D:
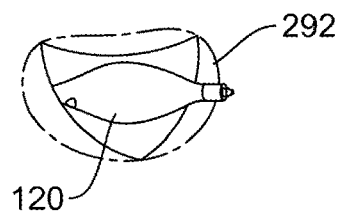

FIGS. 13A-13D show another illustration of the transcatheter device of FIG. 2 as implanted in the patient's heart 290 (cross-section view) with the spacer body 120 positioned across the leaky tricuspid valve. FIGS. 13A and 13B show the heart in systole with the tricuspid valve leaflets 292 closed around the spacer body 120. FIGS. 13C and 13D show the heart in diastole with the tricuspid valve leaflets 292 in open position. The tricuspid valve leaflets 292 are spread apart from the spacer body 120, thereby allowing blood flow around the spacer body 120.

Figure 5A:
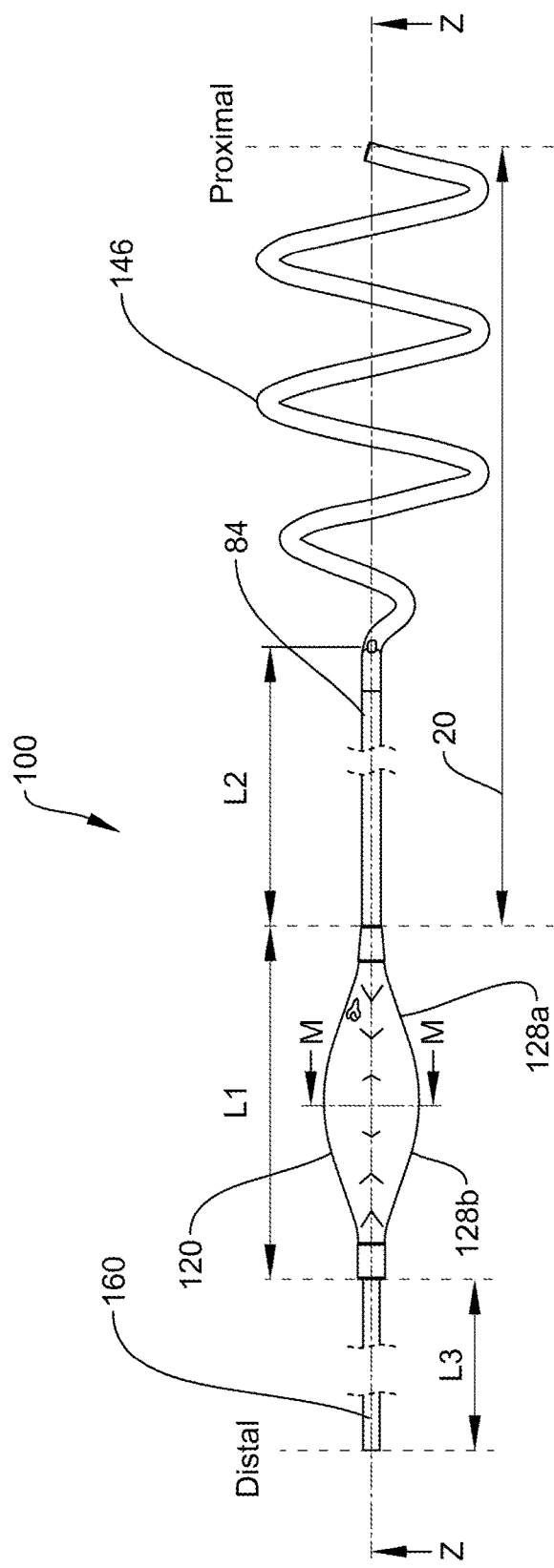
FIGS. 5A and 5B show a further detailed view of a transcatheter device.
Figure 5B:
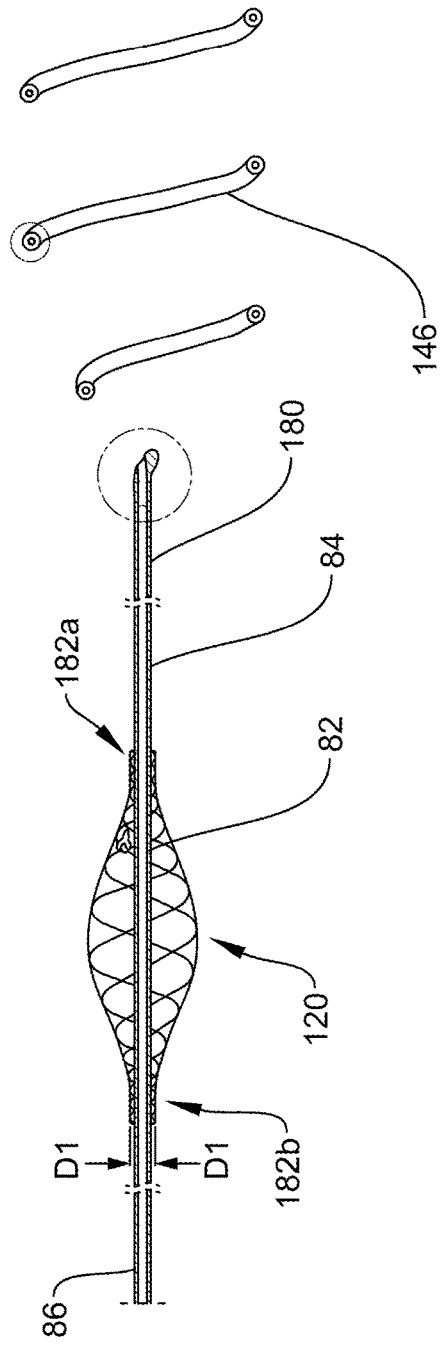

FIGS. 5A and 5B show a further detailed view of the transcatheter device 100 of FIG. 1 above. FIG. 5A shows that the spacer body 120 comprises two sleeves, a proximal sleeve 128a and a distal sleeve 128b. The line M-M indicates where the two sleeves meet. The two sleeves may move relative to each other such as being separated apart or being pushed together. For purposes of definition, this transcatheter device 100 can be considered as having a distal tail 160, a spacer body 120, and a proximal portion 20. FIG. 5B shows transcatheter device 100 in longitudinal cross-section view to reveal some of the internal features. As seen here, the transcatheter device 100 comprises a main shaft 180. The distal tail 160 can be considered as the distal segment 86 of this main shaft 180. The spacer body 120 is mounted on the middle portion 82 of the main shaft 180 in coaxial arrangement. The proximal end 182a of the spacer body 120 is fixed to the main shaft 180, whereas the distal end 182b is slidable on main shaft 180. This allows distal sleeve 128b to be shifted towards or away from proximal sleeve 128a. Alternatively, both the proximal end 182a and the distal end 182b of the spacer body 120 may be slidable on the main shaft 180. This would allow both proximal sleeve 128a and distal sleeve 128b to shift back-and-forth relative to each other.

The proximal portion 20 of transcatheter device 100 can be considered as further divided into the proximal segment 84 of the main shaft 180, and attached thereto is the spiral coil 146. Length L1 is 5 cm for the length of the spacer body 120. Length L2 is 9 cm for the length of the proximal segment 84 of the main shaft 180. Length L3 is the length of the distal tail 160 (and also the distal portion 86 of the main shaft 180. As shown by the paired arrows D1 the inner diameter of the distal end 182 is 3.3 mm.

Figure 7A:
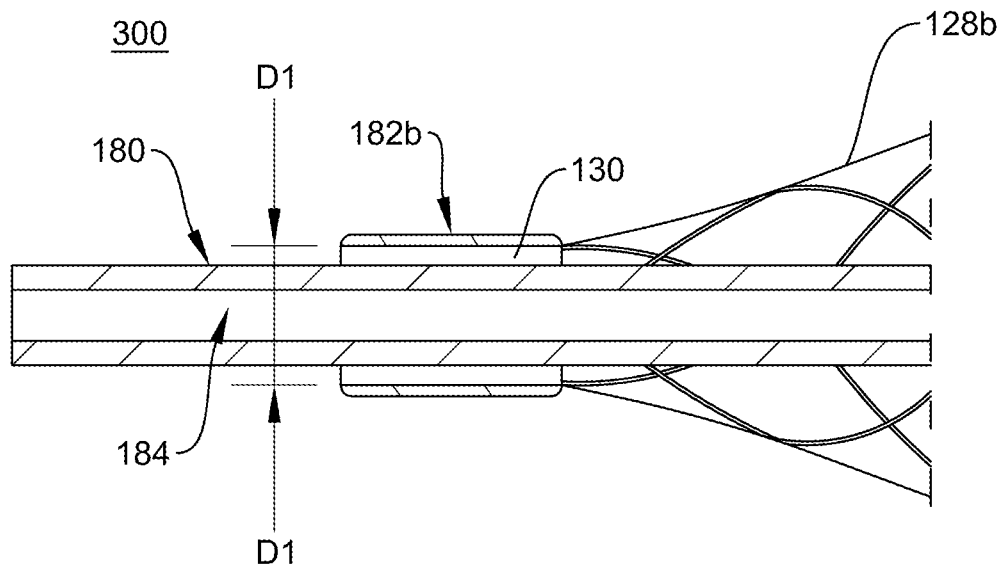
FIGS. 7A and 7B show close-up views of the distal end and distal sleeve of the spacer body.
Figure 7B:
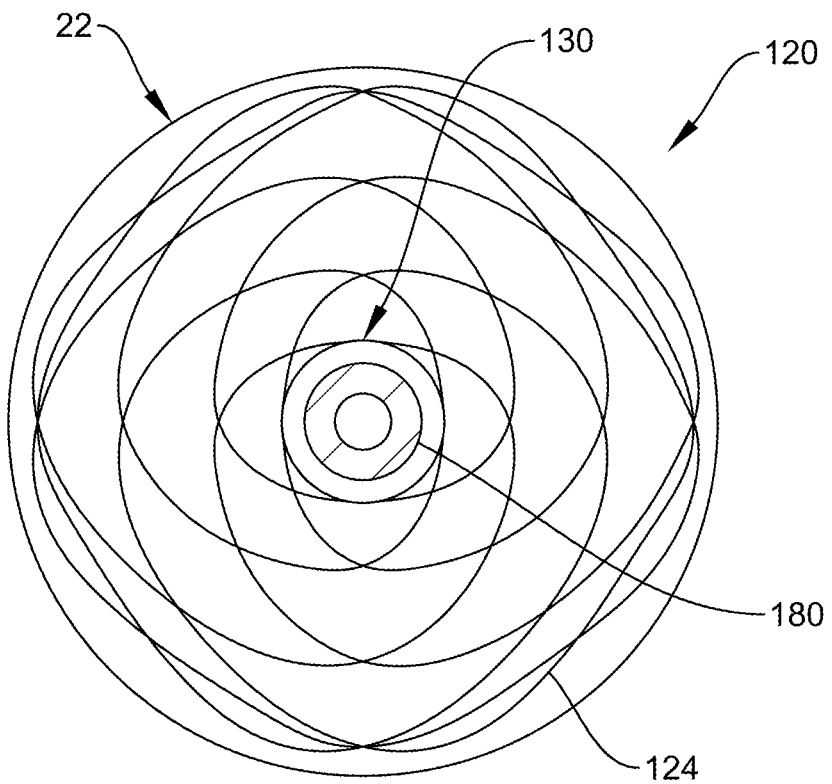

FIGS. 7A and 7B show close-up views of the distal end 182b and distal sleeve 128b of the spacer body 120 shown in FIGS. 5A and 5B. As mentioned above, the spacer body 120 is mounted on the shaft 180 with its proximal end 182a fixed to the main shaft 180. But the distal end 182b of the spacer body 120 is not fixed to the shaft 180. Instead, the distal end 182b is slidable on main shaft 180. Thus, the distal sleeve 128b can be shifted back-and-forth relative to the proximal sleeve 128a. The shaft 180 has a lumen 184. The paired arrows D1 indicate the inner diameter at the distal end 182b of the spacer body 120. FIG. 7B shows a transverse cross-section of the spacer body 120. The sleeve is made of e-PTFE membrane 22. There is also a small gap 130 between the distal end 182b of spacer body 120 and the main shaft 180 to allow blood to flow therethrough.

Figure 6A:
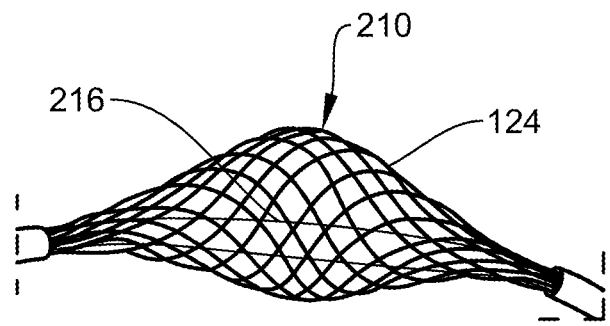
FIGS. 6A-6C show another example embodiment of a transcatheter device.
Figure 6B:
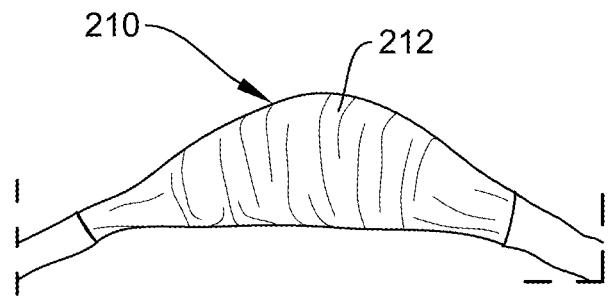
Figure 6C:
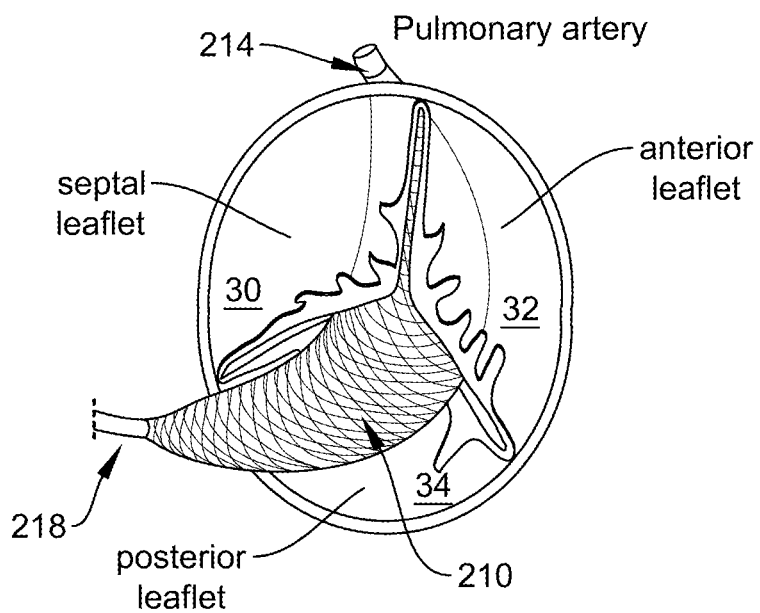

Croissant Bread Shape: FIGS. 6A-6C show another example embodiment of the transcatheter device. FIG. 6B shows the spacer body 210 having a shape that resembles a croissant. The external surface of the spacer body 210 is provided by a sleeve made of e-PTFE (expanded poly-tetra-fluoro-ethylene) membrane 212. FIG. 6A shows the inner frame 124 that is underneath and supporting the sleeve 212. The inner frame 124 is a mesh of flexible metal wires. The wires are nitinol alloy to give inner frame 124 sufficient rigidity to maintain the croissant shape in expanded configuration, but also sufficient flexibility so that it can be collapsed inside a vascular delivery sheath. FIG. 6C shows how the spacer body 210 could be positioned at the tricuspid valve. For reference, the distal end 214 and proximal end 218 of the spacer body 210 are shown. Because of the croissant shape of spacer body, the distal portion (towards distal end 214) of spacer body 210 is positioned behind (inferior) the septal leaflet 30 and the anterior leaflet 32 of the tricuspid valve. Whereas the proximal portion (towards proximal end 218) of the spacer body 210 is positioned above (superior) the posterior leaflet 34 of the tricuspid valve.

Figure 8A:
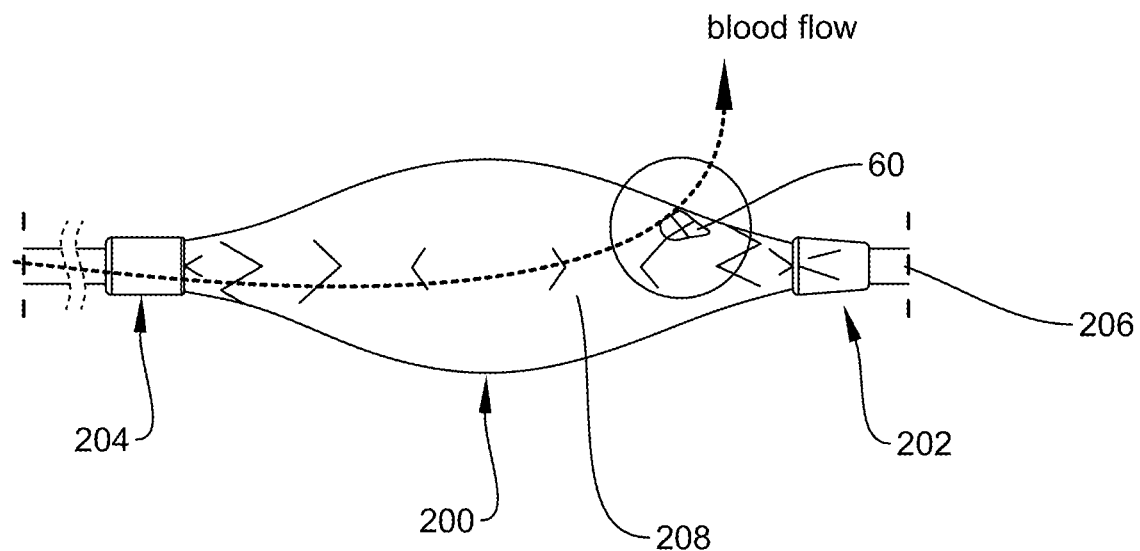
FIGS. 8A and 8B show close-up views of embodiments in which the spacer body has openings that allow the pass-through flow of blood.
Figure 8B:
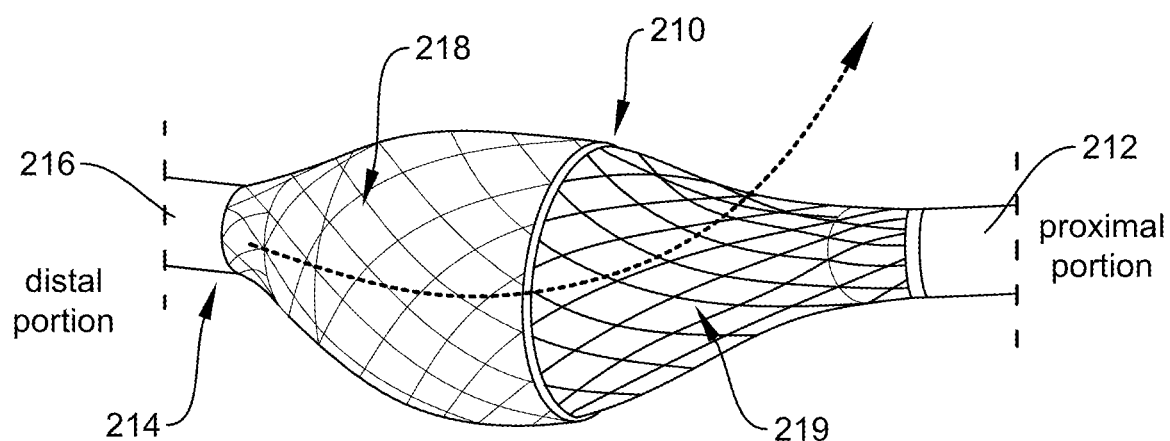

Spacer Body Openings: FIGS. 8A and 8B show close-up views of embodiments in which the spacer body has openings that allow the pass-through flow of blood. FIG. 8A shows a spacer body 200 having a distal end 204 and a proximal end 202. The spacer body 200 is mounted on a shaft 206. At the distal end 204, there is a small gap between spacer body 200 and the shaft 206. Also, there is a small hole 60 in the sleeve 208 that is a covering for spacer body 200. As shown by the dashed arrow, this allows blood to flow into the gap at distal end 204, through the spacer body 200, and out of the hole 60 in the sleeve 208. This depicts the direction of blood flow during systole. The direction of blood flow may be opposite or different in diastole.

FIG. 8B shows an alternate embodiment for the spacer body. In this embodiment, the spacer body 210 has a distal end 214 and a proximal end 212. The spacer body 210 is mounted on a shaft 216. At the distal end 214, there is a small gap between spacer body 210 and the shaft 216. Spacer body 210 has a sleeve 218 at its distal half only. There is no proximal sleeve, which exposes the underlying wire mesh frame 219. Thus, as shown by the dashed arrow, this allows blood to flow into the gap at distal end 214, through the spacer body 210, and out through the wire frame 219 at the proximal portion because there is no sleeve covering it, i.e. the proximal sleeve is omitted, only the distal sleeve is present. Also, in use, the sleeve 218 could be moved (advance forward or retract backwards) to adjust the size of the opening, and thus adjust the amount of blood flow through the spacer body 210. This depicts the direction of blood flow during systole. The direction of blood flow may be opposite or different in diastole.

Figure 9A:
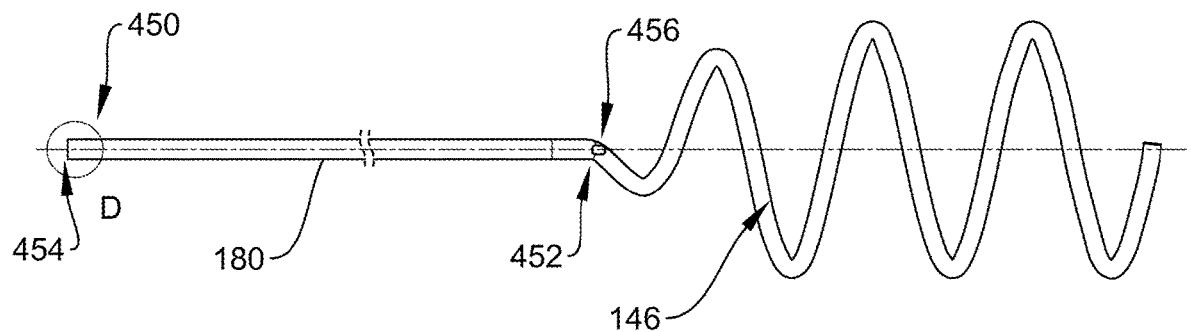
FIGS. 9A-9C show additional views of a transcatheter device.
Figure 9B:
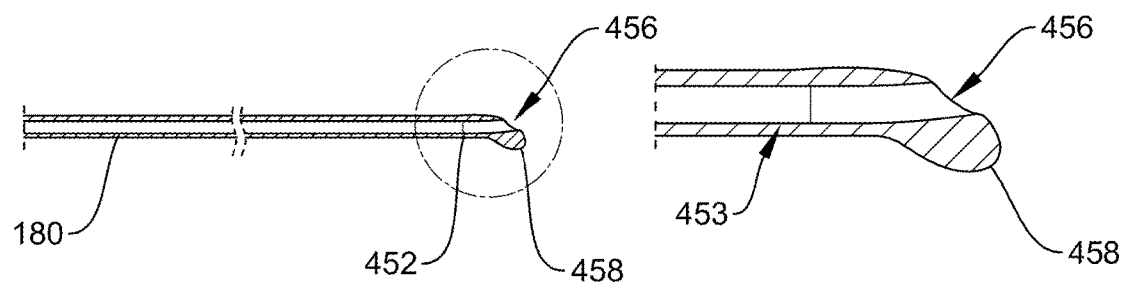
Figure 9C:
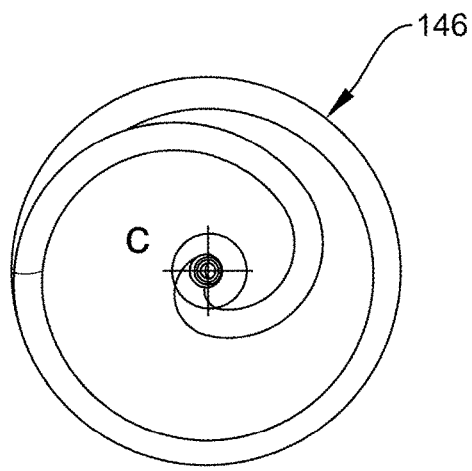

Main Shaft & Spiral Coil: FIGS. 9A-9C show additional views of the transcatheter device 100 of FIG. 2. FIG. 9A shows a condensed side view of the transcatheter device 100. For better visualization, the spacer body is omitted and the main shaft 180 is shown in condensed view. The main shaft 180 is made of a nitinol alloy core wire reinforced with Pellethane 55D (medical-grade thermoplastic polyurethane elastomer) braiding. The main shaft 180 has a distal end 450 and a proximal end 452. At the tip of its distal end 450, the shaft 180 has a distal end opening 454. At its proximal end 452, the shaft 180 has a proximal opening 456. The full length of the main shaft 180 is about 30 cm. Likewise, this is the same distance between the distal opening 454 and the proximal opening 456 of the main shaft 180. The spiral segment 146 has a length of about 7 cm (in relaxed pose, as measured along the longitudinal axis, not its travel length). The spiral member 146 is coaxial with the longitudinal axis of the main shaft 180.

FIG. 9B shows a close-up view of the proximal end 452 of the main shaft 180, in isolation without the attached spiral segment 146. The proximal opening 456 is seen here. This also shows that the proximal end 452 of the main shaft 180 has a rounded tip 458 adjacent the proximal opening 456. This also shows the lumen 453 of the main shaft 180. The guidewire 190 (see FIG. 2) travels through this lumen 453. The guidewire 190 has a diameter of about 0.035 inches. The rounded tip 458 could make guidewire insertion easier. Spiral coil 146 is made of a 0.019 inch nitinol wire core that is covered with Pellethane 55D (medical-grade thermoplastic polyurethane elastomer). In this example, the spiral coil 146 has three complete spirals. Alternatively, the spiral member 146 can be replaced with a stent-type structure depending on the patent's specific anatomy. FIG. 9C shows an end-on axial view of the spiral coil 146 with "C" representing the center of the spiral.

Deployment Procedure: FIGS. 10A-10C show how the transcatheter device 100 is deployed using a delivery sheath 460. The various parts are shown in condensed view. The 0.035 inch guidewire 190 is inserted into the entry vein and advanced along the path to be taken by the transcatheter device. External to the entry vein, the proximal end of the guidewire 190 is inserted into the lumen of the transcatheter device at the distal opening 454 at the tip of the distal tail 160. The transcatheter device is slid forward over the guidewire 190. The guidewire 190 exits out of the transcatheter device at the proximal opening 456 on the proximal segment 84 of the main shaft 180. The proximal end of guidewire 190 is inserted into the lumen of a deployment catheter 462 and the deployment catheter 462 is slid forward over the guidewire 190. The distal tip of the deployment catheter 462 comes near the proximal segment 84 of the main shaft 180, but does not enter the proximal opening 456. As shown in FIG. 10A, the transcatheter device together with deployment catheter 462 are inserted into the delivery sheath 460. Constrained inside the delivery sheath 460, the spiral coil 146 is compressed such that it stretches out along its longitudinal axis.

Using the deployment catheter 462 to push forward, this combined assembly is advanced along the path of the guidewire 190. That is, into the right atrium, across the tricuspid valve, and into the right ventricle. The distal tail 160 is advanced into the pulmonary artery. The spacer body 120 is adjusted to be in the desired position across the tricuspid valve. Meanwhile, the spiral coil 146 is inside the inferior vena cava. FIG. 10B shows that when the transcatheter device is ready to be anchored in place, the delivery sheath 460 is retracted so that its distal end 466 is behind the spacer body 120 (unsheathing). When the delivery sheath 460 is retracted so that its distal end 466 is behind the spiral coil 146, the spiral coil 146 expands and anchors itself inside the inferior vena cava. Proper positioning of the spacer body 120 and the spiral coil 146 can be confirmed by imaging (e.g. fluoroscope or echocardiogram). As shown in FIG.

10C, the delivery sheath 460 can now be fully withdrawn and removed. In completing the procedure, the guidewire 190 and the deployment catheter 462 are also fully withdrawn and removed.

FIGS. 23A and 23B show another view of the delivery assembly. FIG. 23A shows the transcatheter device with spacer body 120, distal tail 160, guidewire 190, proximal segment 84 of the main shaft, and spiral coil 146. The delivery system includes the delivery sheath 460 and the deployment catheter 462. The delivery sheath 460 is covering over the spiral coil 146 and the proximal segment 84 of the main shaft. This causes the spiral coil 146 to compress into a narrow extended configuration. However, the spacer body 120 is not covered by the delivery sheath 460. As such, spacer body 120 is shown in its expanded state. FIG. 23B shows the delivery sheath 460 advanced forward to cover the spacer body 120. This causes spacer body 120 to be compressed into a narrow configuration. This allows easier manipulation of the transcatheter device into the target site.

Figure 11A:
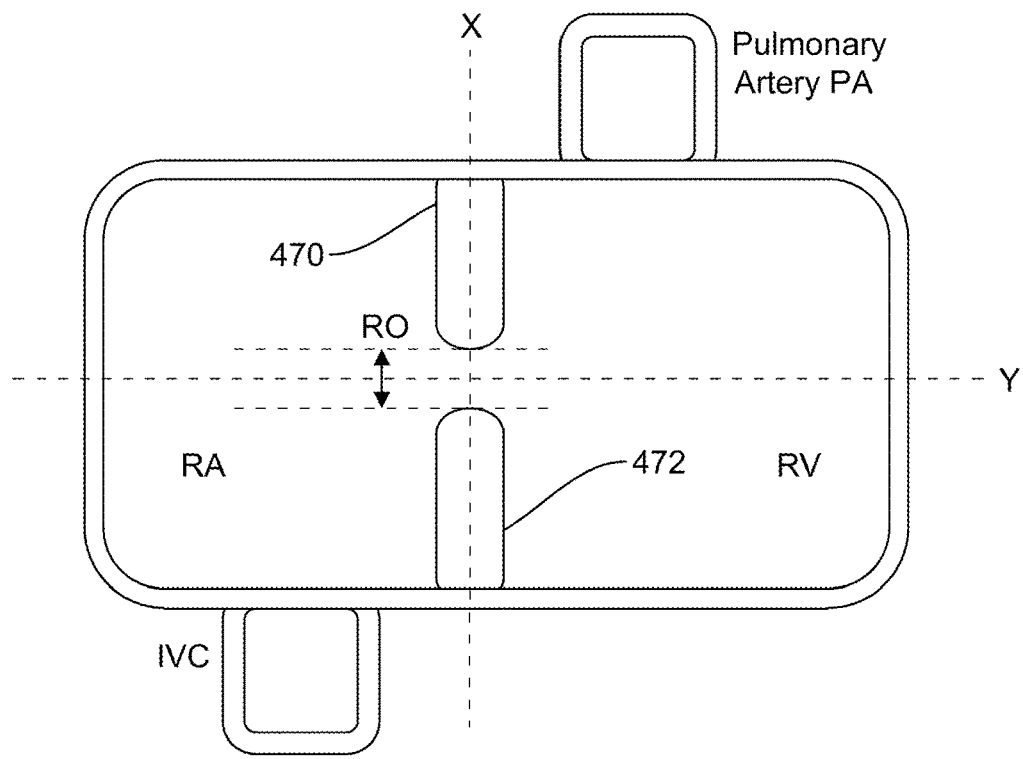
FIGS. 11A and 11B are schematic diagrams that show a profile view of a defective tricuspid valve.
Figure 11B:
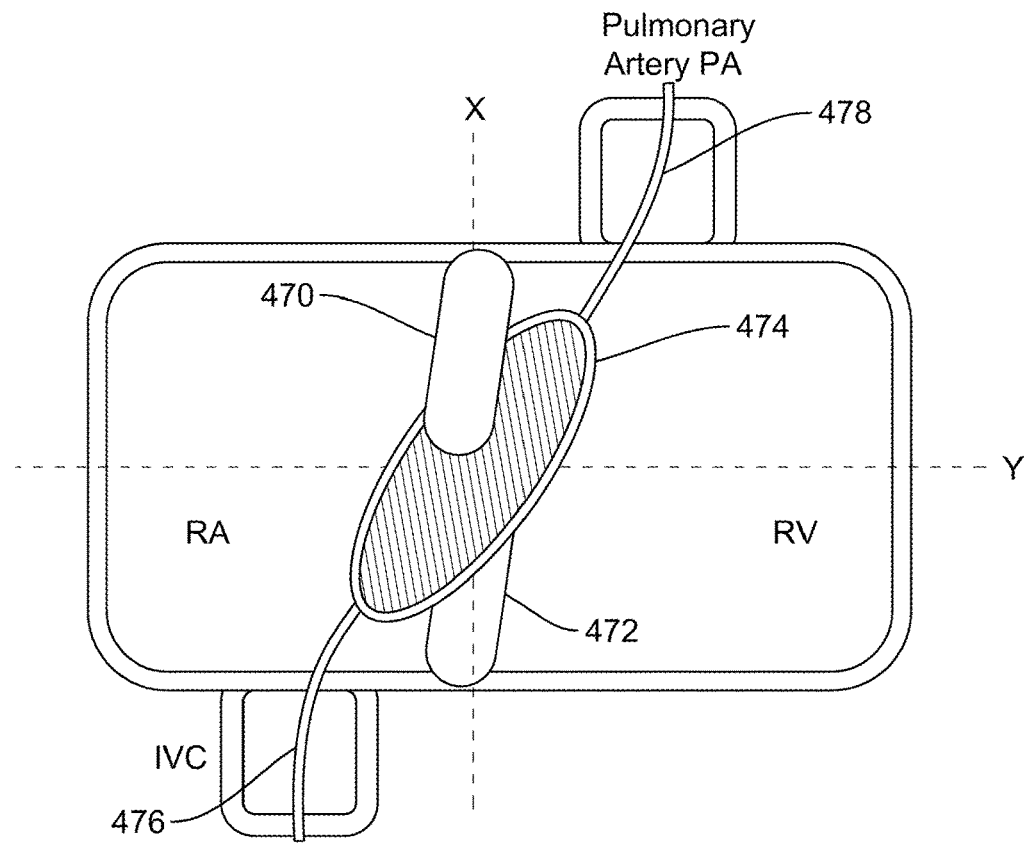

Oblique Positioning: FIGS. 11A and 11B are schematic diagrams that show a profile view of a defective tricuspid valve. The pulmonary artery (PA), right atrium (RA), right ventricle (RV), and inferior vena cava (IVC) are indicated. FIG. 11A shows the tricuspid valve leaflets 470/472 lacking sufficient coaptation, thereby creating a regurgitation orifice (RO). The tricuspid valve has a tricuspid annulus for which an annular plane can be defined. The annular plane is along the X-axis of the tricuspid annulus and orthogonal to the Y-axis of the tricuspid annulus. FIG. 11B shows a transcatheter device implanted in the heart. The transcatheter device comprises a spacer body 474 across the tricuspid valve, the distal tail 478 extending into the pulmonary artery, and proximal portion 476 extending into the inferior vena cava.

Figure 12:
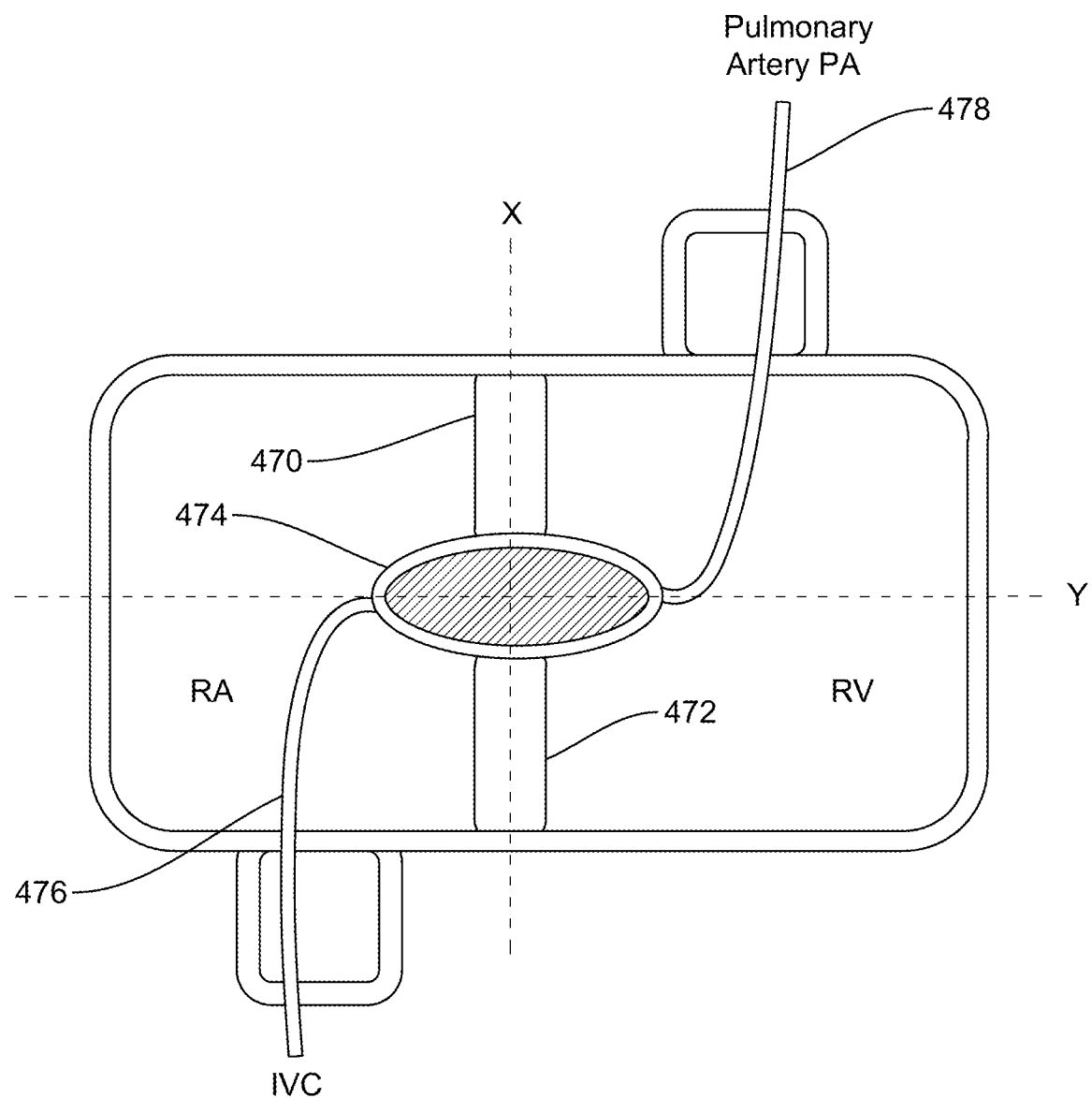
FIG. 12 shows a similar schematic diagram for a different embodiment.

See that the spacer body 474 provides a coaptation surface for the tricuspid valve leaflets 470/472. Also see that the spacer body 474 is positioned at an oblique angle relative to the annular plane. Because of this oblique angle, the spacer body 474 is positioned behind (posterior thereto) the septal and the anterior leaflets 470, but in front of (anterior thereto) the posterior leaflet 472. There are varying degrees of oblique angles for the spacer body to conform with anatomical differences among patients. This may depend on the width of the carvotricuspid isthmus in different patients, which may be the range of 3-5 cm width. In a patient with a relatively shorter carvotricuspid isthmus, a relatively shallow angle may be ideal to better accommodate the confined space of a short carvotricuspid isthmus. Also, having an L-preshaped bend at the proximal portion of the transcatheter device may conform better to the constrained space of a short carvotricuspid isthmus. In a patient with a relatively longer carvotricuspid isthmus, a relatively steeper oblique may be ideal. FIG. 12 shows a similar schematic diagram for a different embodiment. Here the spacer body 474 is positioned co-axial to the Y-axis and orthogonal to the annular plane.

Figure 14A:
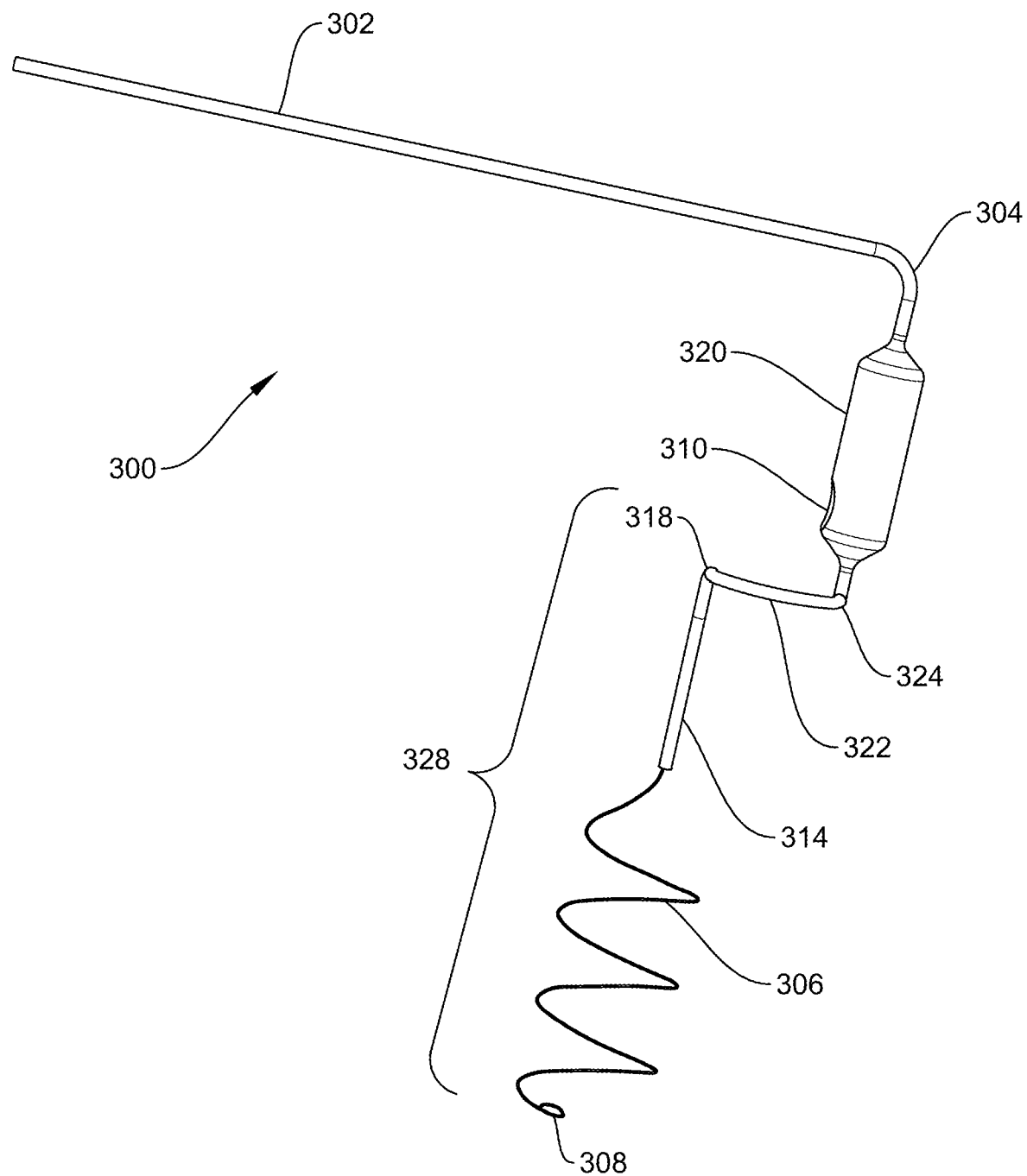
FIGS. 14A and 14B show another embodiment of a transcatheter device.
Figure 14B:
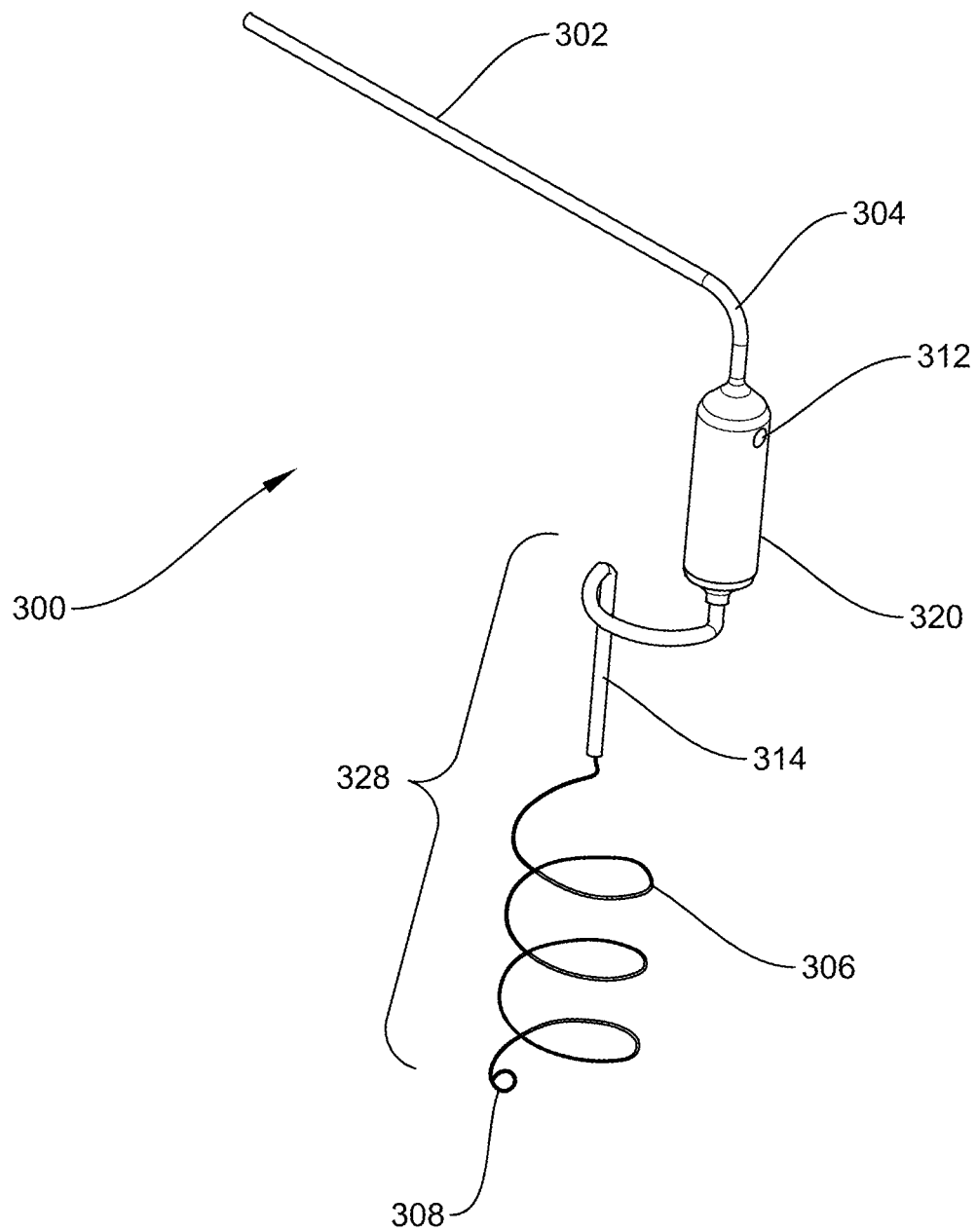

FIGS. 14A and 14B show another embodiment of the transcatheter device. In this embodiment, the transcatheter device 300 has a distal tail 302, spacer body 320, and proximal portion 328. The distal tail 302 has a bend 304. The proximal portion 328 comprises a proximal segment 314 of the main shaft and a spiral coil 306. The proximal segment 314 of the main shaft of the transcatheter device 300 has two bends 318/324 and a curve 322. The location and angles of bends 318/324 and the shape of curve 322 may depend on the patient's individual anatomy. The spiral coil 306 has a pigtail 308. Also shown for this embodiment is a proximal opening 310 on spacer body 304 and a distal opening 312. Experimental work done on pig models of tricuspid valve defect showed that having fenestration opening 310 (distal) and outflow opening 312 (distal) results in better neo-biotissue covering compared to the non-fenestrated spacer body design shown in FIG. 6B.

Figure 16A:
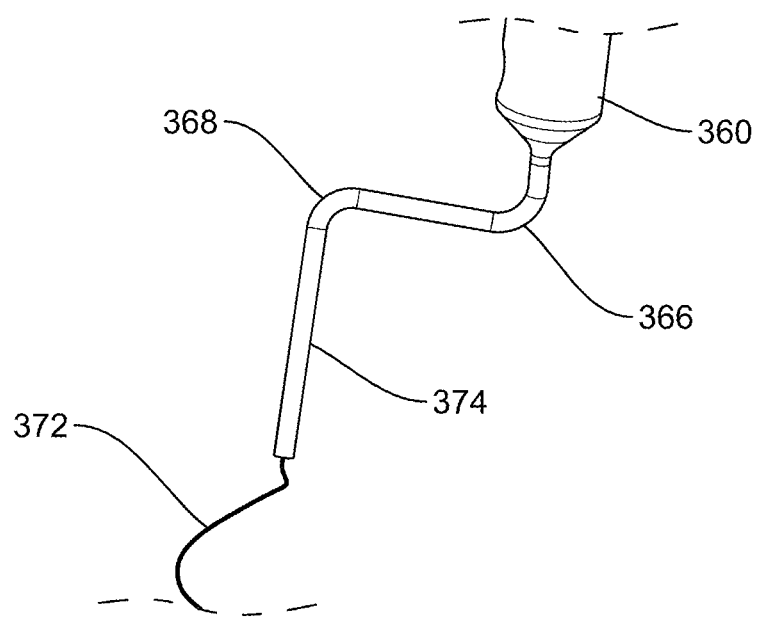
FIGS. 16A and 16B show various perspective views of another embodiment of a transcatheter device.
Figure 16B:
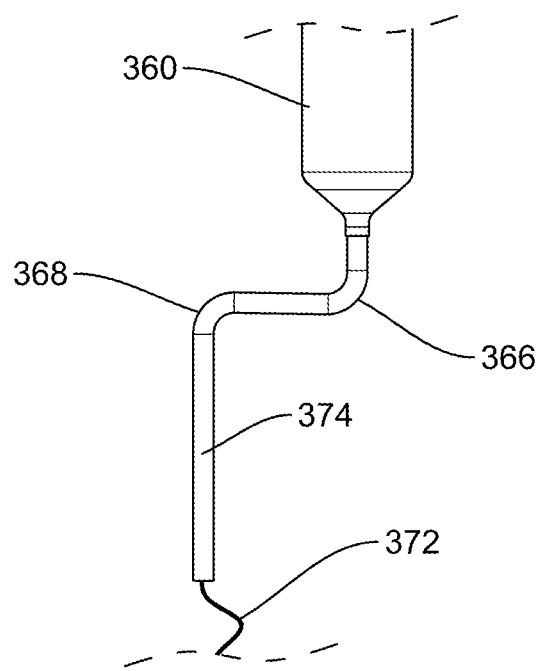

FIGS. 16A and 16B show close-up views of a different design for the proximal segment of the main shaft. Shown here is a spacer body 360 (partial view) and the proximal portion of the transcatheter device. The proximal portion comprises a proximal segment 374 of the main shaft and a spiral coil 372 (partial view). The proximal segment of the main shaft has two bends 366 and 368, but there is no curve.

Figure 15A:
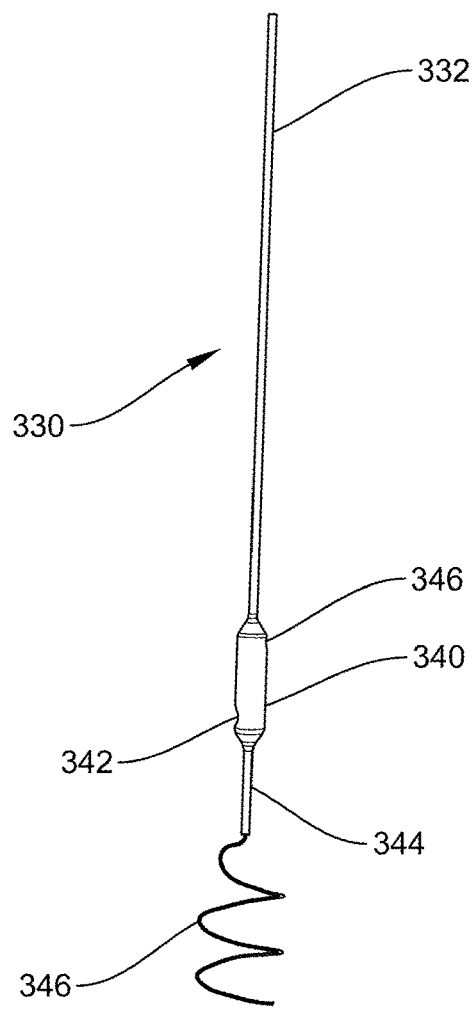
FIGS. 15A-C show various perspective views of another embodiment of a transcatheter device.
Figure 15B:
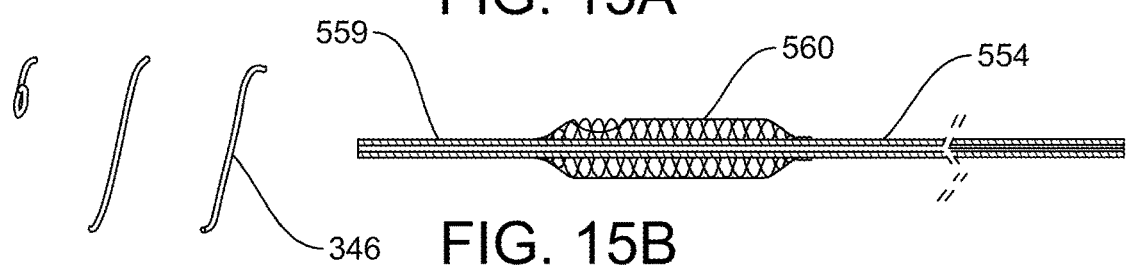
Figure 15C:
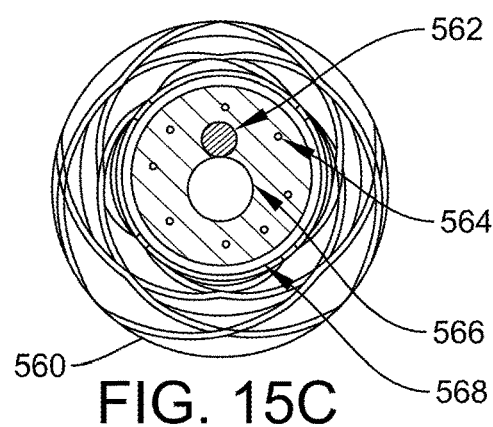

FIGS. 15A-15C show various views of another embodiment of the transcatheter device. FIG. 15A shows a perspective view; FIG. 15B shows a longitudinal cross-section view; FIG. 15C shows a proximal end-on view. In this embodiment, the distal tail 332 of the transcatheter device 330 has a straight configuration (no bend). This transcatheter device 330 also has a main shaft with its proximal segment 344, which is short and has a straight configuration. Also shown are spacer body 340 and spiral coil 346. The spacer body 340 has a generally cylindrical shape with conical ends. There is a proximal opening 342 and a distal opening 346 on the spacer body 340 to allow blood flow therethrough. In an alternate embodiment, the spacer body 340 has only one such opening, either proximal opening 342 or distal opening 346.

As shown in FIG. 15B, spacer body 340 comprises a wire mesh scaffolding 560 covered with an e-PTFE membrane to provide the outer surface. This wire mesh scaffolding 560 gives the spacer body 340 the ability to collapse or expand during the deployment procedure. FIG. 15C shows an end-on view of the wire mesh scaffolding 560. The main shaft 559 of the transcatheter device has a lumen 566 for insertion of a guidewire. At the distal end of the spacer body 340, there is a sleeve gap 568 from the main shaft 559. Because the distal end of the spacer body 340 is not affixed to the main shaft 559 at this sleeve gap 568, the distal end of the spacer body 340 is slidable on the main shaft 559. The main shaft 559 is made of a nitinol core wire 562 sheathed in polyurethane and reinforced with wire braiding 564.

Figure 17:
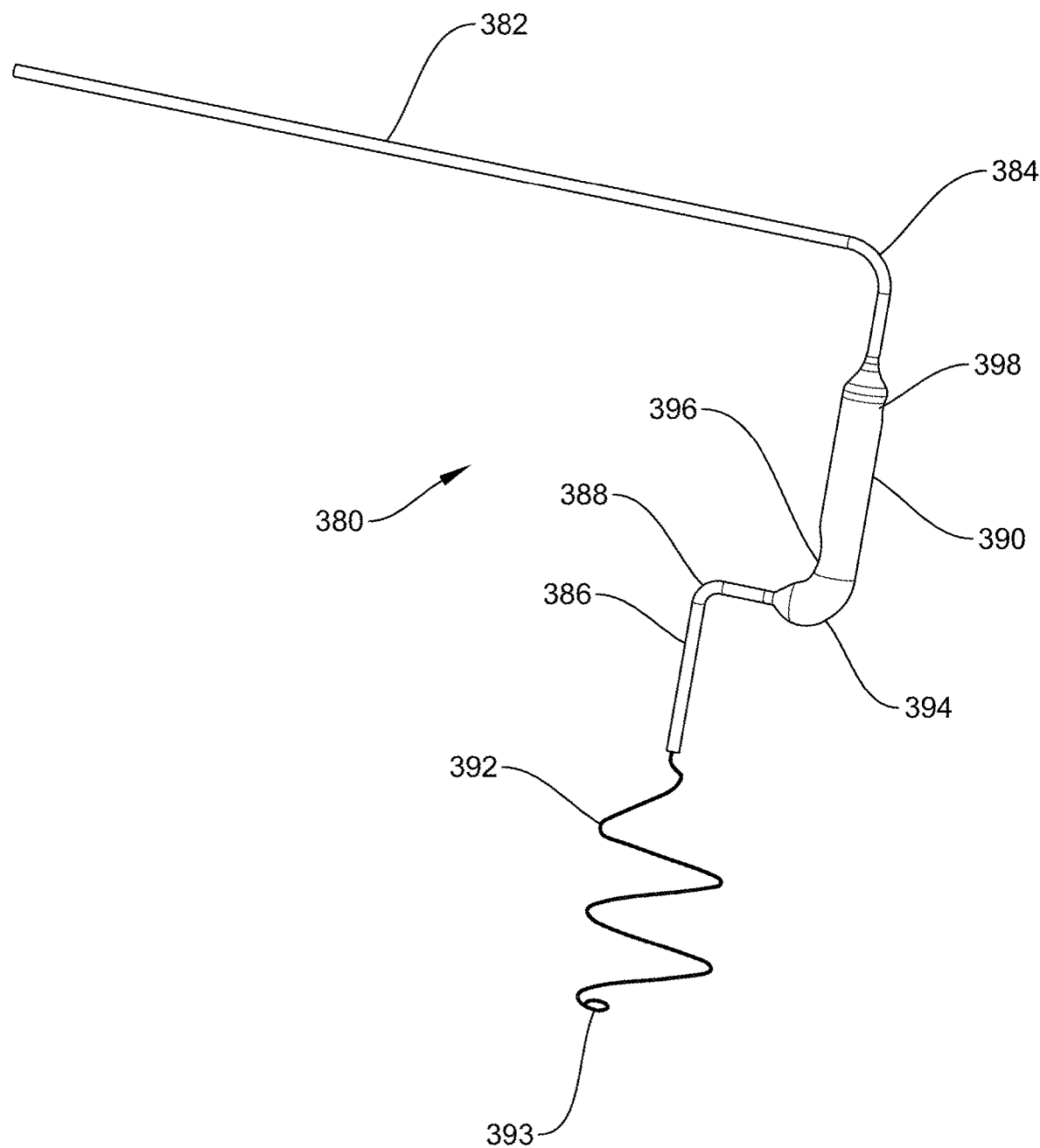
FIG. 17 shows another embodiment of a transcatheter device.

FIG. 17 shows another embodiment of the transcatheter device. In this embodiment, the distal tail 382 of the transcatheter device 380 has a bend 384. The proximal segment 386 of the main shaft has a single bend 388. The spiral coil 392 is attached to the proximal segment 386 of the main shaft. The spiral coil 392 also has a pigtail 393. The spacer body 390 has a boot shape with a curve 394 at its proximal end. There is also a proximal opening 396 and a distal opening 398 on the spacer body 390.

Figures 18A, 18B:
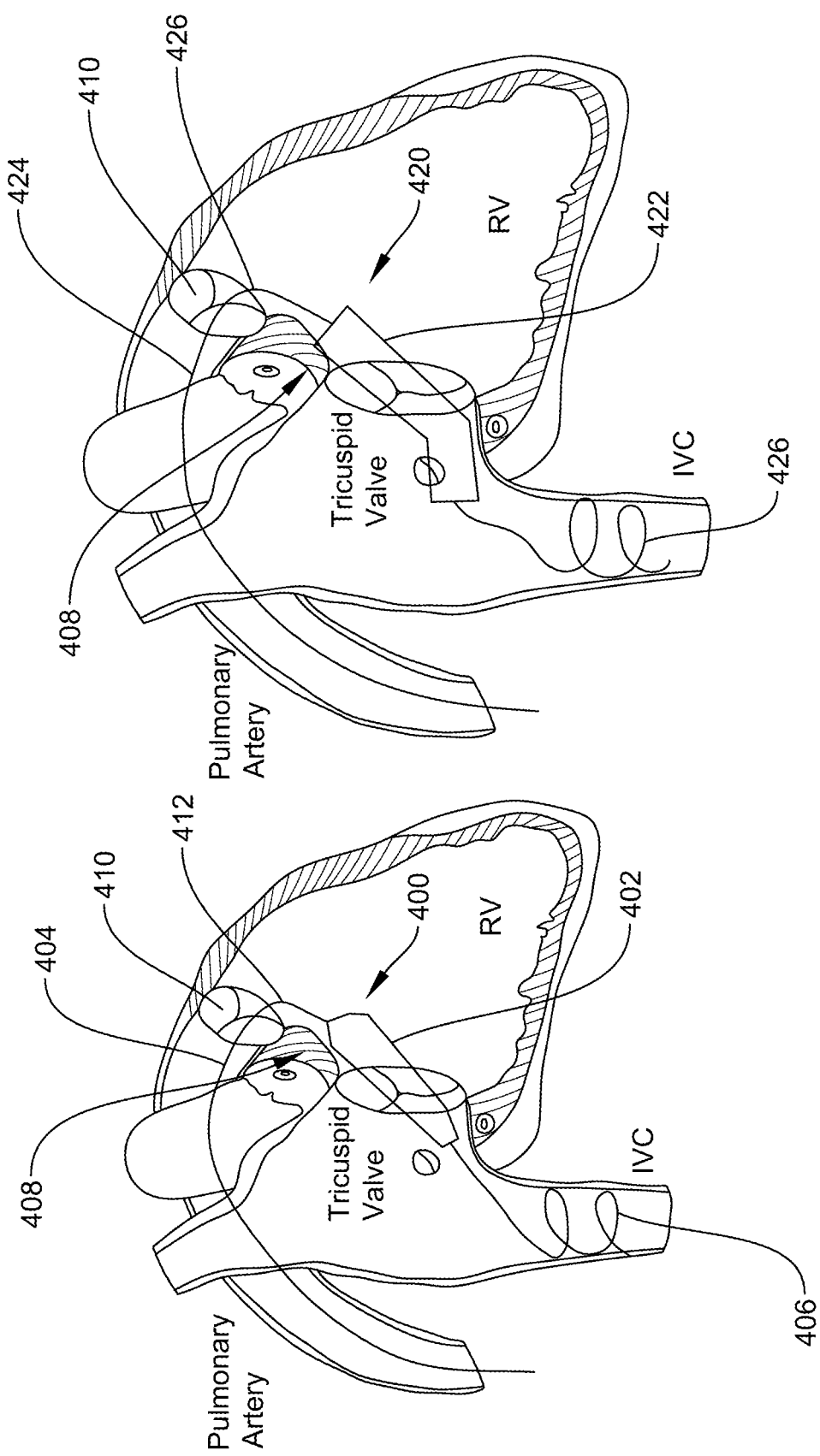
FIGS. 18A and 18B show how a transcatheter device of this invention could be positioned in the patient's heart.
Figure 19A:
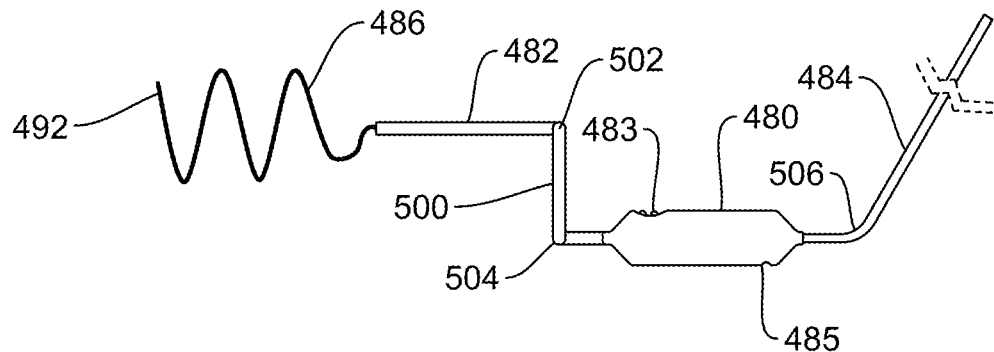
FIGS. 19A-H and 19 K show various views of another embodiment of a transcatheter device.

FIGS. 18A and 18B show how a transcatheter device of this invention could be positioned in the patient's heart. In FIG. 19A, the transcatheter device 400 has a football shaped spacer body 402, along with distal tail 404 and spiral coil 406. The patient's heart is shown in cross-section view with tricuspid valve and pulmonary valve 410. As seen in this view, the spacer body 402 is positioned across the tricuspid valve and the distal tail 404 travels across the pulmonary valve 410 and into the right pulmonary artery. Note that distal tail 404 has a bend 412 that facilitates its direction towards the right pulmonary artery. The distal part of spacer body 402 abuts against the supraventricular crest 408.

In FIG. 18B, the transcatheter device 420 has a boot-shaped spacer body 422, along with distal tail 424 and spiral coil 426. The patient's heart is shown in cross-section view with tricuspid valve and pulmonary valve 410.

As seen in this view, the spacer body 422 is positioned across the tricuspid valve and the distal tail 424 travels across the pulmonary valve 410 and into the right pulmonary artery. Note that distal tail 424 has a bend 426 that facilitates its direction towards the right pulmonary artery. Also note that boot-shaped spacer body 422 facilitates its abutment against the supraventricular crest 408.

Figure 19B:
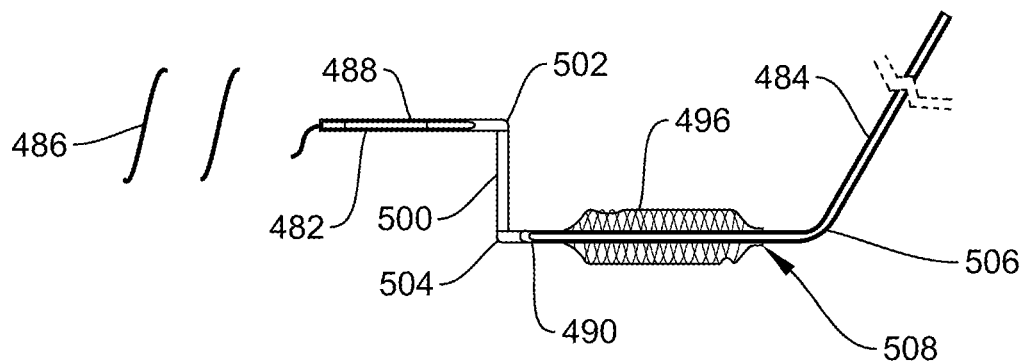
Figure 19C:
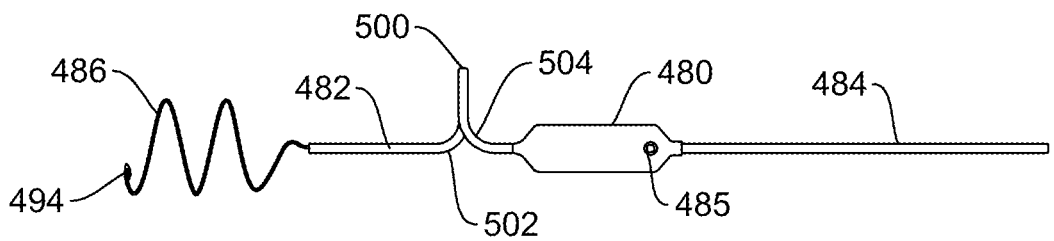
Figure 19D:
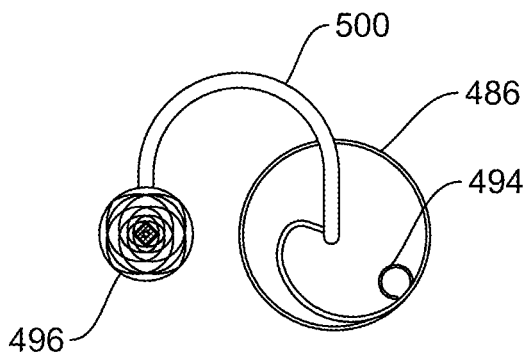

FIGS. 19A-H and 19K show various views of an embodiment of the transcatheter device. FIG. 19A shows a side view and FIG. 19B shows a longitudinal cross-section, cutaway view. FIG. 19C shows a side view at a different rotation. FIG. 19D shows a proximal end-on view. The transcatheter device has a spacer body 480, a spiral coil 486, and a distal tail 484. The spiral coil 486 has a hook 492 for recapturing the transcatheter device if it needs to be pulled out. The spacer body 480 has a generally cylindrical shape with conical ends. The spacer body 480 has a proximal opening 483 and a distal opening 485 to allow blood flow therethrough. The distal tail 484 has a bend 506.

At the proximal portion of the transcatheter device is the proximal segment 482 of the main shaft 490. This proximal segment 482 has several contour features. It has two bends 502/504. Between the bends 502/504, there is a curved segment 500, which may have a curvature of 80-120° depending on the patient's specific anatomy. This curved segment 500 brings the spacer body 480 closer to the supraventricular crest of the heart. The location of the bends 502/504 and the dimensions of the curved segment 500 may vary depending on the patient's specific anatomy.

Figure 19E:
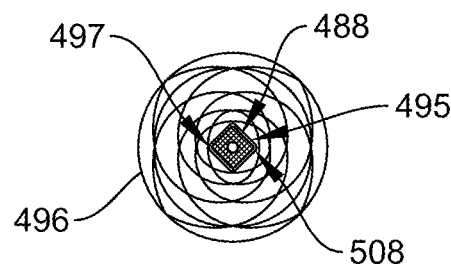

FIG. 19B (transverse cross-section) shows that the spacer body 480 comprises a wire mesh scaffolding 496 covered with an e-PTFE membrane to provide the outer surface. This wire mesh scaffolding 496 gives the spacer body 480 the ability to collapse or expand during the deployment procedure. FIG. 19E shows an end-on view of the wire mesh scaffolding 496. The main shaft 490 has a lumen 488 for insertion of a guidewire. At the distal end of the spacer body 480, there is a sleeve gap 508 from the main shaft 490. Because the distal end of the spacer body 480 is not affixed to the main shaft 490 at this sleeve gap 508, the distal end of the spacer body 480 is slidable on the main shaft 490. The main shaft 490 is made of a nitinol core wire 497 reinforced with polyurethane braiding 495.

FIGS. 19F-19H and 19K show the transcatheter device implanted in the heart with its path from the inferior vena cava, into the right atrium (RA), across the tricuspid valve, into the right ventricle (RV), touching the supraventricular crest 505, through the pulmonary valve 507, and traveling into the right pulmonary artery (PA). This path through the heart enables the transcatheter device to remain in stable position and resistant to anterior-to-posterior movement despite the beating motion of the heart. In addition, this path may enable the transcatheter device to be flexible for lateral movement so that it could "self-center" its position as described below.

Figure 19F:
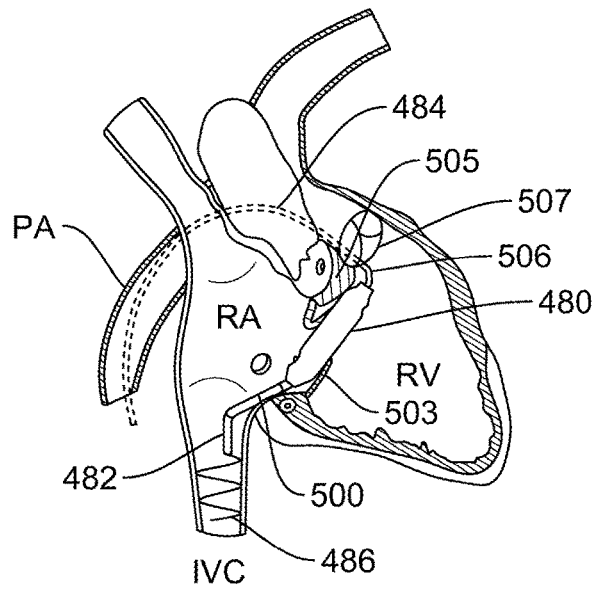
Figure 19G:
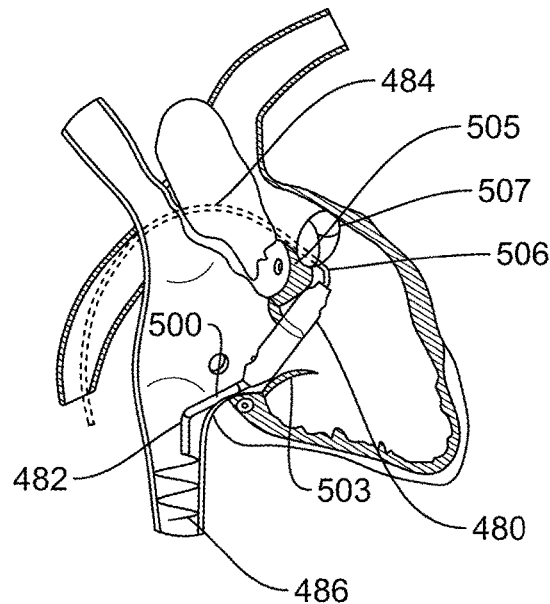
Figure 19H:
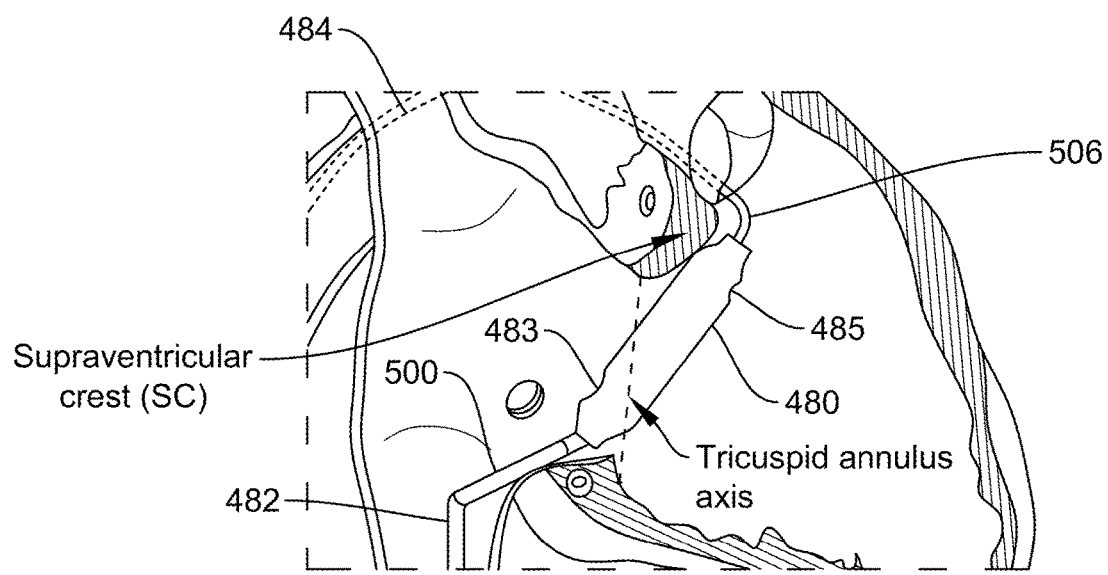
Figure 19K:
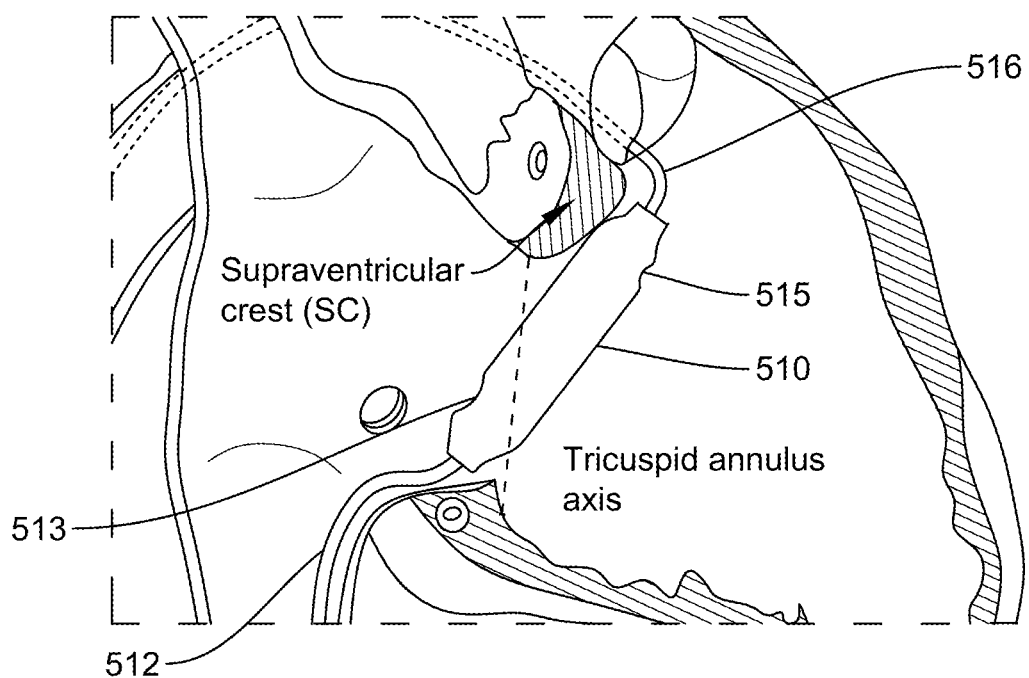

FIG. 19F shows the heart in systole with the tricuspid valve leaflets 503 closed around the spacer body 480. FIG. 19G shows the heart in diastole with the tricuspid valve leaflets 503 in open position. The tricuspid valve leaflets 503 are spread apart from the spacer body 480, thereby allowing blood flow around the spacer body 480. See that the L-shaped bend 506 in the distal tail 484 helps the distal portion of the spacer body 480 to be closer to the supraventricular crest 505. This bend 506 also directs the distal tail 484 into the right pulmonary artery (instead of the left pulmonary artery). Also see that the contour features of the proximal segment 482 helps to keep the spacer body 480 at an oblique angle relative to the annular plane of the tricuspid valve. FIG. 19H shows a close-up view. FIG. 19K is a close-up view showing an alternate design for the proximal segment 512 having a more gentle curved shape.

Figure 20A:
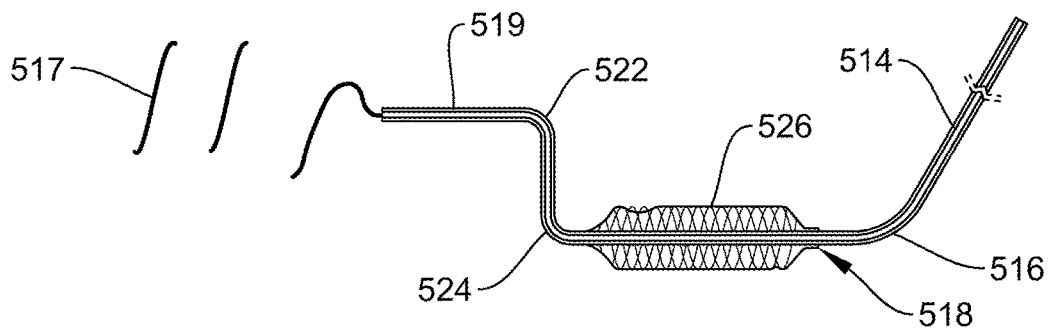
FIGS. 20A-E show various views of another embodiment of a transcatheter device.
Figure 20B:
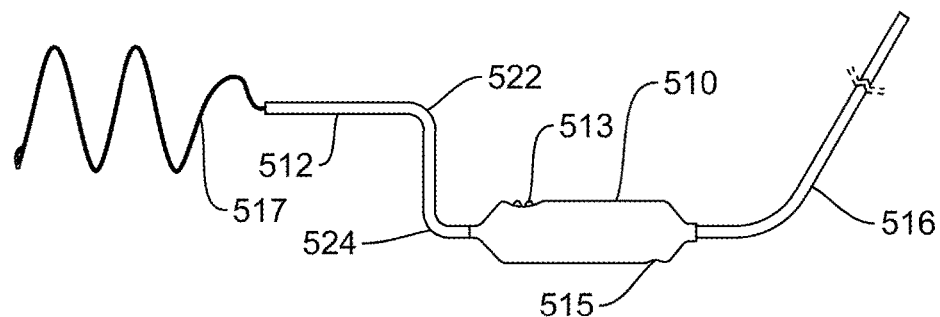
Figure 20C:
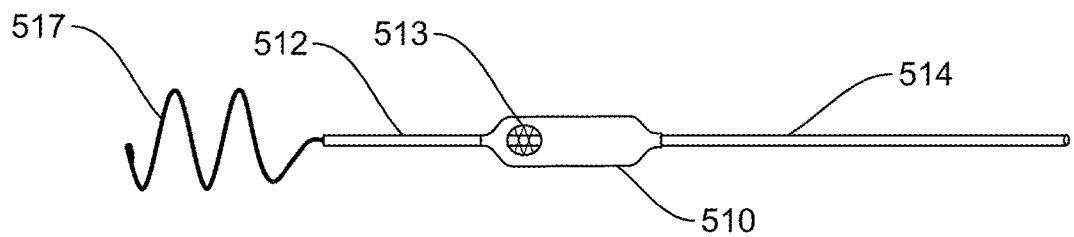
Figure 20D:
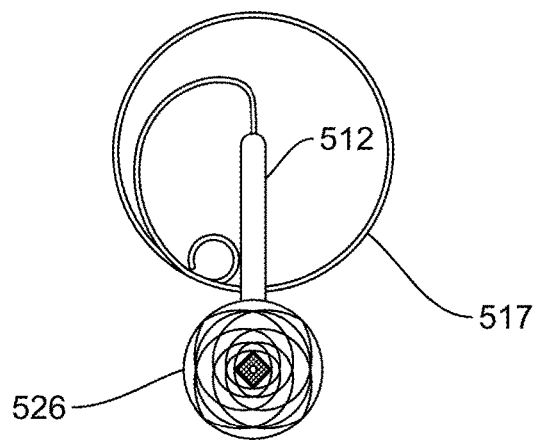

FIGS. 20A-20E show various views of another embodiment of the transcatheter device. FIG. 20A shows a transverse cross-section view; FIG. 20B shows a side view; FIG. 20C shows a top view; FIG. 20D shows a proximal end-on view. The transcatheter device has a spacer body 510, a spiral coil 517, and a distal tail 514. The spacer body 510 has a generally cylindrical shape with conical ends. The spacer body 510 has a proximal opening 513 and a distal opening 515 to allow blood flow therethrough. The distal tail 514 has a bend 516.

Figure 20E:
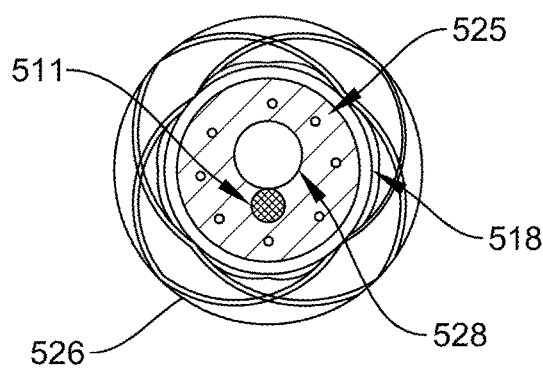

At the proximal portion of the transcatheter device is the proximal segment 512 of the main shaft 519. This proximal segment 512 has two bends 522/524. The location and angle of the bends 522/524 may vary depending on the patient's specific anatomy. The spacer body 510 comprises a wire mesh scaffolding covered with an e-PTFE membrane to provide the outer surface. This wire mesh scaffolding gives the spacer body 510 the ability to collapse or expand during the deployment procedure. FIG. 20E shows an end-on view of the wire mesh scaffolding 526. The main shaft 519 has a lumen 528 for insertion of a guidewire. At the distal end of the spacer body 510, there is a sleeve gap 528 from the main shaft 519. Because the distal end of the spacer body 510 is not affixed to the main shaft 519 at this sleeve gap 518, the distal end of the spacer body 510 is slidable on the main shaft 519. The main shaft 519 is made of a nitinol core wire 517 reinforced with polyurethane braiding 525.

FIGS. 21A-21E show various views of another embodiment of the transcatheter device. FIG. 21A shows a side view and FIG. 21B shows a longitudinal cross-section, cutaway view. FIG. 21C shows a side view at a different rotation. FIG. 21D shows a proximal end-on view. The transcatheter device has a spacer body 530, a spiral coil 537, and a distal tail 534. The spacer body 530 has a boot shape with a 90° curved proximal portion 531. The spacer body 530 has a proximal opening 533 and a distal opening 535 to allow blood flow therethrough. The distal tail 536 has a bend 536.

At the proximal portion of the transcatheter device is the proximal segment 532 of the main shaft 539. This proximal segment 532 has a 90° outward bend 542. The spacer body 530 comprises a wire mesh scaffolding 546 covered with an e-PTFE membrane to provide the outer surface. This wire mesh scaffolding 546 gives the spacer body 530 the ability to collapse or expand during the deployment procedure. FIG. 21E shows an end-on view of the wire mesh scaffolding 546. The main shaft 539 has a lumen 548 for insertion of a guidewire. At the distal end of the spacer body 530, there is a sleeve gap 538 from the main shaft 539. Because the distal end of the spacer body 530 is not affixed to the main shaft 539 at this sleeve gap 538, the distal end of the spacer body 530 is slidable on the main shaft 539. The main shaft 539 is made of a nitinol core wire 547 reinforced with polyurethane braiding 545.

FIGS. 21F-21H show the transcatheter device implanted in the heart with its path from the inferior vena cava, into the right atrium (RA), across the tricuspid valve, into the right ventricle (RV), touching the supraventricular crest 505, through the pulmonary valve 507, and traveling into the right pulmonary artery (PA). FIG. 21F shows the heart in systole with the tricuspid valve leaflets 503 closed around the spacer body 530. FIG. 21G shows the heart in diastole with the tricuspid valve leaflets 503 in open position. The tricuspid valve leaflets 503 are spread apart from the spacer body 530, thereby allowing blood flow around the spacer body 530. See that the bend 536 in the distal tail 534 helps the distal portion of the spacer body 530 to be closer to the supraventricular crest 505. This bend 536 also directs the distal tail 534 into the right pulmonary artery (instead of the left pulmonary artery).

Also see that the contour features of the proximal segment 532 and the boot-shaped curve 531 at the proximal portion of the spacer body 530 helps to keep the spacer body 530 at an oblique angle relative to the annular plane of the tricuspid valve. FIG. 21H is a close-up view showing the distal portion of spacer body 530 abutting against the supraventricular crest 505. Also see that the bend 531 at the boot-shaped spacer body 530 boot abuts against the carvotricuspid isthmus.

Figure 24A:
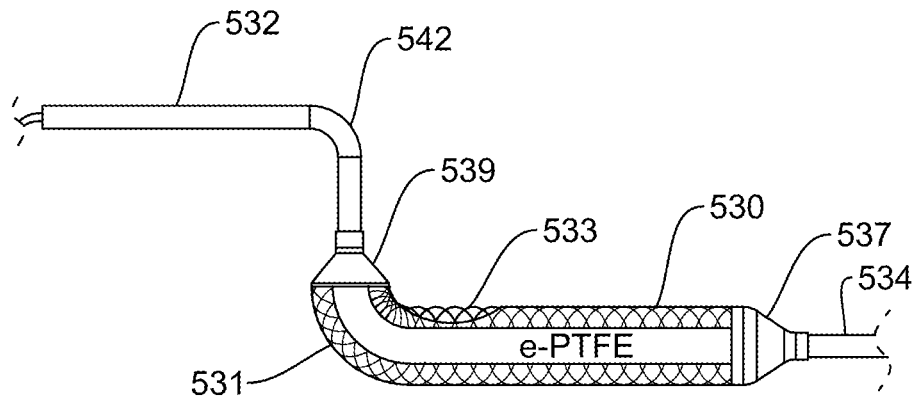
FIGS. 24A-G show various views of a spacer body.
Figure 24B:
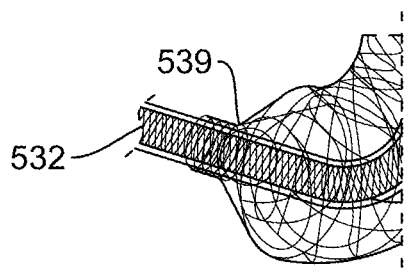
Figure 24C:
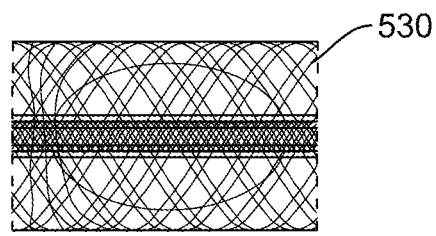
Figure 24D:
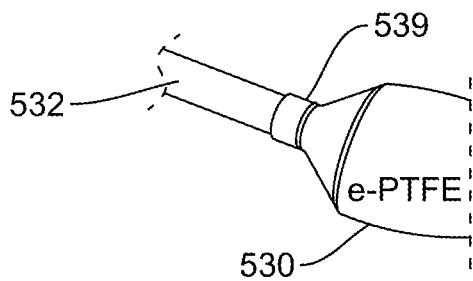
Figure 24E:
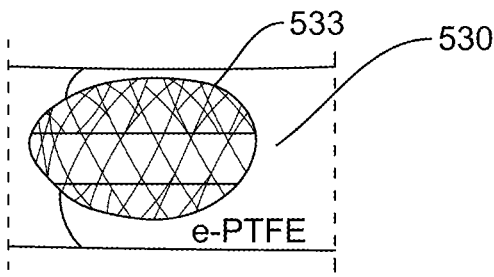
Figure 24F:
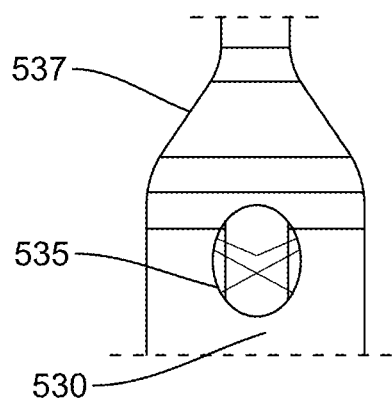
Figure 24G:
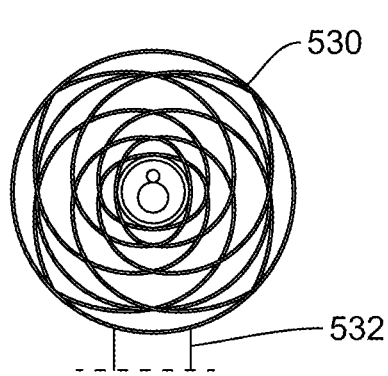

FIG. 24A shows a side view of the spacer body 530 with a partial see-through view showing the internal wire mesh framework. FIG. 24B shows a close-up see-through view of the proximal end 539 of the spacer body 530 showing the internal wire mesh framework. FIG. 24C shows a close-up see-through view of the mid-portion of the spacer body 530 showing the internal wire mesh framework. FIG. 24D shows a close-up view of the proximal end 539 of the spacer body 530 as covered with an e-PTFE membrane as a sleeve. FIG. 24E shows a close-up view of the proximal opening 533 on the spacer body 530 with the internal wire mesh framework visible therethrough. FIG. 24F shows a close-up view of the distal opening 535 at the distal end 537 of the spacer body 530 with the internal wire mesh framework visible. FIG. 24G shows an end-on view of the wire mesh framework for spacer body 530.

Figure 22A:
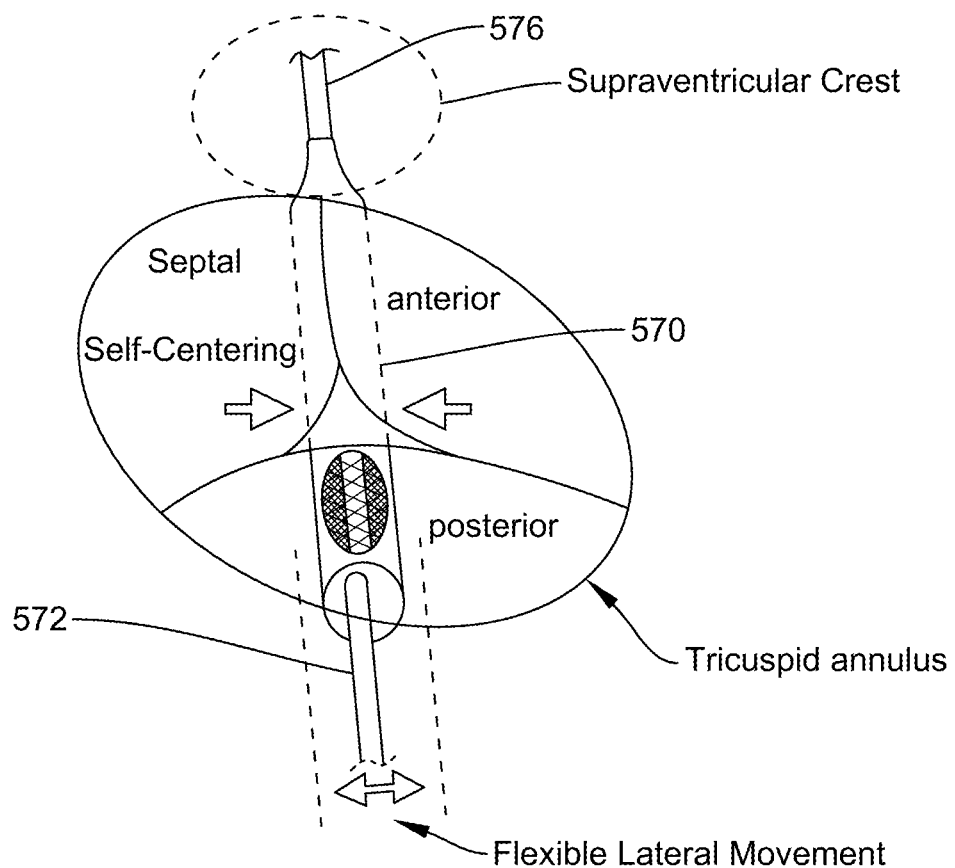
FIGS. 22A and 22B illustrate how the spacer body on a transcatheter device could be "self-centering" within the tricuspid valve.
Figure 22B:
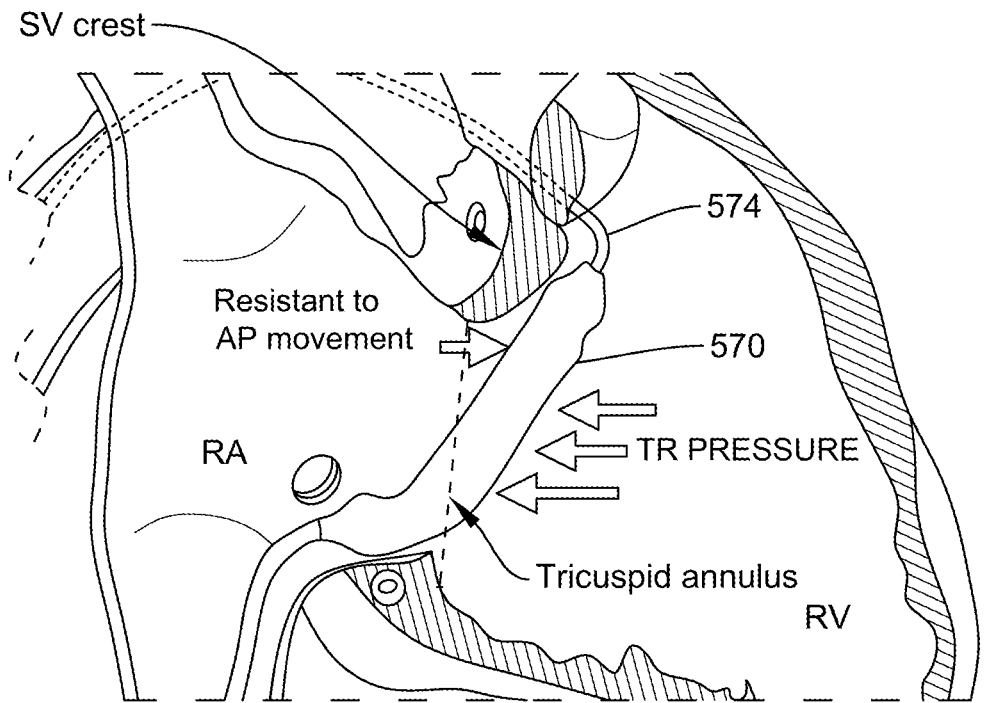

Self-Centering: FIGS. 22A and 22B illustrate how the spacer body on the transcatheter device could be "self-centering" within the tricuspid valve. FIG. 22A shows the transcatheter device comprising a spacer body 570, proximal segment 572 of the main shaft, and distal tail 576. The location of the supraventricular crest is shown in the dashed circle. The distal tail 576 has a bend 574 that facilitates positioning of the spacer body against the supraventricular crest. The anterior, septal, and posterior leaflets are labelled. An edge-on view of the tricuspid annulus is also shown. As seen in FIG. 22A, there is flexibility in the lateral movement relative to the posterior leaflet. FIG. 22B shows how the distal portion of spacer body 570 abuts against the supraventricular crest. Pulsating pressure within the beating right ventricle repeatedly pushes spacer body 570 so that it wobbles with anterior-to-posterior (AP) movement. As seen here, with this positioning, the supraventricular crest acts as a wall that impedes anterior-to-posterior (AP) movement of the spacer body 570 between the anterior and septal leaflets.

In experimental testing in pigs, visualization by echocardiogram showed that the spacer body uses the supraventricular crest as a robust buttress against systolic pressure during right ventricle contraction. Thus, the overall design of the transcatheter device conforms to the internal cardiac and vascular anatomy to prevent excess migration.

Distal Tail: FIGS. 25A-25C show different embodiments of the distal tail. FIG. 25A shows a distal tail 580 having a bend 582. Distal tail 580 extends from the distal end 584 of the spacer body. FIG. 25B shows an alternate embodiment in which distal tail 580 has a distal section 587 that is naked nitinol wire, and a proximal section 586 that is nitinol wire with a covering sheath (e.g. with e-PTFE coating or Pellethane 55D braiding). FIG. 25C shows a close-up view of the distal segment 587 in which the nitinol wire has a rounded tip 588. This rounded tip 588 makes the tip of the nitinol wire blunt so that it reduces trauma as it travels into pulmonary artery.

Figure 26:
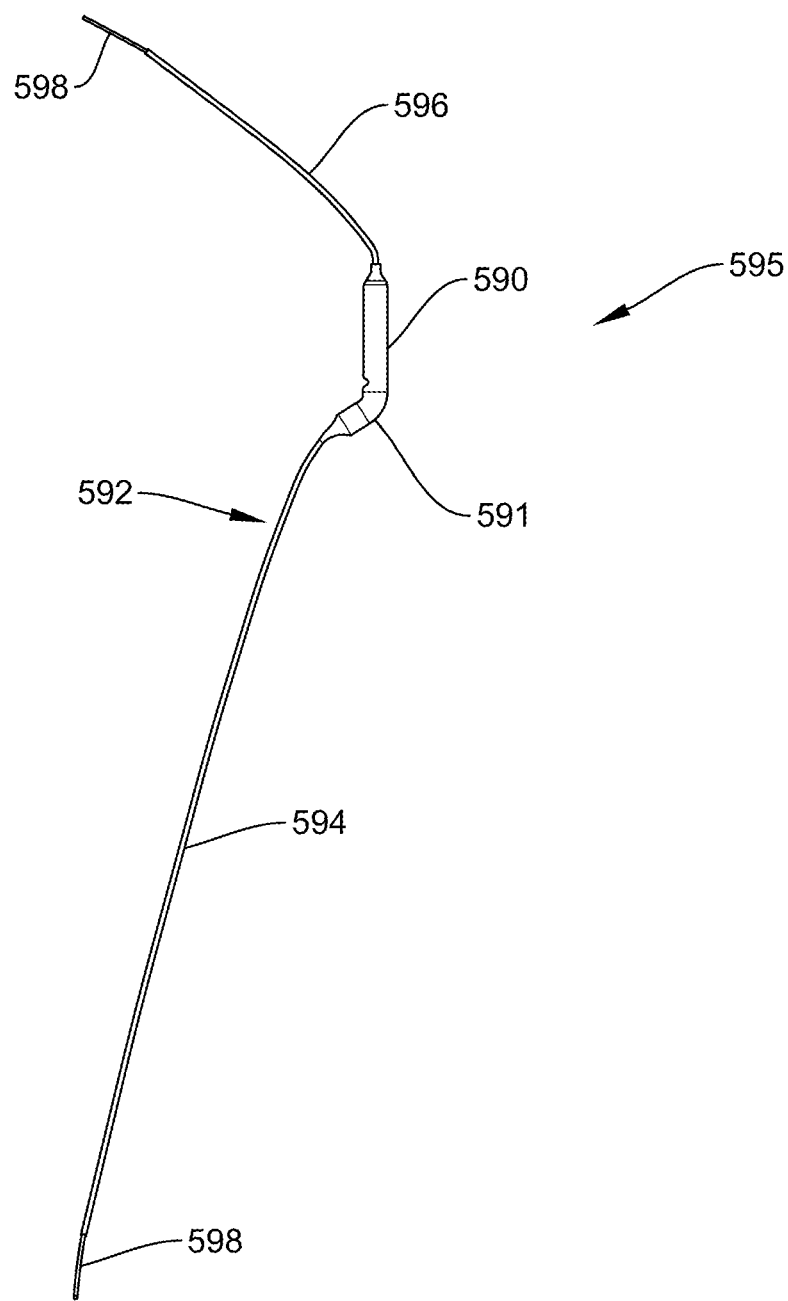
FIG. 26 shows an alternate embodiment of a transcatheter device which lacks a spiral coil at its proximal portion

FIG. 26 shows an alternate embodiment of a transcatheter device which lacks a spiral coil at its proximal portion. This transcatheter device 595 comprises a boot-shaped spacer body 590, main shaft 592, distal tail 596, guidewire 598, and proximal segment 594 of the main shaft 592. The boot-shaped spacer body 590 has a curved portion 591.

Figure 27:
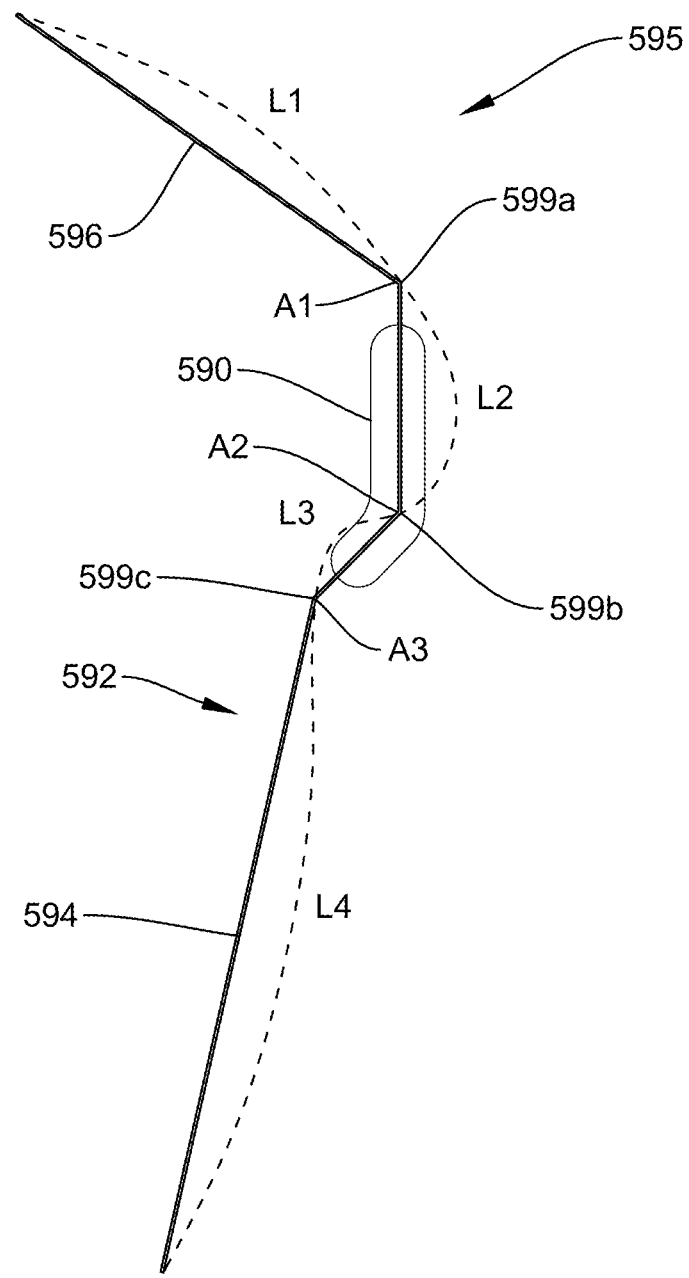
FIG. 27 shows the dimensional parameters of a transcatheter device.

FIG. 27 shows the dimensional parameters of the transcatheter device 595. L1 is the length of the distal tail 596. L2 is the length of the main shaft 592 encompassing the straight portion of the spacer body 590. L3 is the length of the main shaft encompassing the curved portion 591 of the spacer body 590. L4 is the length of the proximal segment 594 of the main shaft 592. As examples, L1 could be 20-25 cm long, L2 could be 6-9 cm long, L3 could be 2-3.5 cm long, and L4 could be 90-120 cm long. A1 is the inner angle of the bend 599a in the main shaft 592 as it converts to the distal tail 596. A2 is the inner angle in the bend 599b at the curve in the boot-shaped spacer body 590. Angles A1 and A2 could be in the range of 80-120°. A3 is the inner angle of the bend 599c in the main shaft 592 as it converts to the proximal segment 594.

Figure 28A:
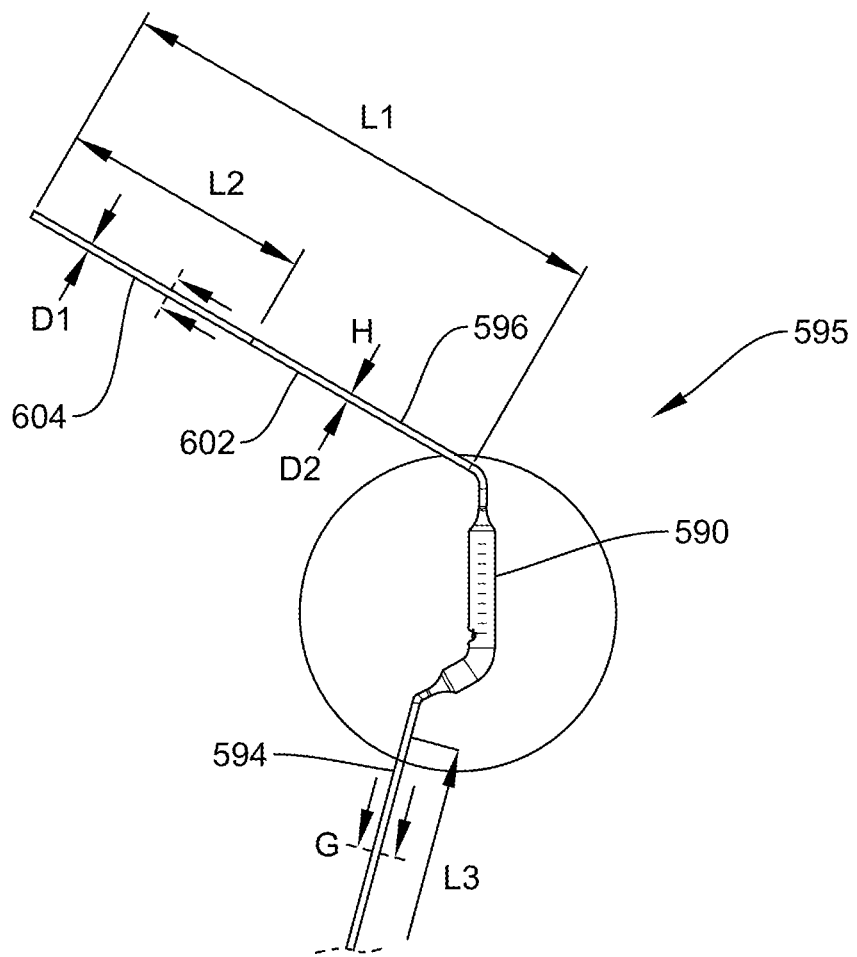
FIGS. 28A-C show the specific dimensions of a transcatheter device.
Figure 28B:
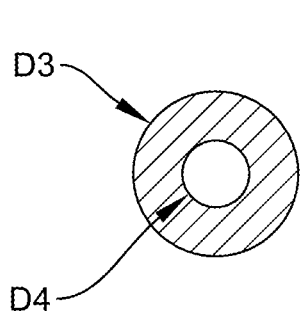
Figure 28C:
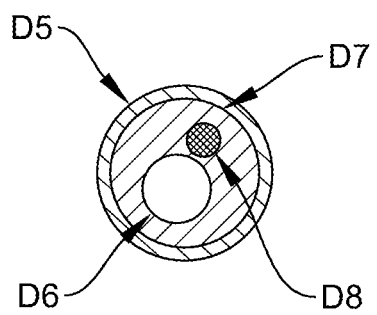

FIGS. 28A-28C show the specific dimensions of the transcatheter device 595. FIG. 28A shows the distal tail 596, which is a nitinol wire core reinforced with Pellethane braiding. The distal tail 596 further has a sheathed section 602 covered with an e-PTFE coating and an unsheathed section 604 that does not have the e-PTFE coating. The distal tail 596 has a length L1, which is about 20 cm. The unsheathed 606 has a length L2, which is about 10 cm. The sheathed section 602 has an outer diameter D2 of about 2.83 mm. The unsheathed section 604 has an outer diameter D1 of about 2.57 mm. The proximal segment 594 has a length L3, which is about 90 cm.

FIG. 28B shows a transverse cross-section view of the proximal segment 594 at line G shown in FIG. 28A. As seen here, proximal segment 594 has an outer diameter D3 of 2.43 mm. The proximal segment 594 also has a lumen, which has an inner diameter D4 of 0.99 mm. FIG. 28C shows a transverse cross-section view of the distal tail 596 at line H shown in FIG. 28A. The distal tail 596 is made with an embedded nitinol core wire having an outer diameter D8 of 0.48 mm. This core wire is reinforced with Pellethane braiding to make an outer diameter D7 of 2.17 mm. This Pellethane braiding is further coated with e-PTFE to make a total outer diameter D5 of 2.57 mm. The distal tail 596 also has a lumen with internal diameter D6 of 0.99 mm.

Figure 29A:
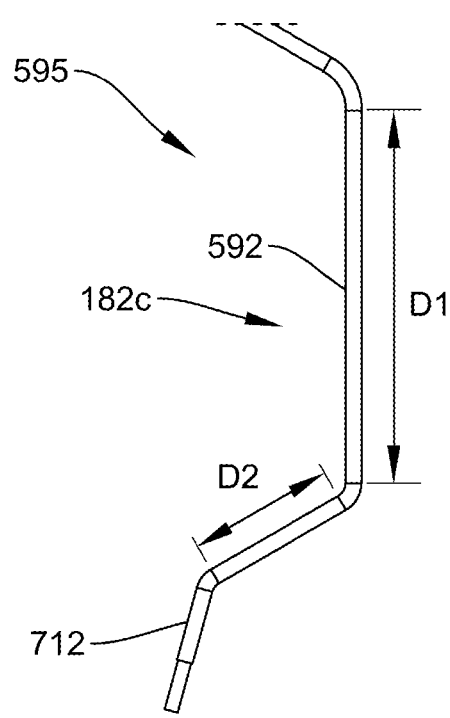
FIGS. 29A-C show further specific dimensions of a transcatheter device.
Figure 29B:
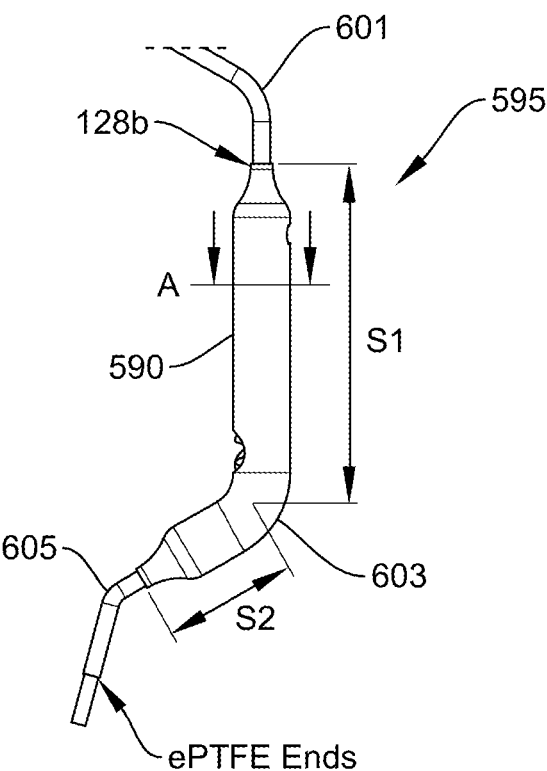
Figure 29C:
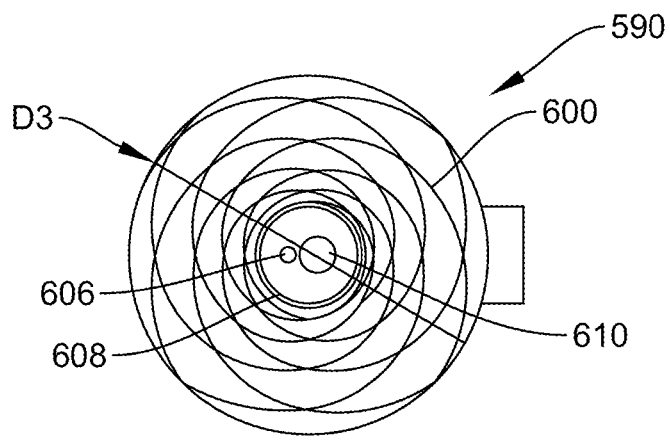

FIGS. 29A-29C show further specific dimensions of the transcatheter device 595. FIG. 29A shows the main shaft 592 omitting the spacer body 590. The inner angle at the bend 601 in the main shaft 592 as it converts to the distal tail 596 is 120°. This bend 601 has a radius of curvature of 10 mm. The outer angle in the bend 603 at the curve in the boot-shaped spacer body 590 is 240°. The inner angle of the bend 605 in the main shaft 592 as it converts to the proximal segment 594 is 135°. This bend 605 has a radius of curvature of 5 mm.

FIG. 29B shows the various lengths of the transcatheter device 595 with the spacer body 590 mounted on the main shaft 592. The length 51 represents the straight portion of the spacer body 590 and is 6 cm long, in its non-extended configuration. The distal end of spacer body 590 slides forward on the main shaft 592 when externally compressed inside a delivery sheath. The length S2 represents the bent arm portion of the spacer body 590 and is 2.5 cm long, in its non-extended configuration. FIG. 29C shows a transverse cross-section of the spacer body 590 along line A in FIG. 29B. This view shows the inner wire frame 600, nitinol wire core 606, polymer braiding 608 around the wire core 606, and the lumen 610 for the guidewire. The outer diameter (OD) of the spacer body 590 (when the wire mesh 600 is relaxed) is in the range of 9-19 mm wide.

Figure 30A:
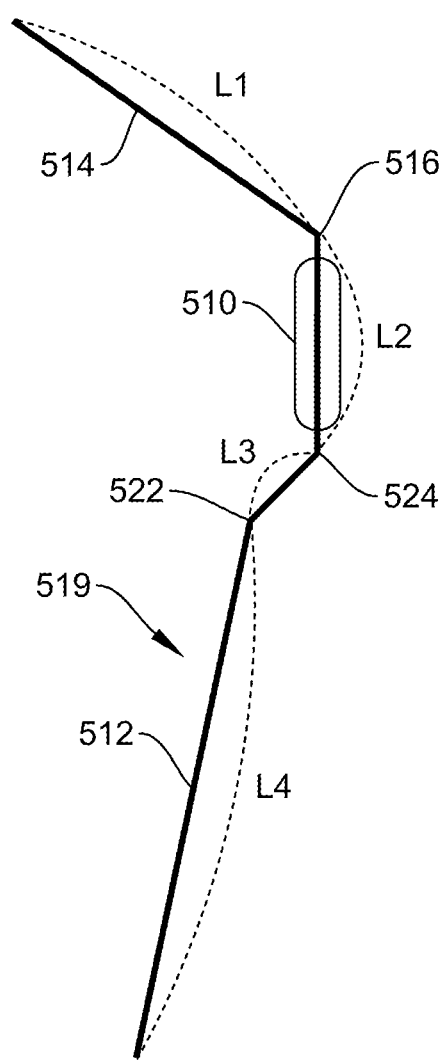
FIGS. 30A and 30B show dimensional parameters of a transcatheter device.
Figure 30B:
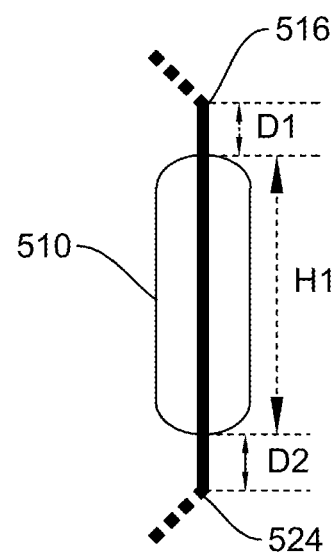

FIG. 30A shows the dimensional parameters of the transcatheter device of FIGS. 29A and B. L1 is the length of the distal tail 514. L2 is the length of the main shaft 519 encompassing the spacer body 510. L3 is the length of the proximal segment 512 between the first bend 524 and the second bend 522. L4 is the length of the proximal segment 512 of the main shaft 519 after the second bend 522. FIG. 30B shows a close-up schematic illustration for the spacer body 510. The length H1 of the spacer body 510 is in the range of 5-7 cm. The length D1 is the distance between the distal end of the spacer body 510 and the bend 516 in the distal tail 514. The length D2 is the distance between the proximal end of the spacer body 510 and the bend 524 in the proximal segment 514.

Figure 31:
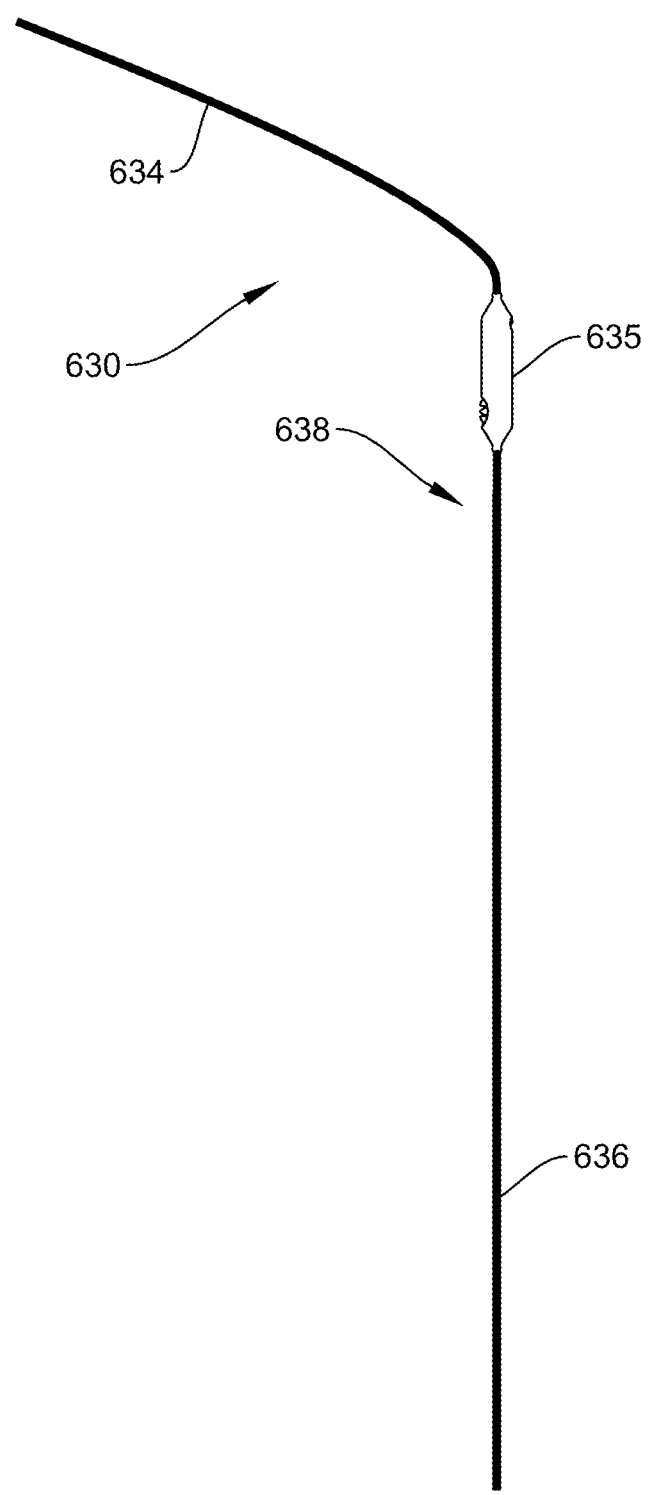
FIG. 31 shows an alternate embodiment of a transcatheter device which lacks a spiral coil at its proximal portion.
Figure 32A:
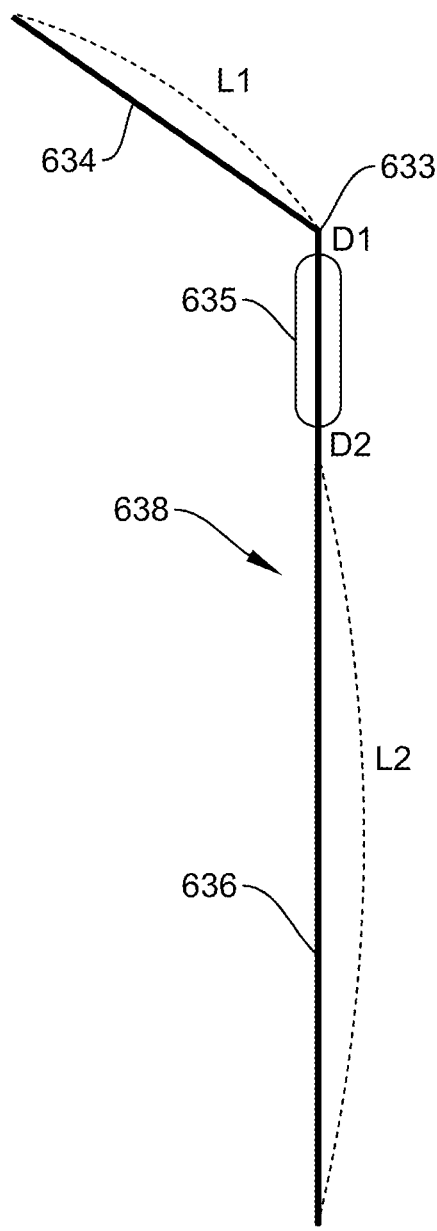
FIGS. 32A and 32B show dimensional parameters of a transcatheter device.
Figure 32B:
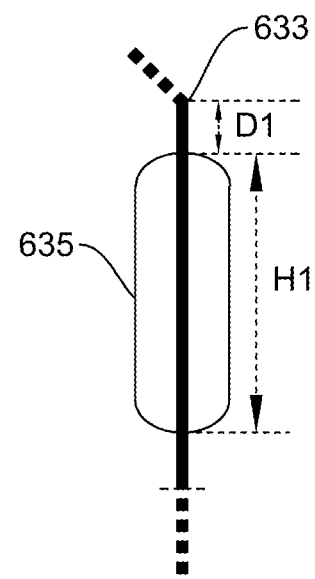

FIG. 31 shows an alternate embodiment of a transcatheter device which lacks a spiral coil at its proximal portion. This transcatheter device 630 comprises a spacer body 635, main shaft 638, distal tail 634, and proximal segment 636 of the main shaft 638. FIG. 32A shows the dimensional parameters of the transcatheter device 630. L1 is the length of the distal tail 634. As an example, L1 has a length in the range of 20-25 cm. L2 is the length of the proximal segment 636 of the main shaft 638. As an example, L2 has a length in the range of 90-120 cm. Each of these lengths represents the length along the longitudinal axis (as opposed to travel axis). FIG. 32B shows a close-up view of the schematic illustration for the spacer body 635. Bend 633 is the bend that the main shaft 638 makes as it converts to the distal tail 634. As an example, the angle at bend 633 has a range of 80-120°. The length H1 of the spacer body 635 is in the range of 5-7 cm. The length D1 is the distance between the distal end of the spacer body 635 and the bend 633 in the distal tail 634.

Figure 33A:
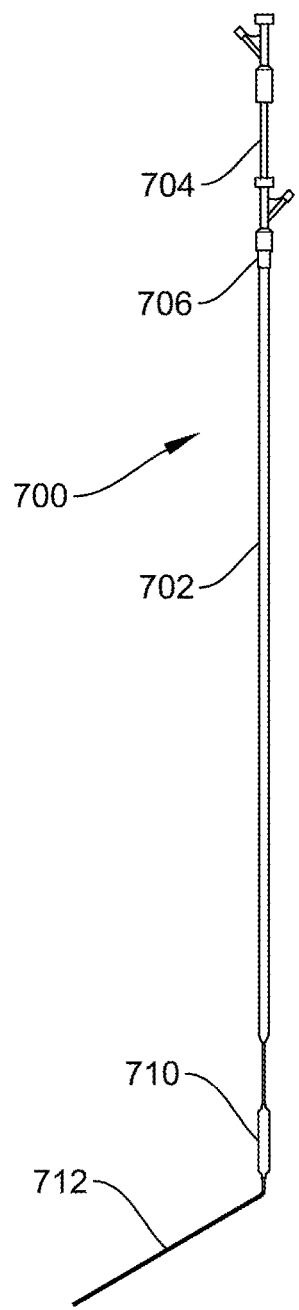
FIGS. 33A-C show a delivery catheter for a transcatheter device.
Figure 33B:
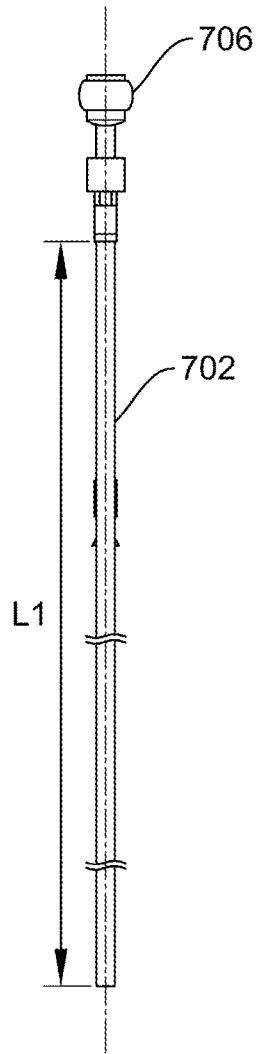
Figure 33C:
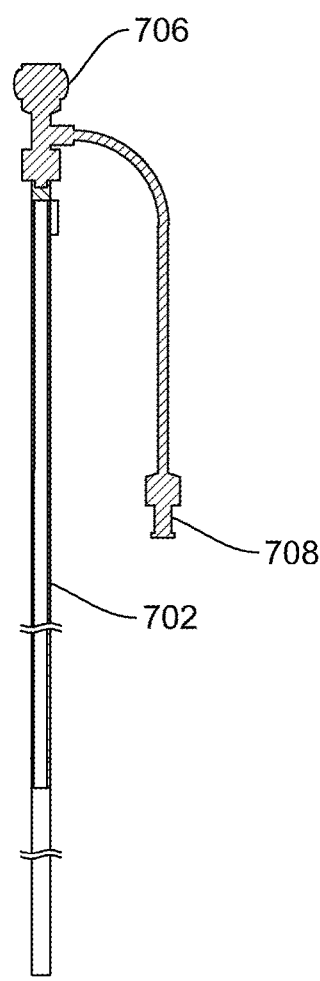

Delivery Catheter: FIGS. 33A-33C show a delivery catheter for the transcatheter device. FIG. 33A shows a side view of the transcatheter device as placed in the delivery catheter 700. Seen here are the spacer body 710 and the distal tail 712 of the transcatheter device. The delivery catheter 700 comprises a shaft 702. At its proximal end, the delivery catheter 700 has a main port 706 and a stylet 704. FIG. 33B shows close-up side view of the proximal end of the delivery catheter 700. Length L1 represents the 60 cm length of the shaft 702. The total length of the delivery catheter 700 (including the port) is about 670 mm. FIG. 33C shows a cross-sectional view of the delivery catheter 700. The outer diameter of the delivery catheter is about 5.7 mm. Shown here is also an accessory port 708.

Figure 34A:
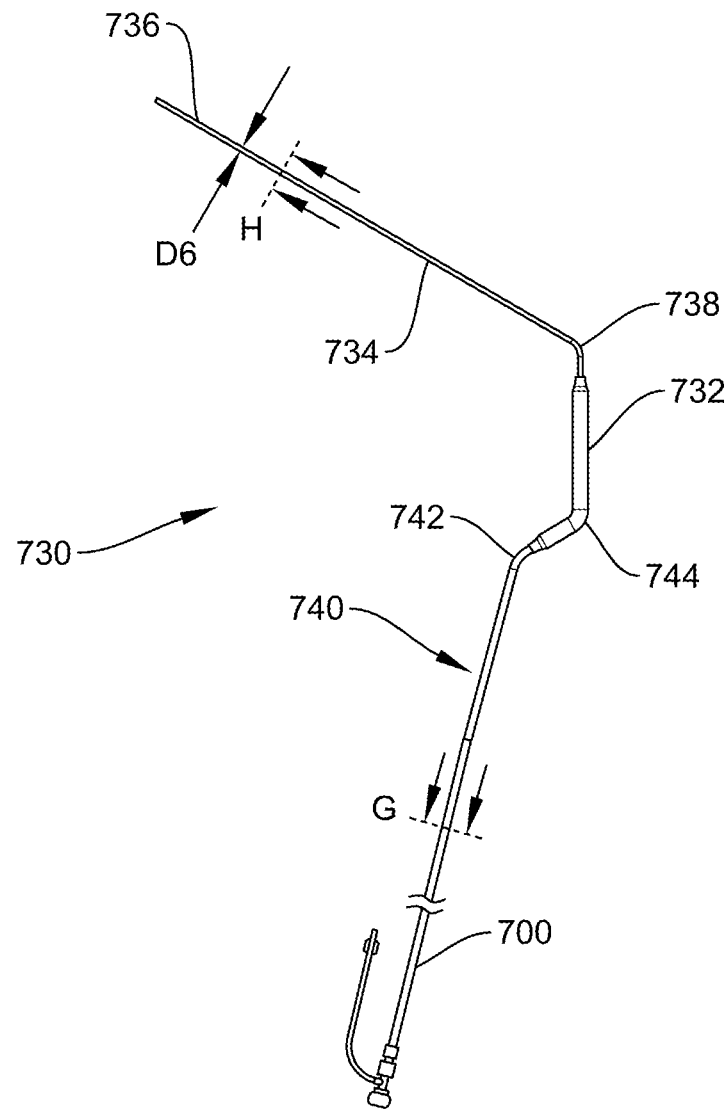
FIGS. 34A-C show another example embodiment of a transcatheter device.
Figure 34B:
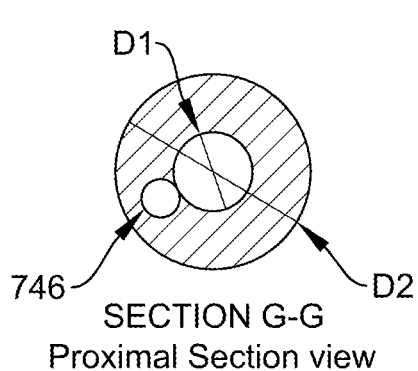
Figure 34C:
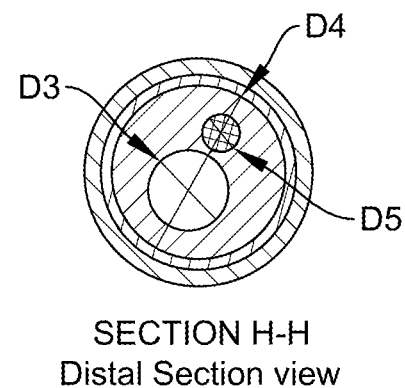

FIGS. 34A-34C show another example embodiment of the transcatheter device. FIG. 34A shows the transcatheter device 730 comprising a balloon-type boot-shaped spacer body 732, a distal tail 734, and proximal segment 740 of the main shaft. The distal tail 734 has a bend 738. The distal tail 734 has a distal segment 736 (of 2 cm length) that is not supported by a nitinol core wire. That is, the nitinol core wire ends before reaching the distal tip of the distal tail 734. The absence of the nitinol wire at the distal portion could be useful for having more flexibility for the distal tail 734 so that it could advance further into the pulmonary artery tree. The inner angle at the bend 738 is 120°. The spacer body 732 also has a bend 744 take makes the spacer body 732 curve-shaped. The inner angle at the bend 744 is 120°. There is a bend 742 where the main shaft converts to the proximal segment 740. The inner angle at bend 742 is 110°. Spacer body 732 is designed as an inflatable balloon.

Also shown in FIG. 34A is the delivery catheter 700 for deploying the transcatheter device 730 into the patient's heart. FIG. 34B shows a transection view of the delivery catheter 700 at line G on FIG. 34A. Shown here are the lumen for the guidewire having inner diameter D1 (0.99 mm) and an air supply port 746, through which the spacer body 732 balloon is inflated and deflated. The outer diameter (D2) of the delivery catheter 700 is 2.43 mm. FIG. 34C shows a transection view of the distal tail 734 along line H, which has a nitinol wire core with a diameter (D5) of 0.48 mm. It also has a guidewire lumen with a diameter (D3) of 0.99 mm. The Pellethane braiding around the nitinol wire gives a diameter (D4) of 2.17 mm. There is also a thin e-PTFE coating around the Pellethane braiding.

Figure 35A:
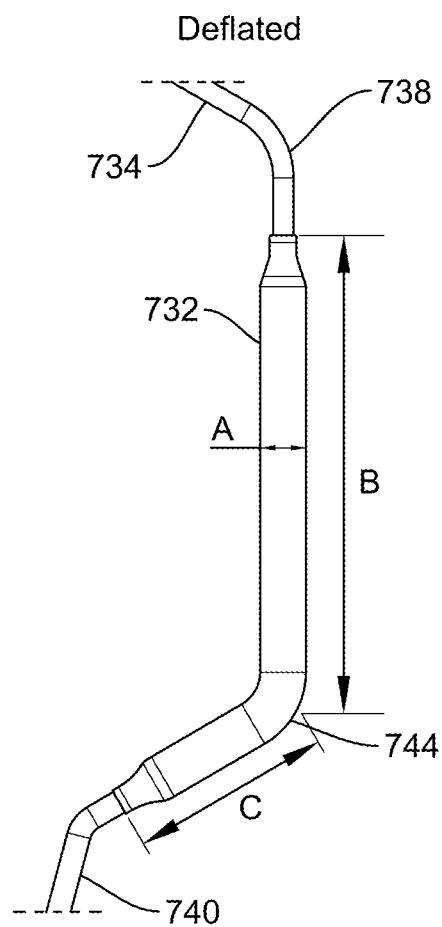
FIGS. 35A and 35B show further specific dimensions of a transcatheter device
Figure 35B:
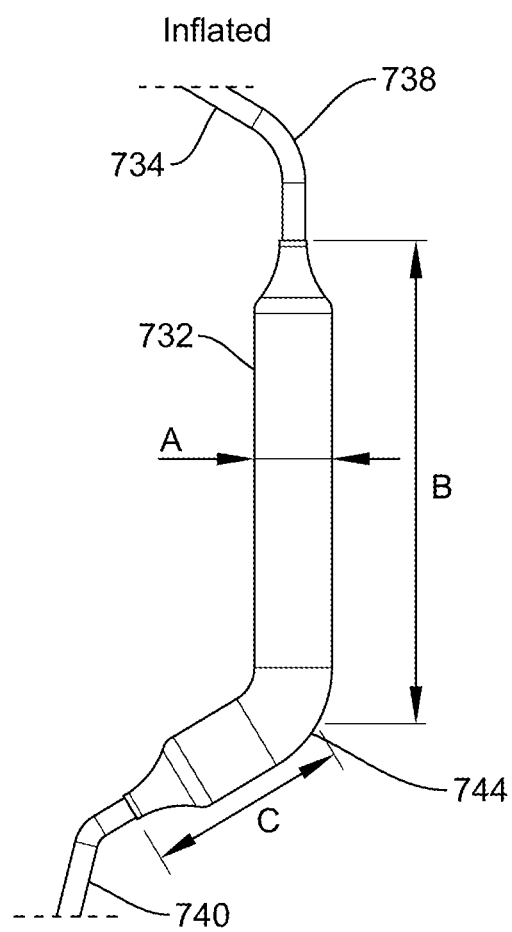

FIGS. 35A and 35B show further specific dimensions of the transcatheter device 730. The travel length of the bend 738 in distal tail 734 is about 10 mm. The travel length of the bend 744 on the proximal segment 740 of the main shaft is about 5 mm. FIG. 35A shows the balloon-type spacer body 732 in uninflated configuration. FIG. 35B shows the balloon-type spacer body 732 in inflated configuration. See that the width of the spacer body 732 is expanded after inflation. For a spacer body that is supported by an expandable internal scaffold, FIGS. 35A and 35B could alternatively show the spacer body in a constrained configuration and a relaxed configuration, respectively.

Figure 36A:
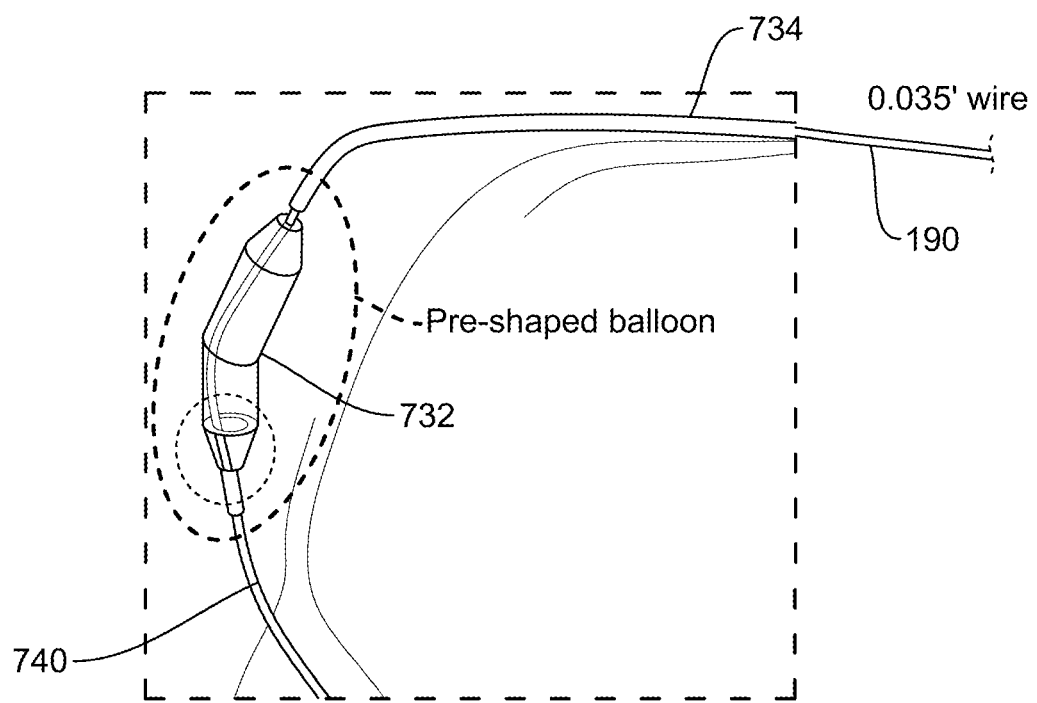
FIG. 36A-C show a prototype of a transcatheter device.
Figure 36B:
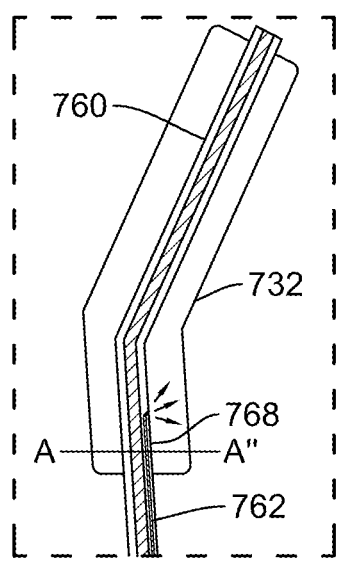
Figure 36C:
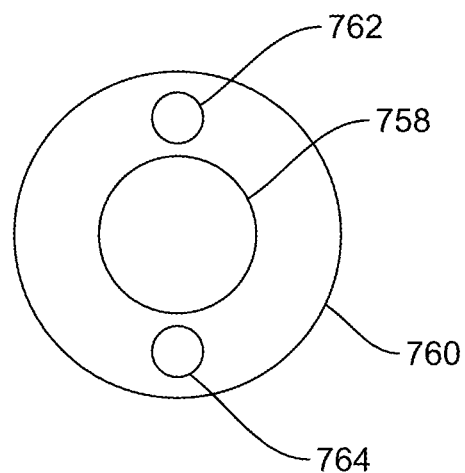

FIG. 36A shows a prototype of the transcatheter device 730 with spacer body 732 inflated and with guidewire 190 inserted. FIG. 36B shows a transection view along line B of FIG. 36B. Seen here is the main shaft 760 having a main lumen for the guidewire. There is also an accessory channel 762 for supplying air or saline to the balloon-type spacer body 732. The air or saline flows through hole 768 in the main shaft 760 to inflate/deflate the balloon-type spacer body 732. FIG. 36C shows a cross-section view along line A of FIG. 35B. Seen here is the main shaft 760 having a main lumen 758 and the accessory channel 762. There is also a nitinol wire core 764 for rigid support of the main shaft 760.

Figure 37A:
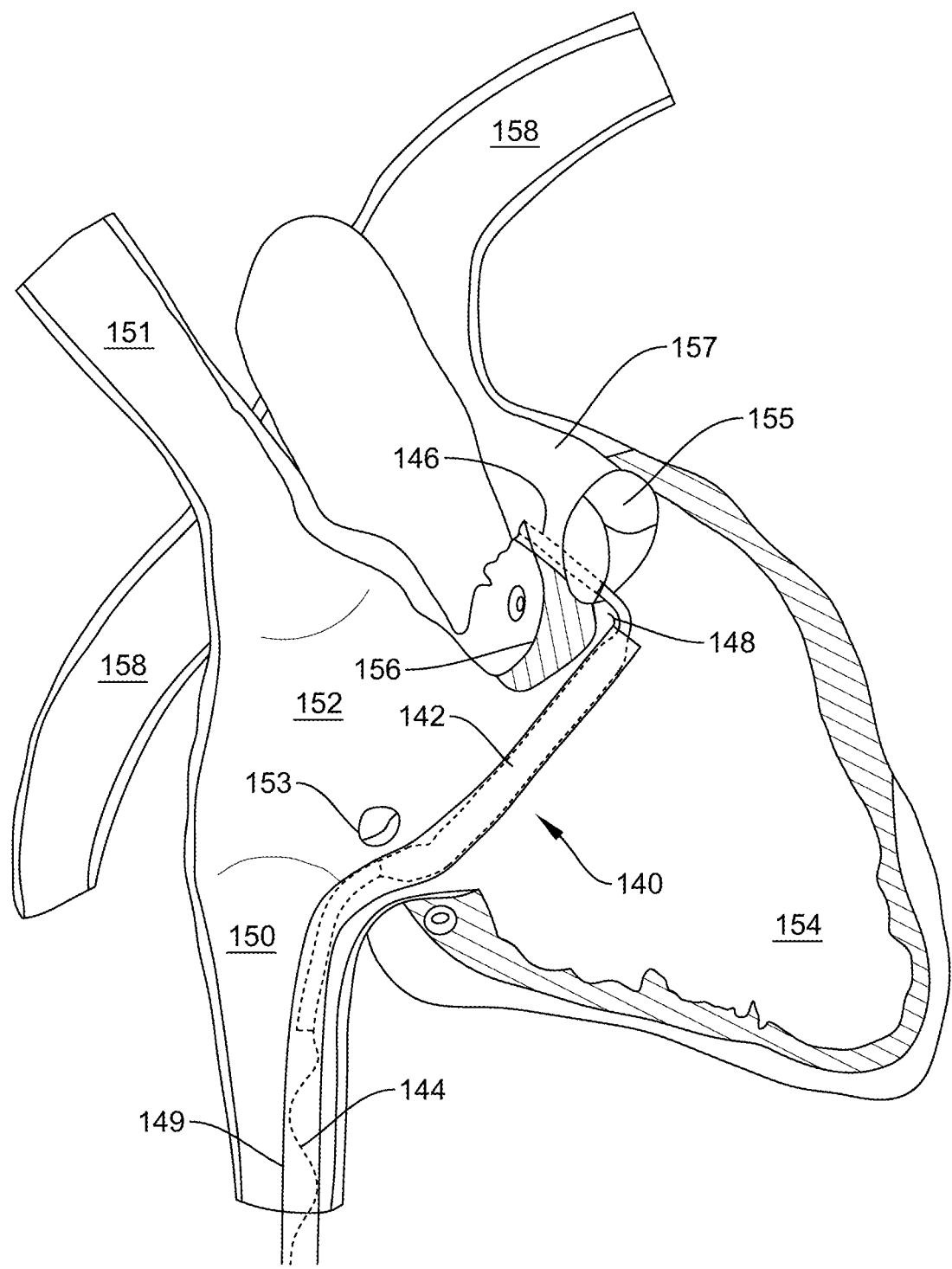
FIGS. 37A-D show another embodiment of the transcatheter device.

FIGS. 37A-37D show another embodiment of the transcatheter device. These illustrations show transcatheter device 140 being installed in the patient's heart. Shown are the inferior vena cava 150, superior vena cava 151, right atrium 152, coronary sinus 153, right ventricle 154, pulmonary artery valve 155, supraventricular crest 156, main trunk 157 of the pulmonary artery, and the two branches 158 of the pulmonary artery. FIG. 37A shows the transcatheter device 140 being deployed via a delivery sheath 149. The spacer body 142 and the spiral coil 144 are held inside the delivery sheath 149. Constrained inside delivery sheath 149, spiral coil 144 is in compressed configuration such that it stretches out along its longitudinal axis. Note that spacer body 142 comprises a small barbed hook 148 at its distal end, which is held in retracted position by the delivery sheath 149.

Figure 37B:
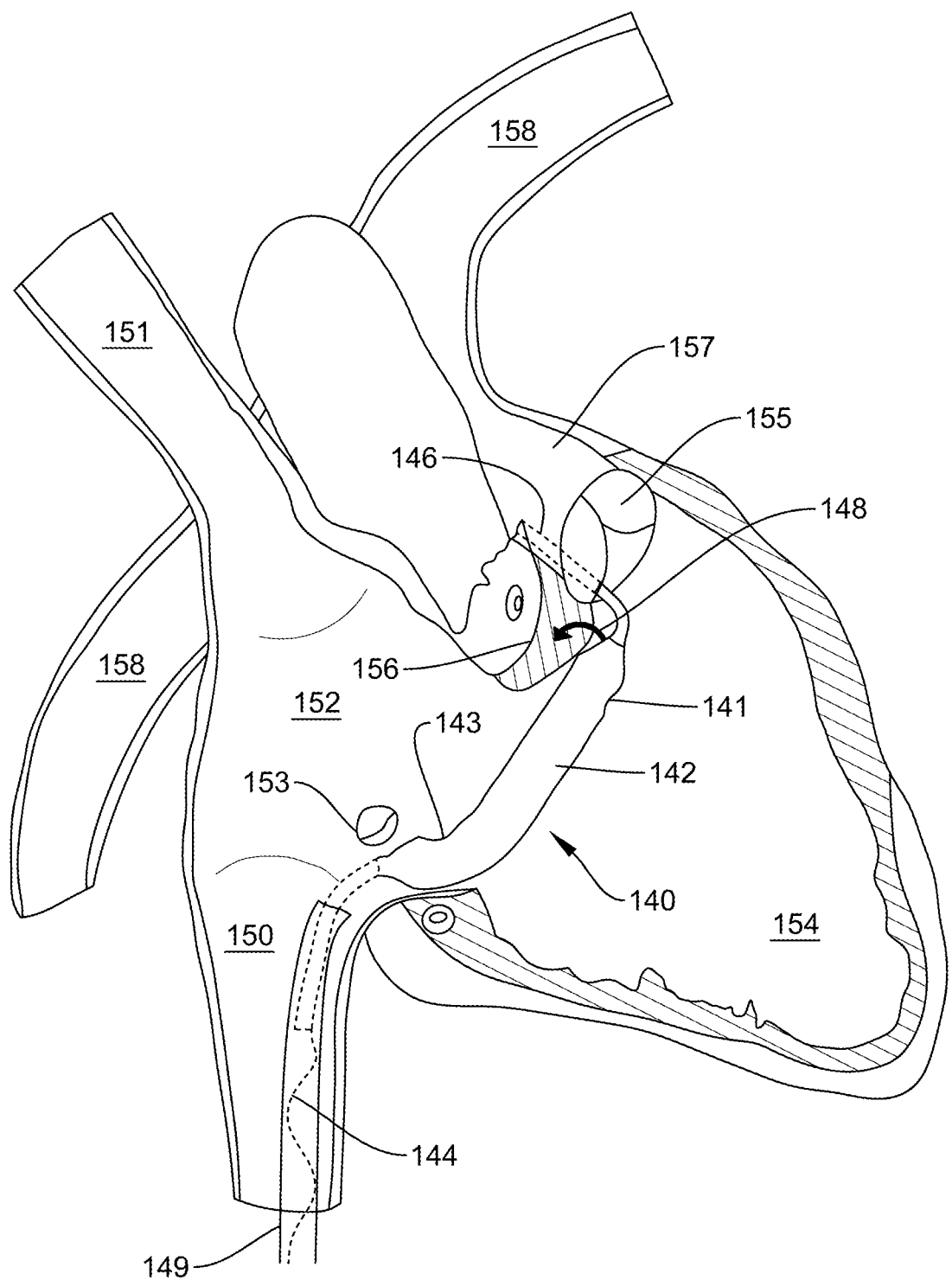

The distal tail 146 extends out from the delivery sheath 149 and traverses across the pulmonary artery valve 155 and into the main trunk 157 of the pulmonary artery. Note that distal tail 146 does not extend into the branches 158 of the pulmonary artery. Having a hook 148 could allow the distal tail 146 to be relatively shorter in length. For example, the length of distal tail 146 could be in the range of 5-25 cm long; and in some cases, 5-15 cm long. FIG. 37B shows the hook 148 being deployed. As the delivery sheath 149 is retracted backwards, the hook 148 emerges and springs out in its pre-biased jutting-out configuration.

Figure 37C:
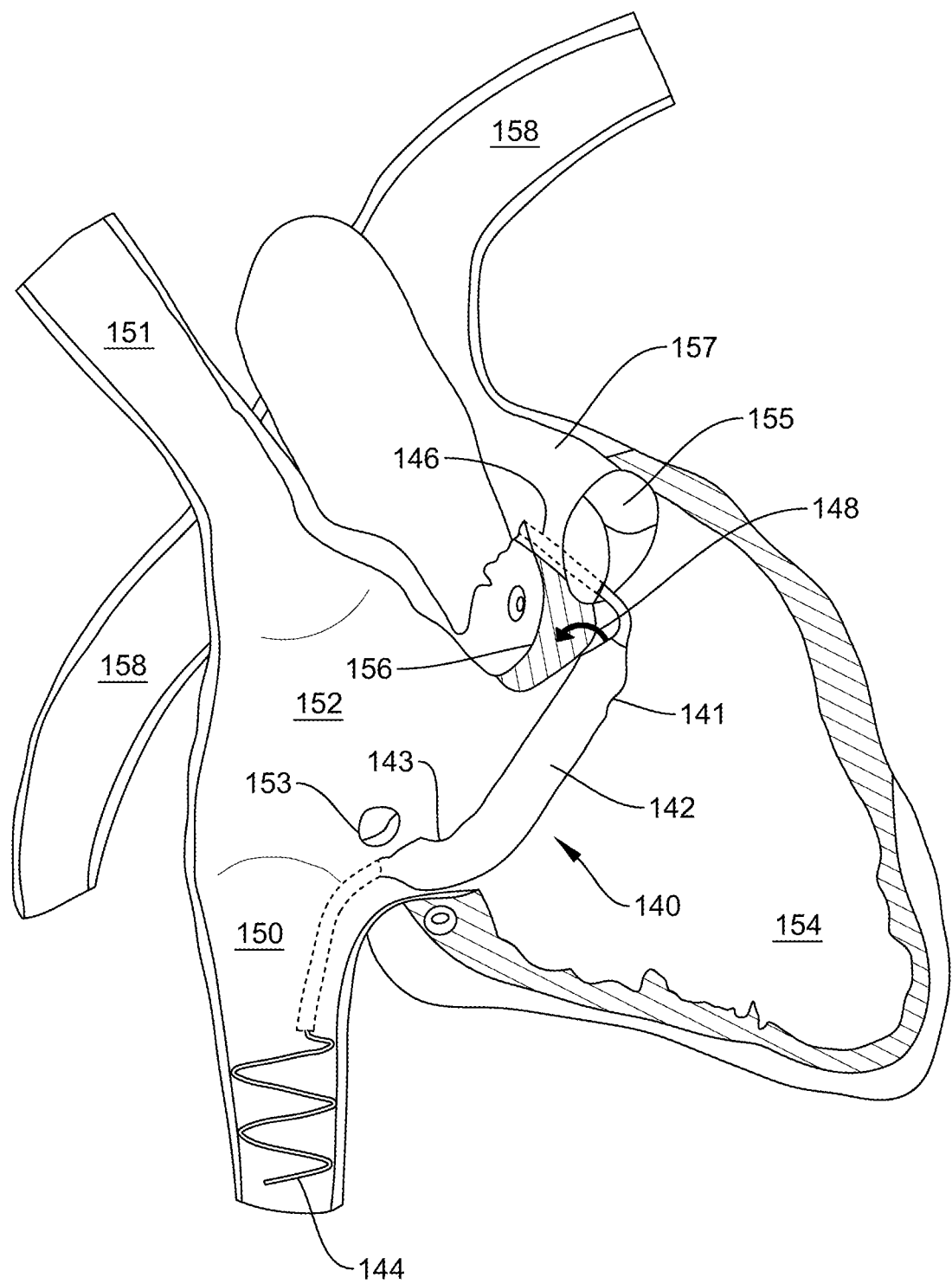

The force of hook's 148 spring-like action may be sufficient to embed the hook 148 into the supraventricular crest 156. The spacer body 142 could also be pulled back slightly to help embed the hook 148 into the supraventricular crest 156. Thus, the distal part of spacer body 142 is anchored close to the supraventricular crest 156. This improves the stability of the spacer body 142 in correct position in relation to the tricuspid valve. In FIG. 37C, the delivery sheath 149 is fully withdrawn so that the spiral coil 144 expands outward and becomes lodged within the inferior vena cava 150. FIG. 37C also shows the orientation of hook 148 being positioned on the opposite side of distal hole 141, but on the same side as proximal hole 143 and the direction of the boot portion of spacer body 142.

Figure 37D:
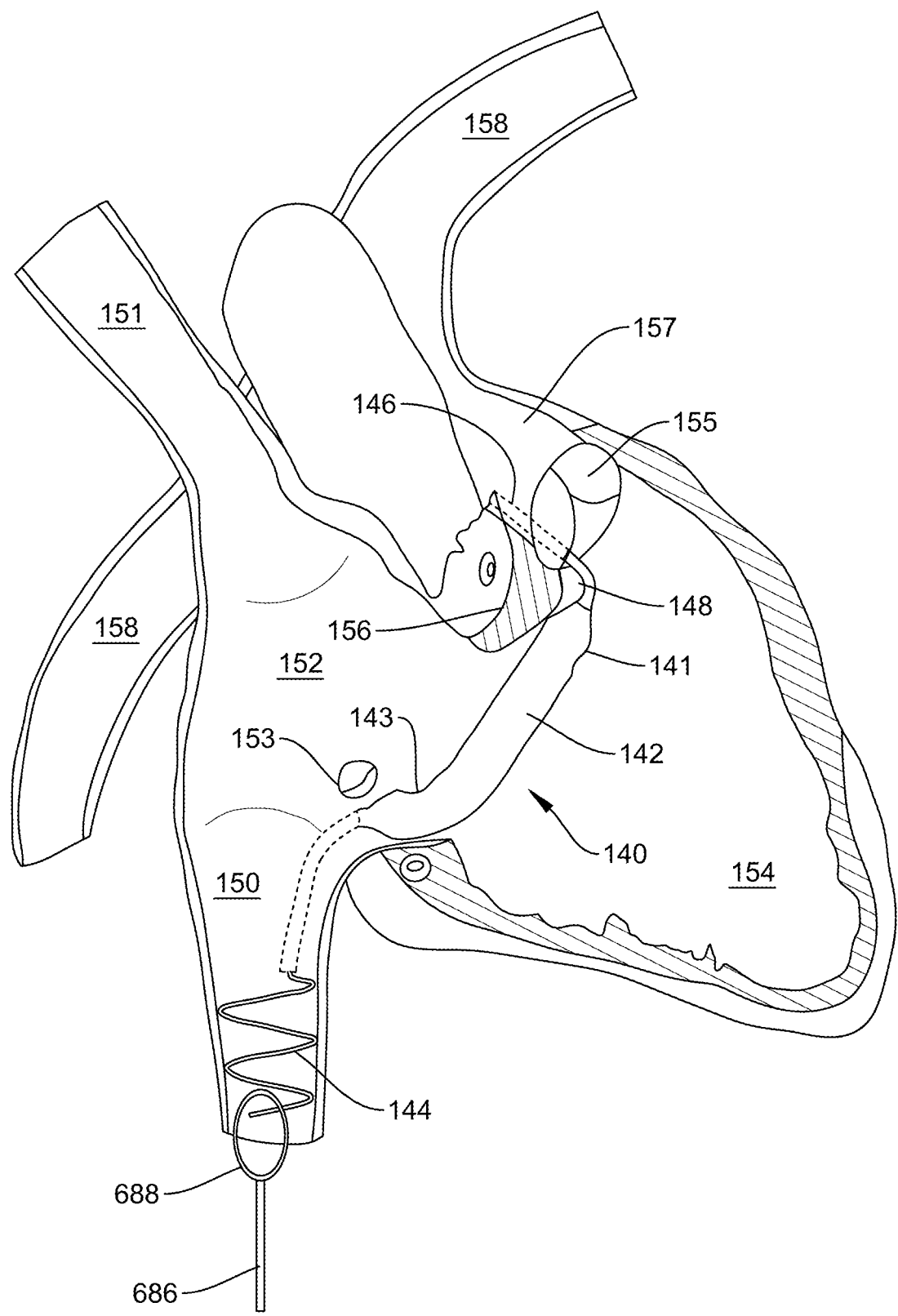

FIG. 37D shows how a transcatheter device could subsequently be removed by a retrieval procedure. Note, this is for an alternate transcatheter device design without the hook 148 described above. This involves the use of a snare catheter 686, which has a snare loop 688. The snare catheter 686 is inserted through a femoral vein and advanced up towards the inferior vena cava 150 under x-ray fluoroscopic guidance. The snare catheter 686 is manipulated so that the snare loop 688 ensnares the distal end of the spiral coil 144. The snare catheter 686 is then withdrawn to remove the entire transcatheter device 140 out of the patient's body.

Figures 38A, 38B:
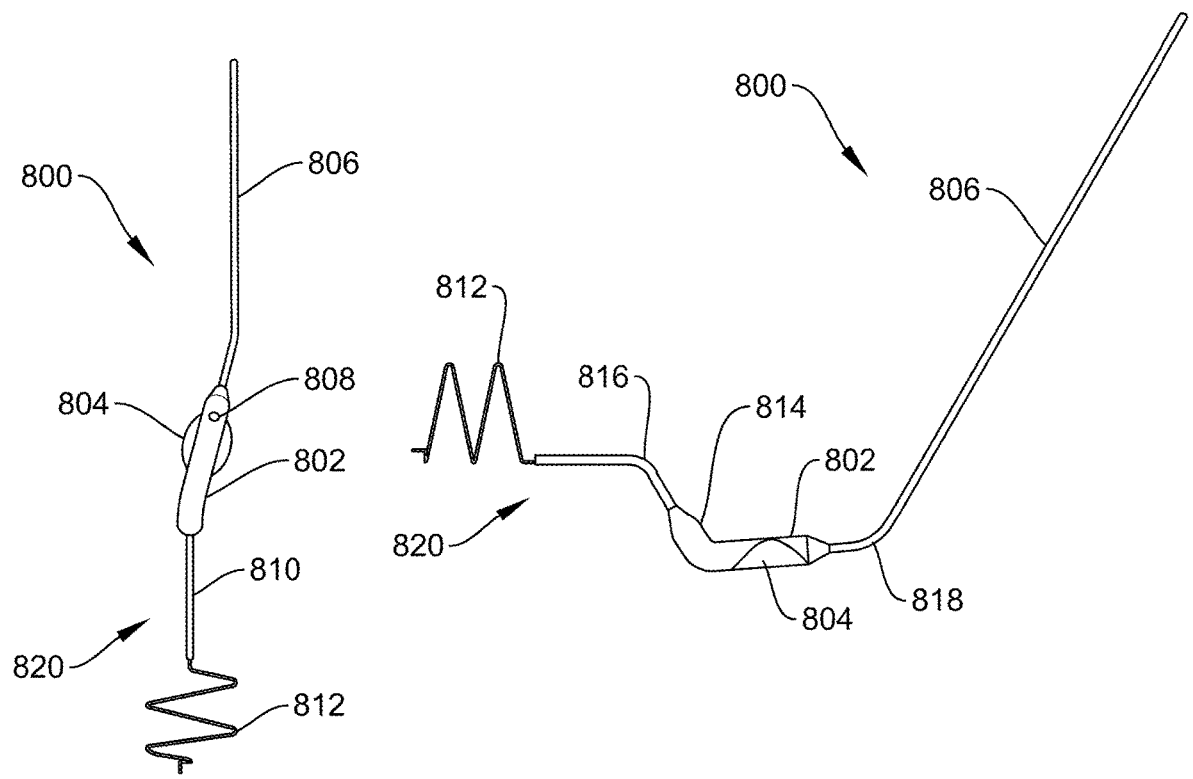
FIGS. 38A-C show another embodiment of the transcatheter device.
Figure 38C:
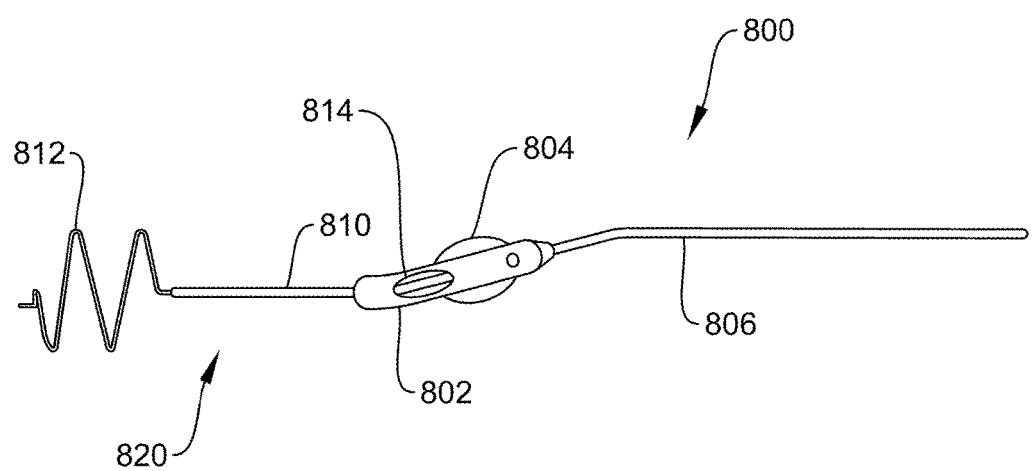

FIGS. 38A-C show another example of a transcatheter device for treating a defective tricuspid valve. Transcatheter device 800 has a distal tail 806 and a proximal portion 820. In between the distal tail 806 and the proximal portion 820 is a spacer body 802 having wings 804. The proximal portion 820 of the transcatheter device 800 comprises a spiral coil 812. A main shaft 810 encompasses the proximal portion 820 of the transcatheter device 800, through spacer body 802, and the distal tail 806 of the transcatheter device 800. As seen in FIG. 38A (bottom view), there is a small distal opening 808. As seen in FIG. 38B (side view), there is a bend 816 at the proximal portion 820 of main shaft 810, and a bend 818 at the distal tail 806. As seen in FIG. 38C (top view), there is a larger proximal opening 814 in spacer body 802.

Figure 39:
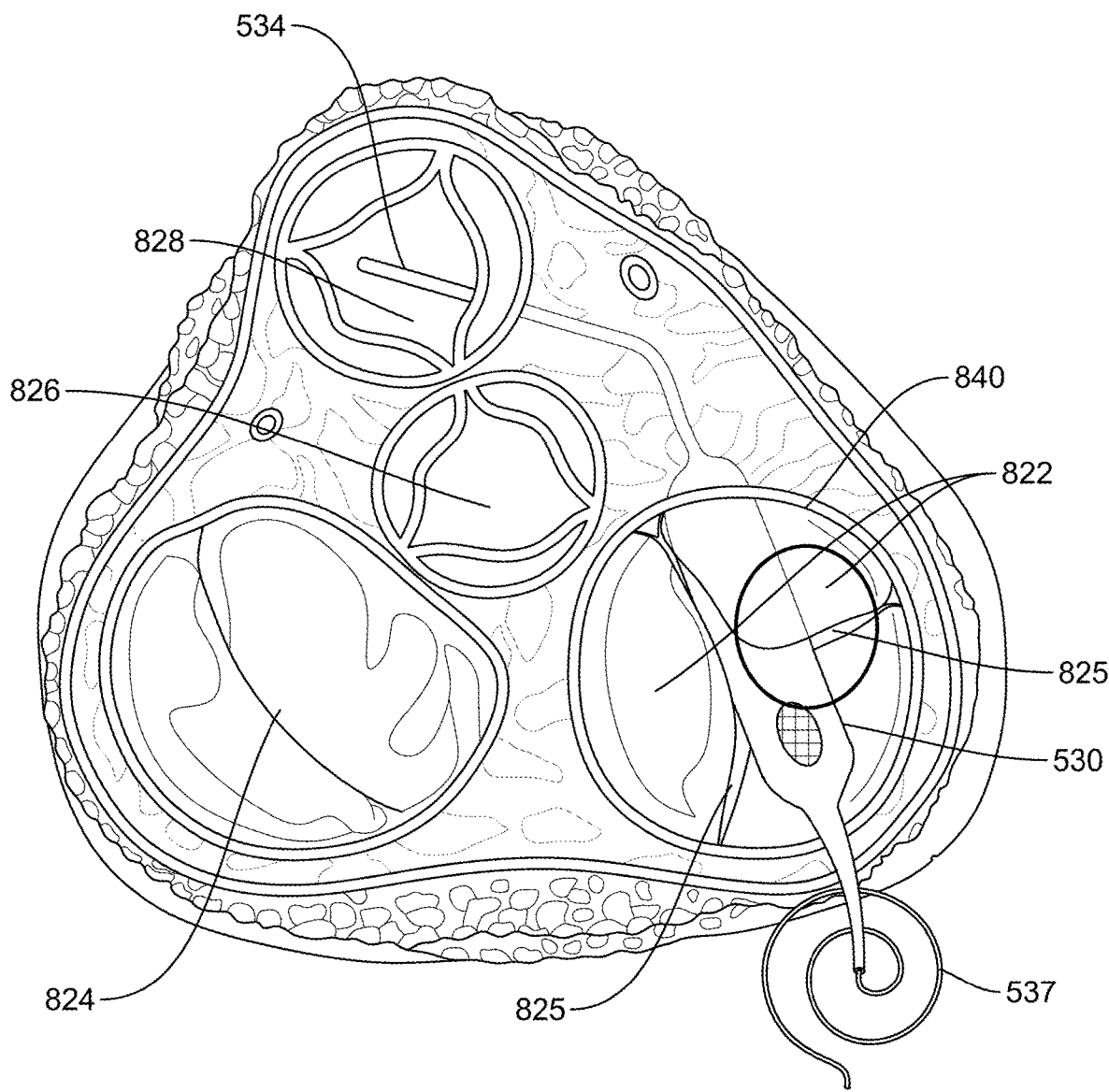

In this example embodiment, the spacer body 802 has a cylindrical boot shape. The spacer body 802 also has a pair of wings 804, which work to improve coaptation of the spacer body 802 to the tricuspid valve leaflets. FIGS. 39, 40A and B, and 41A and B show how this works. FIG. 39 shows the spacer body 530 of FIG. 22A traversing across the tricuspid valve 840 with its three leaflets 822. Also shown are the mitral valve 824, pulmonary valve 828, and aortic valve 826. At the tricuspid valve 840, the spacer body 530 provides good coaptation with the valve leaflets 822. However, there are still gaps 825 between the sides of the leaflets 822 that may allow regurgitation to persist.

FIGS. 40A and B show how the wings 804 help to close these gaps 825. FIG. 40A shows the tricuspid valve 840 in closed configuration during ventricular systole. The pressure from the right ventricle causes the wings 804 to open into spread-out configuration. In this configuration, wings 804 work to reduce the gaps 825 between the valve leaflets 822. This improves the coaptation of spacer body 802 to the valve leaflets 822. FIG. 40B is an axial end-on view of the spacer body 802 in isolation with the wings 804 in spread-out configuration.

FIGS. 41A and B show how the wings 804 fold inward. During ventricular diastole, the tricuspid valve 840 opens to allow blood to flow from the right atrium into the right ventricle. This blood flow causes the wings 804 to fold inward into a compact configuration. This reduces interference that the wings 804 may cause against this flow of blood into the right ventricle. FIG. 41B is an axial end-on view of the spacer body 802 in isolation with the wings 804 in folded-down configuration.

Figure 42A:
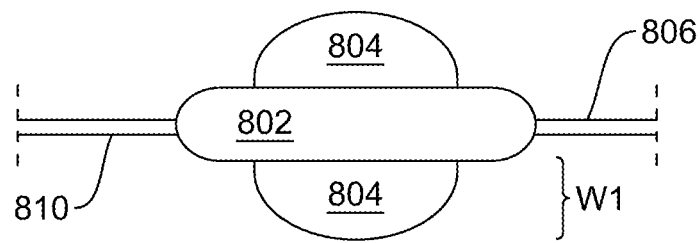
FIGS. 42A-C are schematic illustrations that show the possible dimensions of the spacer body and wings.
Figure 42B:
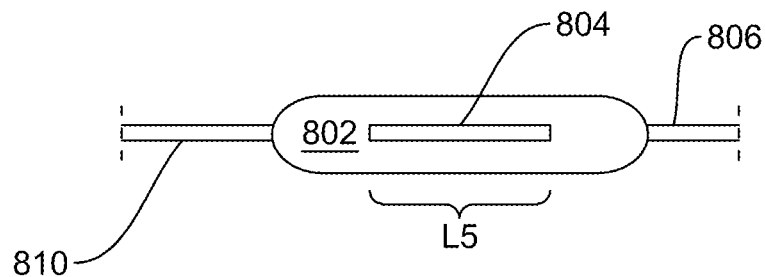
Figure 42C:
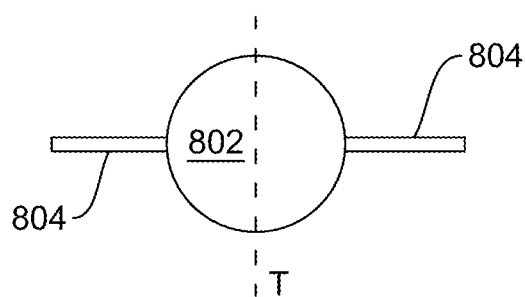

FIGS. 42A-C are schematic illustrations that show the possible dimensions of the spacer body and wings. As seen in FIG. 42A (top view), the width of the wings are sufficiently wide to reduce gaps between the tricuspid valve leaflets. In some embodiments, the width W1 of the wing 804 is 0.1-3.5 cm; and in some cases, 0.5-2.5 cm. As seen in FIG. 42B (side, edge-on view), the length of the wing 804 is shorter than the length of the spacer body 802. In some embodiments, the length L5 of the wing 804 (measured as its longest length along the longitudinal axis of the spacer body 802) is 2-9 cm; and in some cases, 3-6 cm. As seen in FIG. 42C (axial end-on view), the thickness of the wing 804 is less than the thickness of the spacer body 802. In some embodiments, the thickness of the wing 804 (as measured along the transverse axis T that is orthogonal to the wing and the longitudinal axis of the spacer body) is 0.5-10 mm; and in some cases, 0.5-6 mm.

Figure 43:
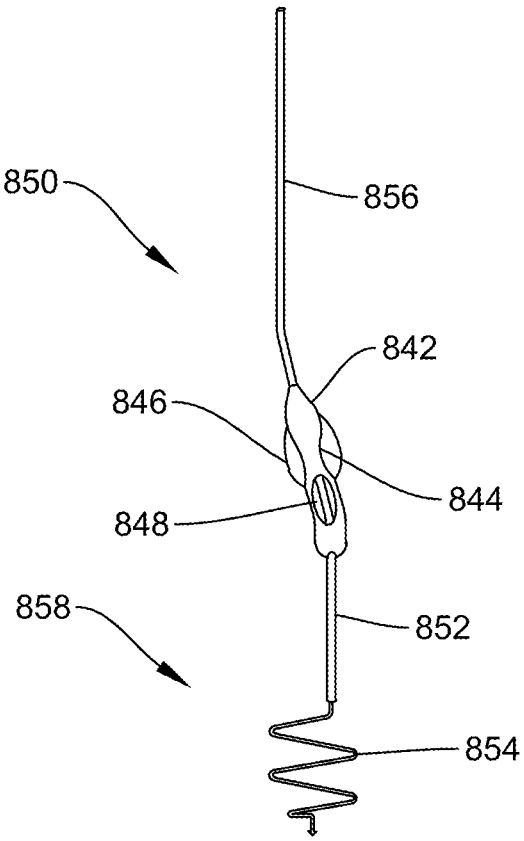
FIG. 43 shows another example of a transcatheter device with wings on the spacer body.

FIG. 43 shows another example of a transcatheter device with wings on the spacer body. Transcatheter device 850 has a distal tail 856 and a proximal portion 858. In between the distal tail 856 and the proximal portion 858 is a spacer body 842. Here, the spacer body 842 has an hourglass shape with a thinner waist 844 near the middle. At this waist 844, there are two wings 846. The proximal portion 858 of the transcatheter device 850 comprises a proximal segment 852 of the main shaft and a spiral coil 854. Also shown is a proximal opening 848 on the spacer body 842.

FIGS. 44A-C show another example of a transcatheter device with multiple smaller winglets on the spacer body. Transcatheter device 860 has a distal tail 866 and a main shaft with a proximal segment 870 thereof. In between the distal tail 866 and the proximal segment 870 is a spacer body 862. Here, the spacer body 862 has three small winglets 864 on each side, for a total of six winglets 864. As shown in FIG. 44A (bottom view), the transcatheter device 860 comprises a spiral coil 872 and a distal hole 868 on spacer body 862. As shown in FIG. 44B (top view), spacer body 862 also has a proximal hole 874. FIG. 44C is a side view of the transcatheter device 860 showing two bends in the main shaft.

FIGS. 45A-C show another example of a transcatheter device with a different design for the spacer body. Transcatheter device 880 has a spiral coil 888, a distal tail 886, and a main shaft with a proximal segment 884 thereof. In between the distal tail 886 and the proximal segment 884 is a spacer body 882. Here, the spacer body 882 is designed to work in a parachute-like manner. FIG. 45A is a top view of the transcatheter device 880 showing an overhead view of the canopy 890 for spacer body 882. FIG. 45B is a bottom view showing an underside view of the canopy 890. Shown here are the multiple strings 892 that are attached to the periphery of canopy 890. FIG. 45C is a side view of the transcatheter device 880 showing how the strings 892 and tether 894 are attached. At one end, the strings 892 are attached to the periphery of canopy 890 and to the tip of the tether 894 at the other end. The tether 894 is attached to the main shaft.

FIG. 46 is a perspective view of the transcatheter device 880 showing the spacer body 882 in deployed configuration. Shown here, the canopy 890 is swollen in distended configuration. The canopy 890 shape is held together by the strings 892 that are attached to the tether 894.

FIGS. 47A and B are illustrations of the tricuspid valve shown as a schematic model from a side view. Shown here is the spacer body 882 of transcatheter device 880 in operation when installed in the tricuspid valve. FIG. 47A shows the tricuspid valve in closed configuration during ventricular systole, with ventricular pressure in the direction of arrow F1. This fluid pressure causes the canopy 890 to swell open and abut against the valve leaflets 822 to provide coaption of the spacer body 882 to the tricuspid valve. The shape of canopy 890 is held by the strings 892 that are attached to the tether 894, which is attached to the main shaft 896 of the transcatheter device 880. In FIG. 47B, the arrows F2 show the blood flow during ventricular diastole from the right atrium into the right ventricle. This blood flow causes the canopy 890 to collapse inward into a compact configuration. This reduces interference that canopy 890 may cause against this flow of blood into the right ventricle.

Figure 48A:
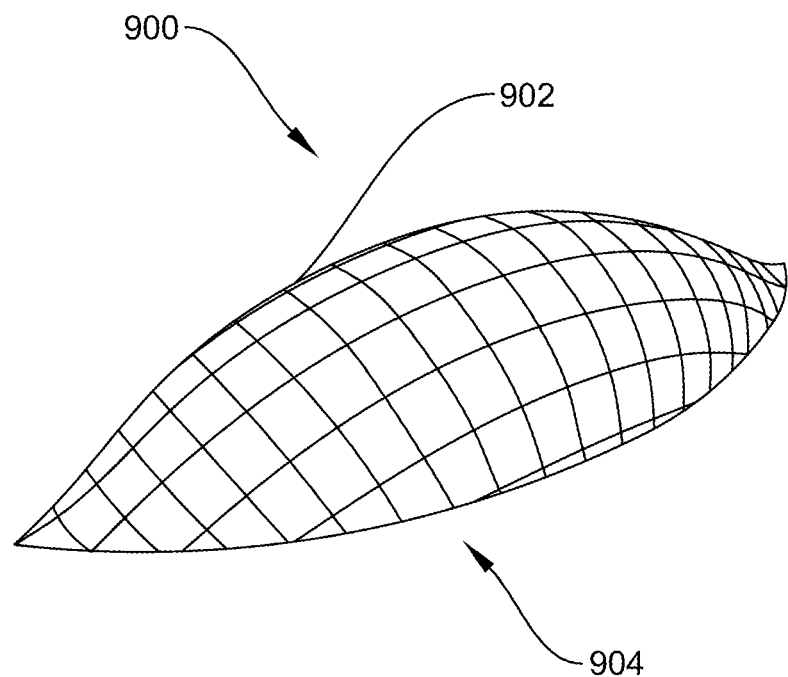
FIGS. 48A and 48B show another example of a wing design that could be used for the spacer body.
Figure 48B:
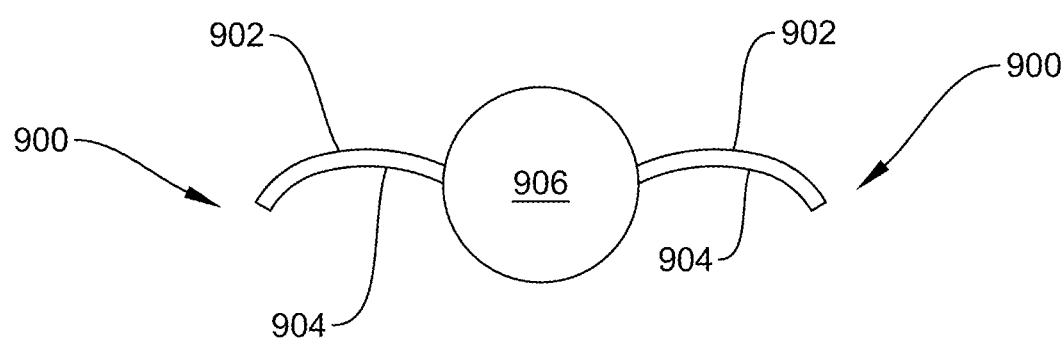

FIGS. 48A and B show another example of a wing design that could be used for the spacer body. FIG. 48A is a perspective view of the wing 900 in isolation. The wing 900 has a boat shape with a convex outer side 902 and a concave inner side 904. The gridlines are added to better illustrate the three-dimensional shape. FIG. 48B is a cross-section view of the transcatheter device with spacer body 906 and boat-shaped wings 900. This view helps to illustrate the curvature of wing 900 with its convex outer side 902 and its concave inner side 904. In actual use, the inner side 904 would face towards the right ventricle. This shape may be useful in improving the flapping response of the wing 900 to flow of blood.

Figure 49A:
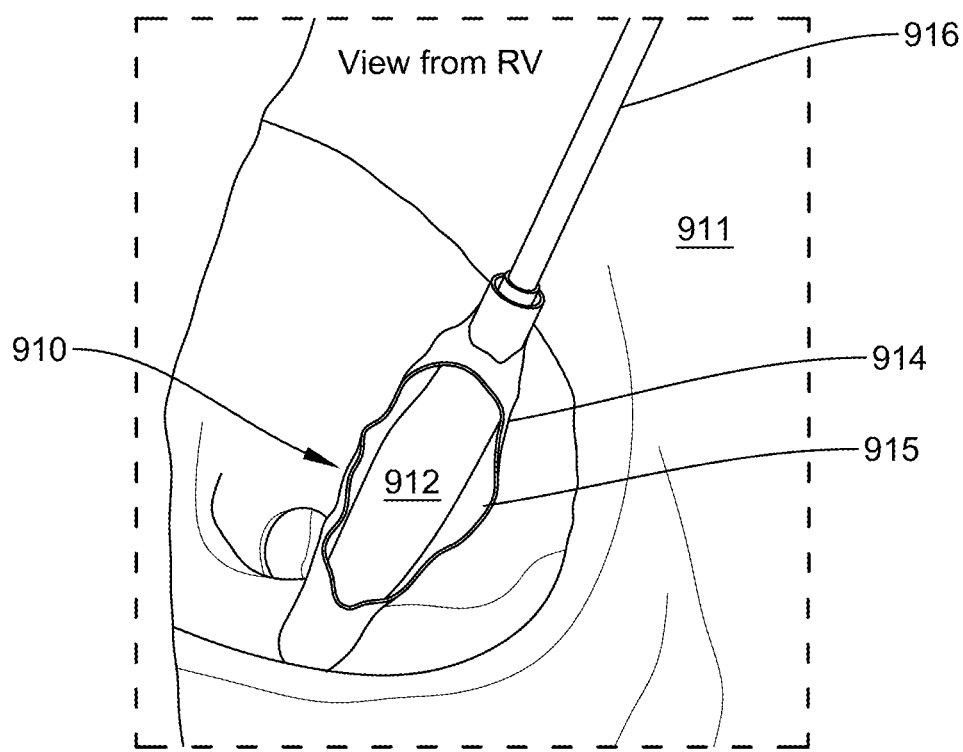
FIGS. 49A and 49B show another example of a transcatheter device with a shroud on the spacer body.
Figure 49B:
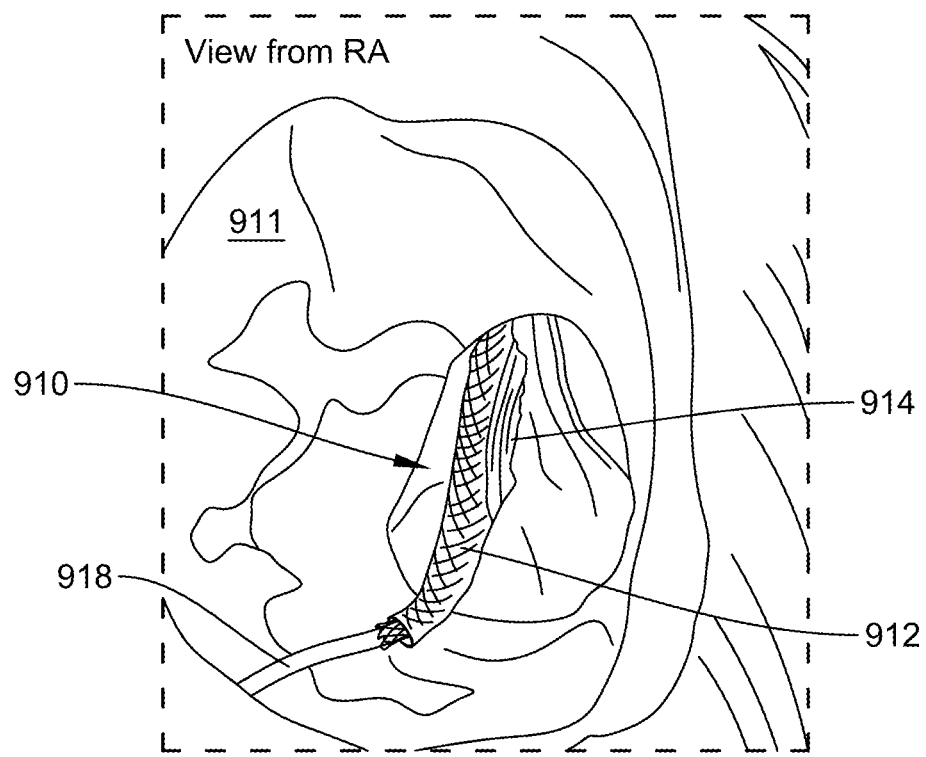

FIGS. 49A and B show another example of a transcatheter device with a shroud on the spacer body. The transcatheter device is shown in the context of an artificial silicone plastic model 111 of the human heart. FIG. 49A shows a bottom view (from the perspective inside of the artificial right ventricle) of the transcatheter device having a distal tail 916 and spacer body 910. The main hull 912 of spacer body 910 is contained within a shroud 914. The shroud 914 has edge flaps 915 that work in a similar manner to the wings described above, having an open configuration and a closed configuration. The shroud 914 also has an inherent curvature that may improve the flapping response of the edge flaps 915 to flow of blood. FIG. 49B shows a top view (from the perspective inside of the artificial right atrium) of the transcatheter device having proximal segment 918 of the main shaft. As seen here, the inner side of the shroud 914 faces the right ventricle.

Figure 50A:
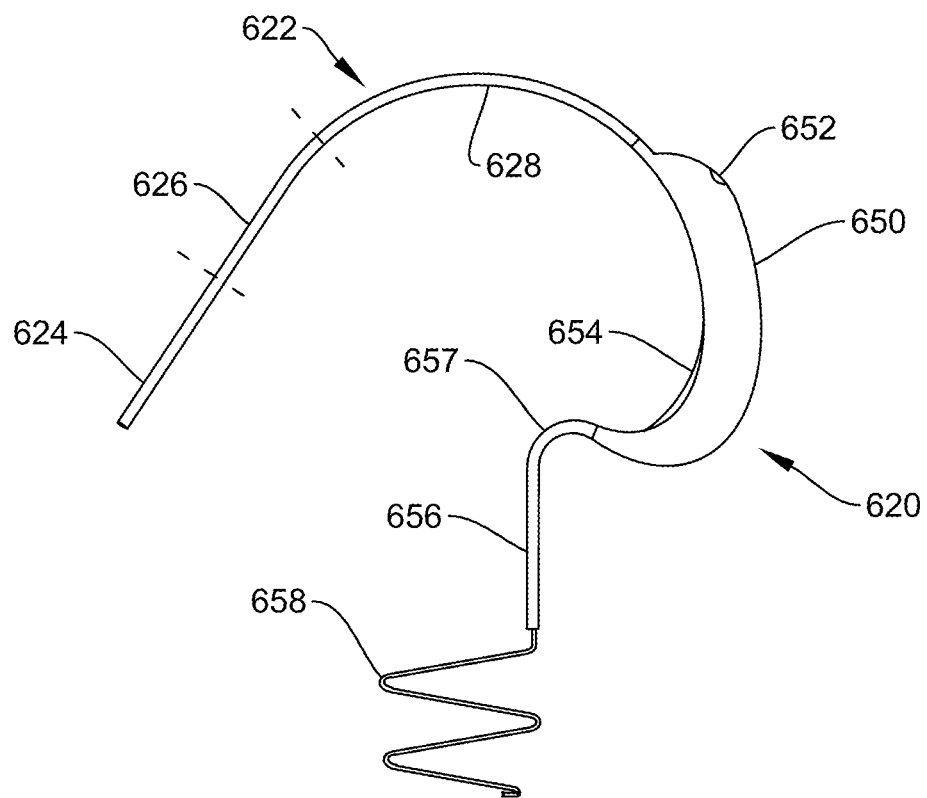
FIGS. 50A-C show another example of a transcatheter device.
Figure 50B:
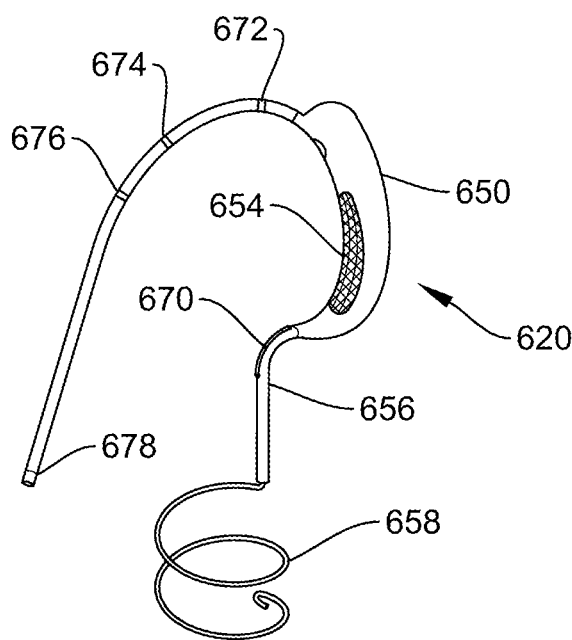
Figure 50C:
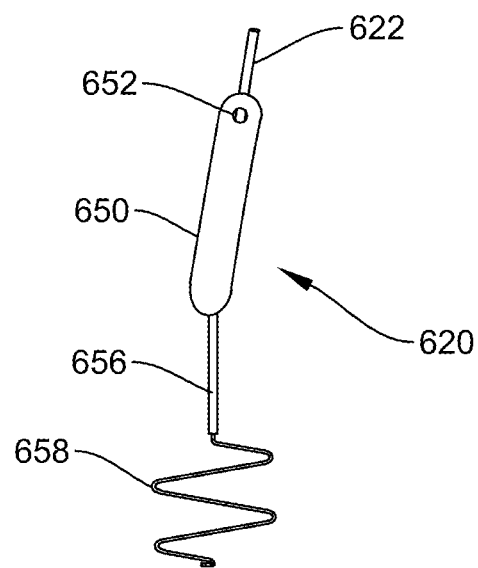

FIGS. 50A-C show another embodiment of the transcatheter device. In this embodiment, the transcatheter device 620 has a distal tail 622, spacer body 650, proximal segment 656 of the main shaft, and a spiral coil 658. As shown in FIG. 50A (side view), distal tail 622 has three segments with different flexibility characteristics. There is a distal segment 624, a middle segment 626, and proximal segment 628. Distal segment 624 is more flexible than both middle segment 626 and proximal segment 628. Furthermore, middle segment 626 is more flexible than proximal segment 628. That is, proximal segment 628 is stiffer than both middle segment 626 and distal segment 624. This preformed (pre-biased) curved shape of distal tail 622 along with the progressively increasing flexibility of the distal tail 622 along its length makes it less traumatic to the pulmonary artery. This reduces risk of injury to the pulmonary artery.

The total length of the distal tail 622 is about 20 cm. The length of distal segment 624 is about 5 cm. The length of middle segment 626 is about 5 cm. The length of proximal segment 628 is about 10 cm. The length of the proximal segment 656 of the main shaft is about 5 cm. Also note that proximal segment 656 of the main shaft has a rounded gooseneck curve 657 as it connects with spacer body 650.

FIGS. 50B (perspective view) and 50C (back view) show spacer body 650 having a proximal opening 654 and a distal opening 652 to allow blood flow through the spacer body 650. There is also shows a series of radiopaque markers on the transcatheter device. There is a radiopaque strip 670 on the proximal segment 656 of the main shaft. There is further a series of radiopaque bands (672, 674, 676) on the distal tail 622. There is also a radiopaque band 678 at the tip of the distal tail 622.

Figures 51A, 51B:
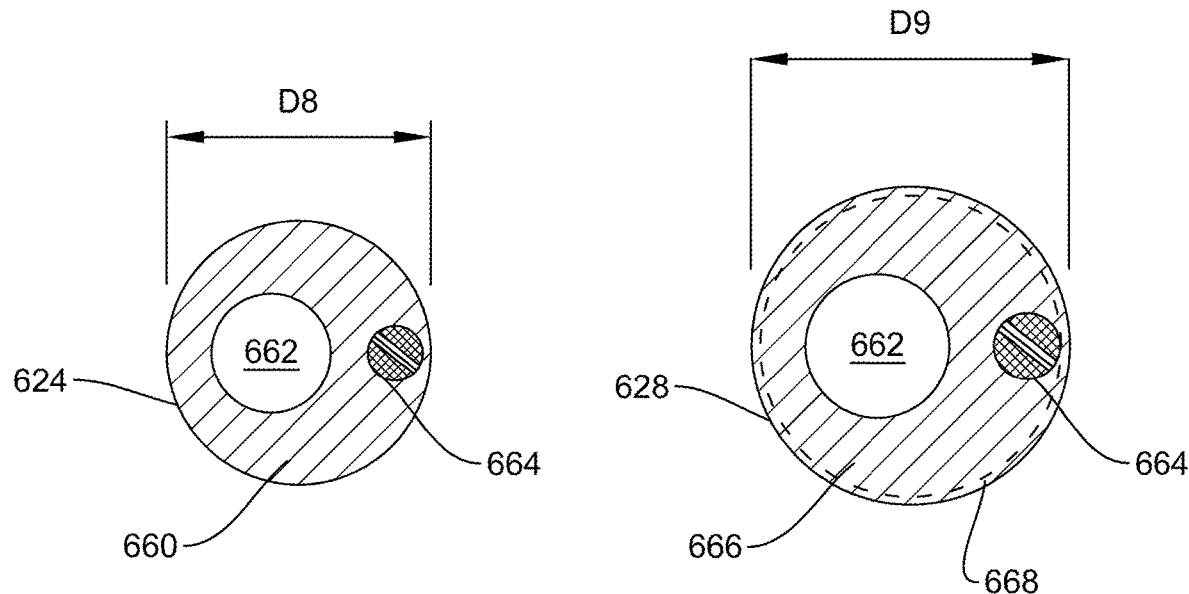
FIGS. 51A and 51B show cross-sections of the main shaft of the transcatheter device.

FIGS. 51A and 51B show cross-section views of the main shaft of the transcatheter device 620. FIG. 51A is for the distal segment 624, which comprises a jacket 660 made of Pellethane 90A (grade 90 on the Shore A hardness scale) and a lumen 662 which is lined with ePTFE. The diameter D8 of distal segment 624 is about 3 mm. Pellethane is a brand of thermoplastic polyurethane elastomers designed for use in medical devices. There is also a nitinol core wire 664 for structural support through the length of the main shaft of the transcatheter device 620. This nitinol core wire 664 gives distal tail 622 its preformed curved shape. Middle segment 626 has the same structure, but the jacket is made of Pellethane 55D (grade 55 on the Shore D hardness scale) for the jacket. The Pellethane 55D material is harder than the Pellethane 90A material used for the distal segment 624. The diameter of middle segment 626 is about 3 mm.

FIG. 51B is for the proximal segment 628, which comprises a jacket 666 made of Pellethane 77D (grade 77 on the Shore D hardness scale) and the lumen 662 which is lined with ePTFE. The Pellethane 77D material is harder than the Pellethane 55D used for the middle segment 626. To give extra stiffness, proximal segment 628 is sheathed with stainless steel braiding 668. Proximal segment 628 is about 4 mm diameter. The nitinol core wire 664 continues through proximal segment 628. Proximal segment 656 of the main shaft also has a similar structure and material composition. Thus, proximal segment 628 and proximal segment 656 of the main shaft have similar stiffness.

Figure 52:
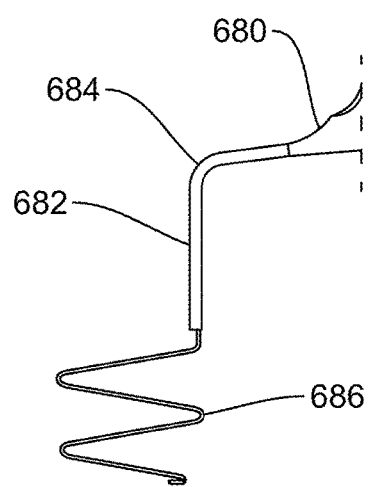
FIG. 52 shows an alternate design for the proximal segment of the main shaft.

FIG. 52 shows an alternate design for the proximal segment of the main shaft. Here, proximal segment 682 of the main shaft has a sharp right angle curve 684 as it connects to spacer body 680. This is different from the rounded gooseneck curve 657 for the design shown in FIG. 50A. Also shown here is spiral coil 686.

Figure 53A:
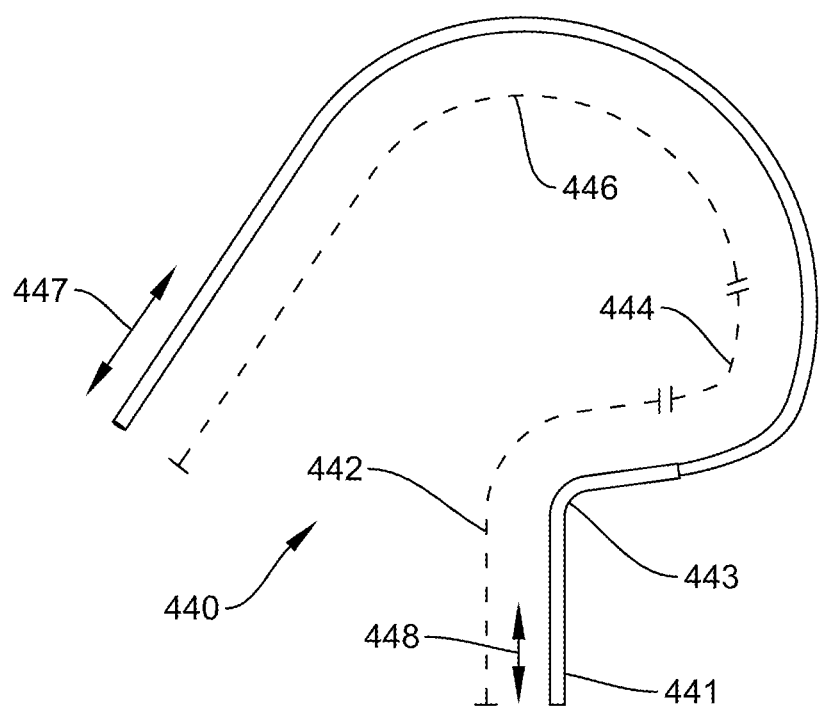
FIGS. 53A and 53B show the shape of the overall trunk of an example transcatheter device.
Figure 53B:
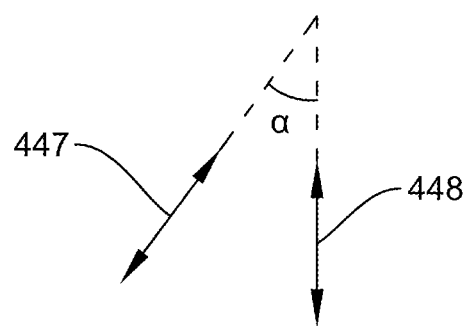

FIGS. 53A and 53B show the overall shape of the trunk of the transcatheter device. The overall trunk comprises the main shaft and the distal tail. The main shaft comprises a proximal segment and a spacer body segment. The proximal segment is where the intravascular anchor is attached. The proximal segment leads to the spacer body. The spacer body segment is where the spacer body is mounted. Continuing from the main shaft is the distal tail.

Figures 53C, 53D:
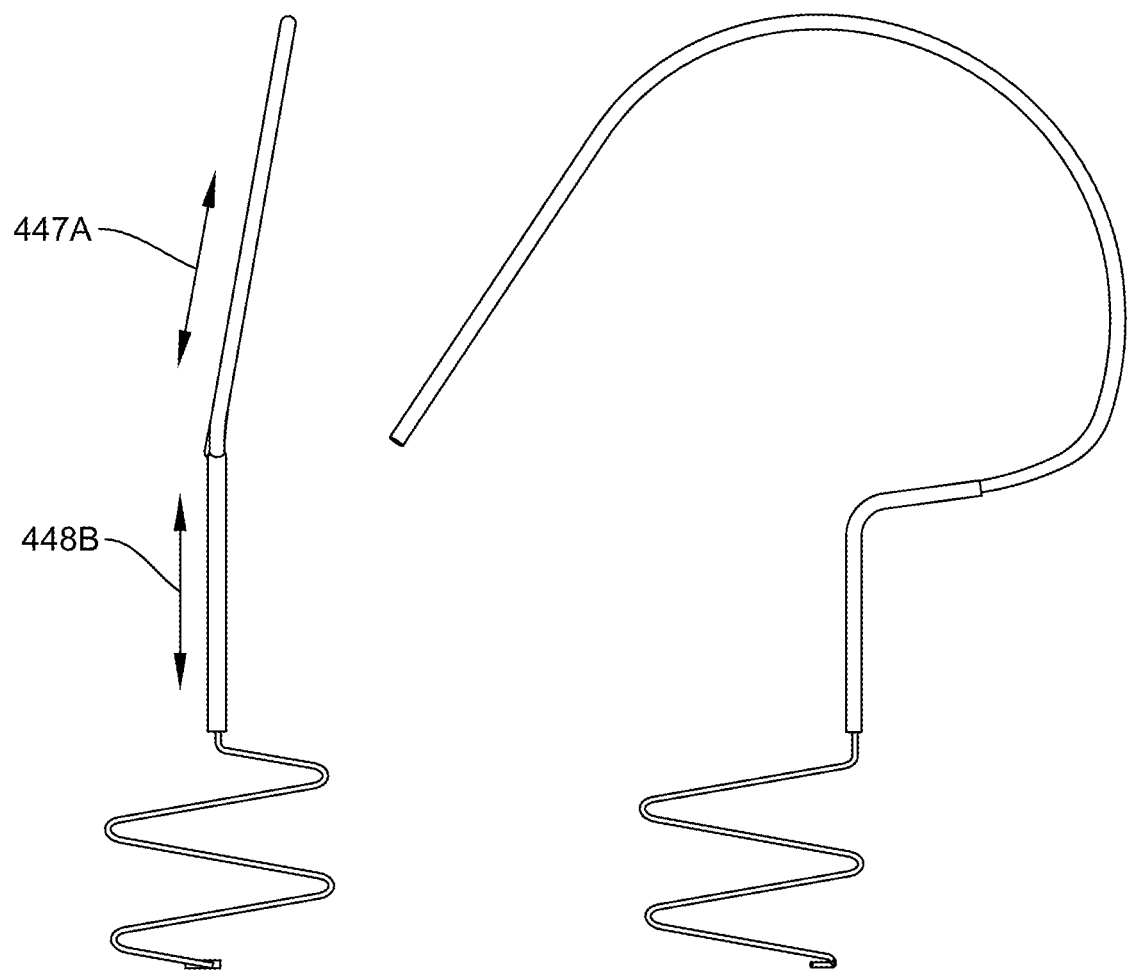
FIGS. 53C-E show the shape of the overall trunk of an example transcatheter device.

FIG. 53A shows an overall trunk shape 440 comprising a main shaft, which comprises a proximal segment 442 and a spacer segment 444. The trunk 440 further comprises distal tail 446. Proximal segment 442 has only a single bend 443 with a corner-turning shape. More information about the possible characteristics of this bend 443 is described in the above Summary section in the heading "Proximal Portion". Spacer segment 444 and the distal tail 446 form an overall C-shape. As shown in FIGS. 53C and 53D, the overall C-shape is designed to embrace the path along pulmonary artery—the supraventricular crest of RV—the tricuspid valve—the right atrium and then toward IVC. The RV supraventricular crest, which is an outer wall of ascending aorta, anatomically provides a robust buttress for this embracing function of the device.

The distal segment of distal tail 446 has a longitudinal axis 447. The initial straight section 441 of the proximal segment of the main shaft has a longitudinal axis 448. FIG. 53B shows the angle α between longitudinal axis 447 and longitudinal axis 448, wherein α is in the range of 20-60°. Thus, the distal segment of distal tail 446 could point in a direction that is within 20-60° relative to the direction of initial straight section 441 of proximal segment 442.

Figure 53E:
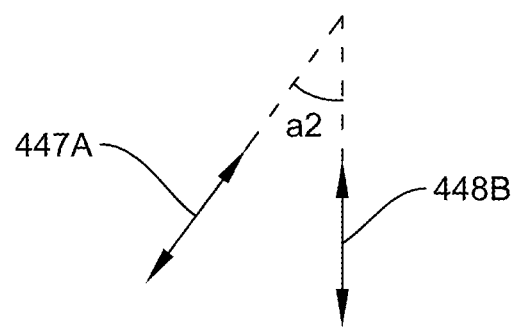

FIGS. 53C and 53E show the angle α2 between longitudinal axis 447A and longitudinal axis 448B, wherein α2 is in the range of 0-15°.

Figure 54A:
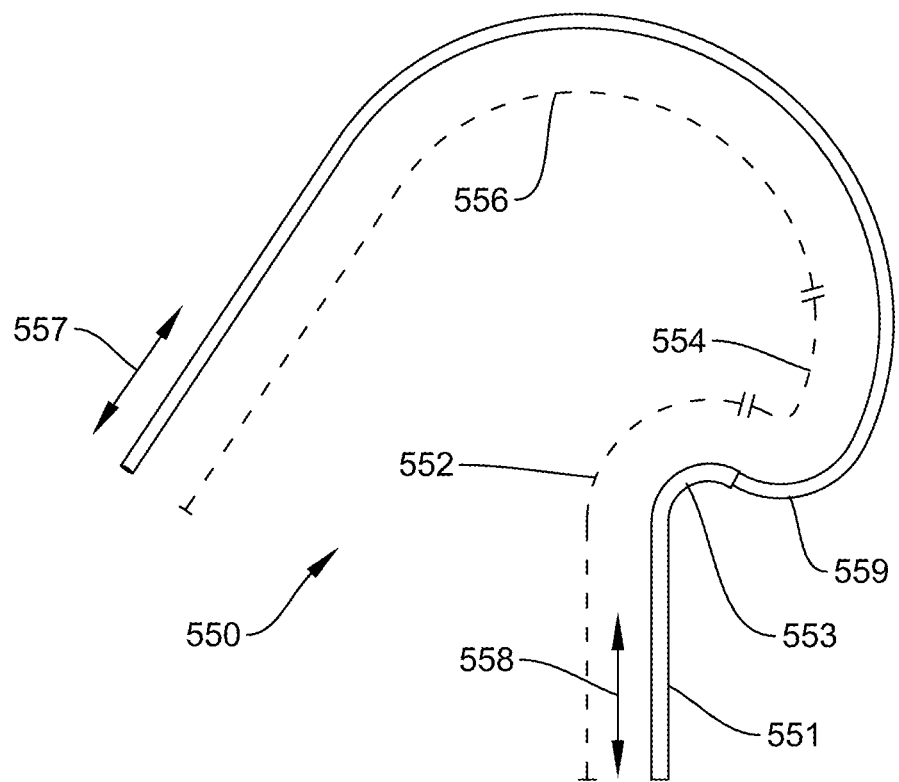
FIGS. 54A and 54B shows a different design for the shape of the overall trunk.
Figure 54B:
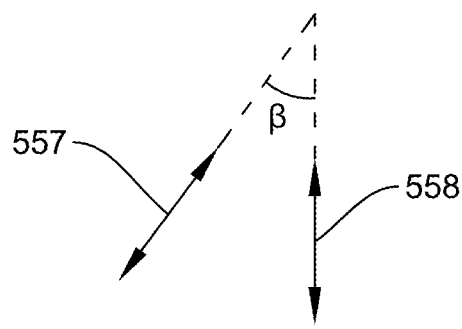

FIG. 54A shows a different overall trunk shape 550 in which the main shaft has two bends 553 and 559 in a curved gooseneck shape. These two bends occur in the proximal segment 552 and the spacer segment 554 of the main shaft. In this design, bends 553 and 559 create a smoothly curving S-shape in the main shaft. The first bend 553 has a curvature in one direction (downward), whereas the second bend 559 has a curvature in a different direction, i.e. generally the opposite direction (upward). First bend 553 encompasses a length in the range of 1-5 cm on the main shaft. Second bend 555 encompasses a length in the range of 1-5 cm on the main shaft. FIG. 54B shows the angle β between longitudinal axis 557 and longitudinal axis 558, wherein β is in the range of 20-60°. Thus, the distal segment of distal tail 556 could point in a direction that is within 20-60° relative to the direction of initial straight section 551 of proximal segment 552.

Figures 54C, 54D:
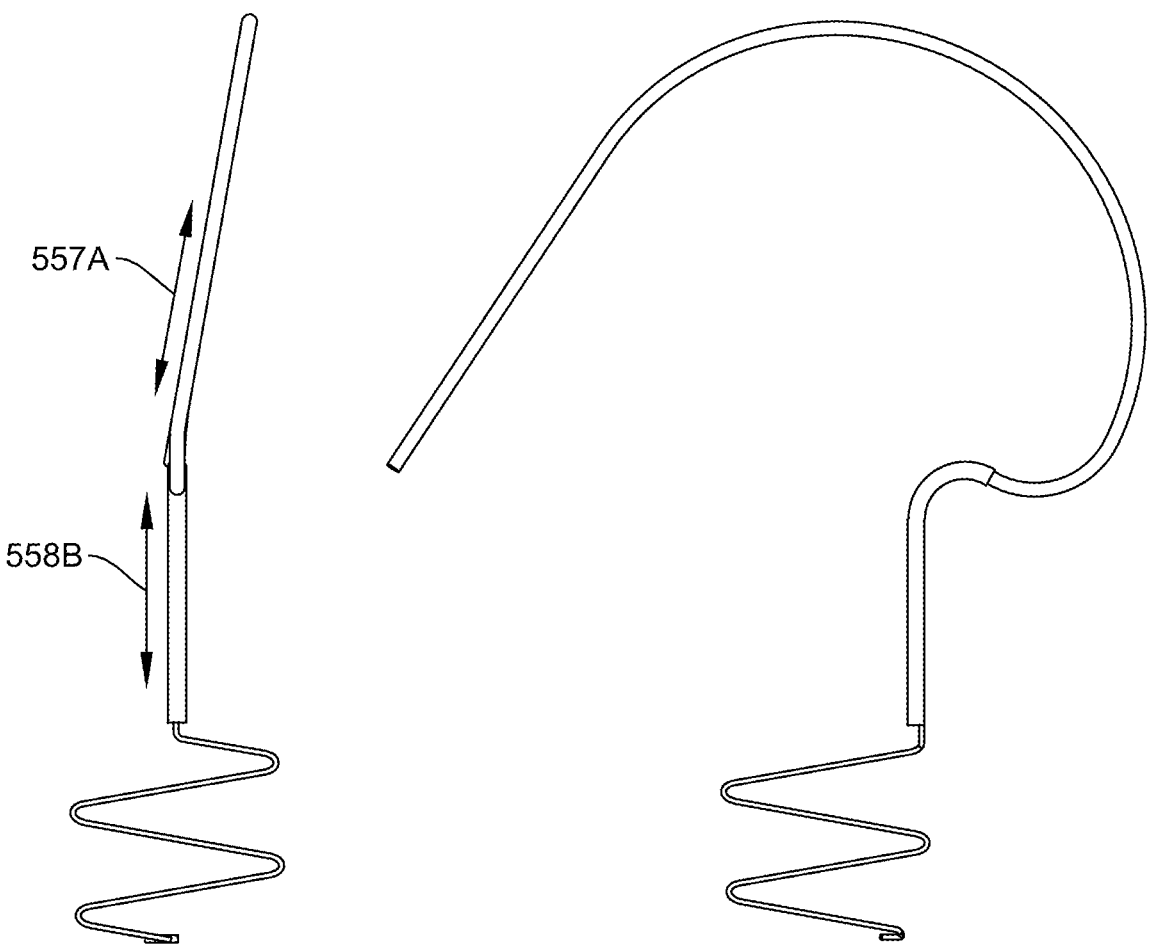
FIGS. 54C-E show a different design for the shape of the overall trunk.
Figure 54E:
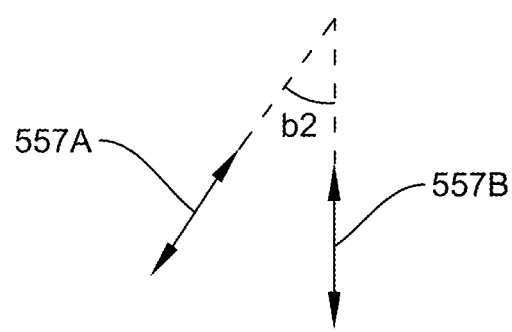

As shown in FIGS. 54A and 54D, the overall C-shape is designed to embrace the path along pulmonary artery—the supraventricular crest of RV—the tricuspid valve—the right atrium and then toward IVC. The RV supraventricular crest, which is an outer wall of ascending aorta, anatomically provides a robust buttress for this embracing function of the device. FIGS. 54C and 54E show the angle β2 between longitudinal axis 557A and longitudinal axis 557B, wherein β2 is in the range of 0-15°.

Experimental Testing: A prototype of the transcatheter device was tested in a pig model of tricuspid valve defect and its effectiveness assessed by echocardiogram images of the defective tricuspid valve. Prior to treatment, echocardiogram showed there was severe tricuspid valve regurgitation rated grades V-VI. The transcatheter device was implanted and the spacer body was positioned across the tricuspid valve. Echocardiogram images taken 6 weeks after implantation and showed reduction of tricuspid valve regurgitation rated grade II.

We also conducted an experiment to test retrieval of the transcatheter device in the pig model of tricuspid valve defect. A prototype transcatheter device was implanted across the tricuspid valve. Retrieval was performed at three time points: (group 1) immediately after secure placement of the transcatheter device; (group 2) two weeks after implanting; and (group 3) four weeks after implanting. In each case, retrieval was attempted with a conventional catheter snaring system. This retrieval procedure was performed by grasping the proximal tip of the spiral coil of the transcatheter device, withdrawing the snaring system, and pulling out the entire transcatheter device through the entry vein. In groups 1 and 2 (immediate and two weeks after), the transcatheter device was successfully removed without any problems. Post-procedure echocardiogram confirmed no abnormality caused by the transcatheter device being implanted, and no trauma caused by its subsequent removal. However, in group 3 (four weeks after), retrieval was not possible because of strong adhesion of the spiral coil to the inferior vena cava. This indicates that the spiral coil successfully functions as a secure anchor within the inferior vena cava.

The descriptions and examples given herein are intended merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A method of treating tricuspid valve regurgitation in a patient's heart, comprising:
    having a transcatheter device comprising (i)-(iv) below;
        (i) a main shaft;
        (ii) a proximal portion comprising a proximal segment of the main shaft and an intravascular anchor;
        (iii) a distal tail comprising a distal portion of the main shaft;
        (iv) a spacer body mounted on the main shaft and located between the proximal segment of the main shaft and the distal tail;
    inserting the transcatheter device into a femoral vein;
    advancing the transcatheter device through an inferior vena cava;
    advancing the transcatheter device through a right atrium of the heart;
    advancing the transcatheter device across a tricuspid valve and into a right ventricle of the heart;
    advancing the transcatheter device towards a pulmonary artery;
    advancing the distal tail into the pulmonary artery for a distance of at least 10 cm into the pulmonary artery;
    positioning the spacer body between leaflets of the tricuspid valve;
    lodging the intravascular anchor within the inferior vena cava.

2. The method of claim 1, further comprising positioning the spacer body to abut against a supraventricular crest of the heart.

3. The method of claim 2, wherein the abutting against the supraventricular crest occurs at a location within the distal half of the spacer body.

4. The method of claim 2, wherein the tricuspid valve has a tricuspid annulus and there is an annular plane defined for the tricuspid annulus;
    wherein the annular plane is along an x-axis of the tricuspid annulus and orthogonal to a Y-axis of the tricuspid annulus;
    wherein the spacer body is positioned at an oblique angle relative to the annular plane.

5. The method of claim 2, wherein the main shaft comprises a lumen, and the method further comprises:
    inserting a guidewire into the femoral vein;
    advancing the guidewire through the inferior vena cava;
    advancing the guidewire through the right atrium;

advancing the guidewire to traverse the tricuspid valve and into the right ventricle;
introducing the guidewire into the lumen of the shaft;
advancing the transcatheter device over the guidewire.

6. The method of claim 1, wherein the distal tail is advanced past a first branching point of the pulmonary artery.

7. The method of claim 6, wherein the distal tail is advanced past a second branching point of the pulmonary artery.

8. The method of claim 7, wherein the distal tail of the transcatheter device is advanced past a third branching point of the pulmonary artery.

9. The method of claim 1, wherein the distal tail of the transcatheter device is advanced a least 15 cm into the pulmonary artery.

10. The method of claim 1, wherein the spacer body has an opening through which blood flows through the spacer body.

11. The method of claim 1, wherein the pulmonary artery is a left-side pulmonary artery.

* * * * *